(12) United States Patent
Stoessel et al.

(10) Patent No.: US 8,114,531 B2
(45) Date of Patent: Feb. 14, 2012

(54) MATERIALS FOR ORGANIC ELECTROLUMINESCENT DEVICES

(75) Inventors: Philipp Stoessel, Frankfurt am Main (DE); Arne Buesing, Frankfurt am Main (DE); Holger Heil, Darmstadt (DE)

(73) Assignee: Merck Patent GmbH (DE)

( * ) Notice: Subject to any disclaimer, the term of this patent is extended or adjusted under 35 U.S.C. 154(b) by 302 days.

(21) Appl. No.: 12/375,285

(22) PCT Filed: Jul. 2, 2007

(86) PCT No.: PCT/EP2007/005848
§ 371 (c)(1),
(2), (4) Date: Jan. 27, 2009

(87) PCT Pub. No.: WO2008/011964
PCT Pub. Date: Jan. 31, 2008

(65) Prior Publication Data
US 2010/0013381 A1    Jan. 21, 2010

(30) Foreign Application Priority Data
Jul. 28, 2006   (DE) .................. 10 2006 035 035

(51) Int. Cl.
*H01L 51/54* (2006.01)
(52) U.S. Cl. ........ 428/690; 428/917; 528/417; 528/422; 564/428; 564/434
(58) Field of Classification Search .................. 428/690, 428/917; 528/417, 422; 564/428, 434
See application file for complete search history.

(56) References Cited

U.S. PATENT DOCUMENTS
2005/0048313 A1   3/2005   Sotoyama
2005/0212409 A1   9/2005   Shi et al.
2005/0214566 A1   9/2005   Shi et al.
2006/0134538 A1*  6/2006   Radu et al. ................. 430/58.15

FOREIGN PATENT DOCUMENTS
EP   0866110 A1    9/1998
EP   1289343 A1    3/2003
EP   1359790 A2   11/2003
EP   1452574 A1    9/2004
JP   2000-150167 A  5/2000

OTHER PUBLICATIONS

Rudolf et. al., STIC Search Section, 1942, Justus Liebigs Annalen der Chemie, vol. 553, pp. 47-51.*
Rudolf et. al., Zur Kenntnis des Dinaphtylendioxyds, 1942, Justus Liebigs Annalen der Chemie, pp. 103-146.*
"Quick synthesis and properties of peri-xanthenoxanthene", Database CAPLUS, Accession No. 2006:334795, Apr. 12, 2006.
Faguang Xuebao, Chinese Journal of Luminescence, 2006, vol. 27, No. 1, pp. 95-99.
"Polarized luminescence of complex molecules in the vapor phase", Database CAPLUS, Accession No. 1985:228762, Jun. 29, 1985.
Blokhin, A.P., et al., "Polarized luminescence of complex molecules in the vapor phase," Spectroscopy Letters, 1985, vol. 18, No. 4, pp. 301-316.

* cited by examiner

*Primary Examiner* — Jennifer Chriss
*Assistant Examiner* — Gregory Clark
(74) *Attorney, Agent, or Firm* — Connolly Bove Lodge & Hutz LLP

(57) ABSTRACT

The present invention relates to the compounds of the formulae (1) to (8) and to the use thereof in organic electroluminescent devices, in particular in blue-emitting devices. The compounds of the formulae (1) to (8) are used as host material or dopant in the emitting layer or also in a hole- or electron-transport layer.

16 Claims, No Drawings

MATERIALS FOR ORGANIC ELECTROLUMINESCENT DEVICES

CROSS-REFERENCE TO RELATED APPLICATIONS

Related Applications

This application is a national stage application (under 35 U.S.C. §371) of PCT/EP2007/005848, filed Jul. 2, 2007, which claims benefit of German application 10 2006 035035.9, filed Jul. 28, 2006.

BACKGROUND OF THE INVENTION

The present invention relates to organic semiconductors and to the use thereof in organic electronic devices.

Organic semiconductors are being developed for a number of different applications which can be ascribed to the electronics industry in the broadest sense. The structure of organic electroluminescent devices (OLEDs) in which these organic semiconductors are employed as functional materials is described, for example, in U.S. Pat. No. 4,539,507, U.S. Pat. No. 5,151,629, EP 0676461 and WO 98/27136. However, these devices still exhibit considerable problems which require urgent improvement:
1. Many dopants in accordance with the prior art are only accessible in complex multistage synthetic methods.
2. The lifetime of the organic electroluminescent devices in accordance with the prior art is still inadequate for high-quality applications.
3. The thermal stability, in particular of many blue dopants, is inadequate.
4. Many compounds, in particular blue dopants, in accordance with the prior art have high sensitivity to oxygen and light, which makes synthesis and handling thereof considerably more difficult.

Prior art which may be mentioned in the case of blue-emitting compounds is the use of arylvinylamines (for example WO 04/013073, WO 04/016575, WO 04/018587). However, these compounds are thermally unstable and cannot be evaporated without decomposition, which requires high technical complexity for OLED production and thus represents an industrial disadvantage. A further disadvantage is the emission colour of these compounds: while dark-blue emission (CIE y coordinates in the range 0.15-0.18) is described in the prior art with these compounds, it has not been possible to reproduce these colour coordinates in simple devices in accordance with the prior art. Green-blue emission is obtained here. It is not apparent how blue emission can be generated with these compounds.

Also known as blue and green emitters in accordance with the prior art are aromatic diamines with condensed aromatic compounds, for example with anthracene, pyrene or chrysene (WO 04/078872, EP 1437395, WO 04/044088). However, these likewise do not have satisfactory properties in the device, in particular with respect to the lifetime, but also with respect to the operating voltage. Furthermore, these compounds are very sensitive to oxygen and light, which makes handling thereof more difficult, in particular on an industrial scale.

There therefore continues to be a demand for improved materials, in particular blue-emitting compounds, which are thermally stable, result in good efficiencies and at the same time in long lifetimes in organic electronic devices, give reproducible results during the production and operation of the device and are readily accessible synthetically.

BRIEF SUMMARY OF THE INVENTION

Surprisingly, it has been found that substituted derivatives of peri-xanthenoxanthene, in particular those which are substituted by aromatic substituents or further substituents described below, are very suitable for use in organic electroluminescent devices. These compounds have high thermal stability. Furthermore, an increase in the efficiency and lifetime of the organic electronic device compared with materials in accordance with the prior art is possible using these materials. The present invention therefore relates to these materials and to the use thereof in organic electronic devices.

The invention relates to compounds of the formulae (1) to (4):

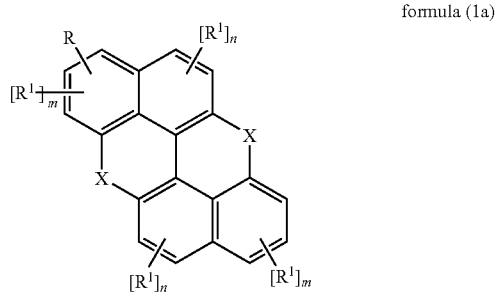

formula (1a)

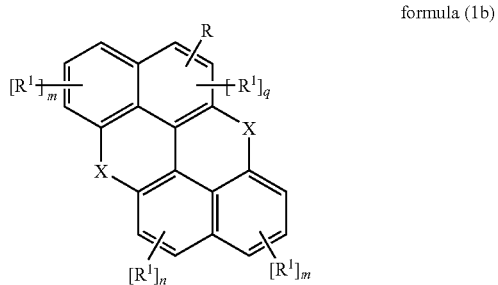

formula (1b)

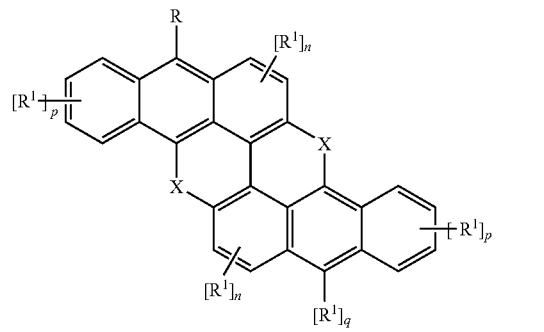

formula (2)

formula (3)

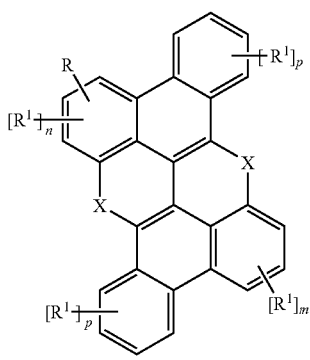

formula (4)

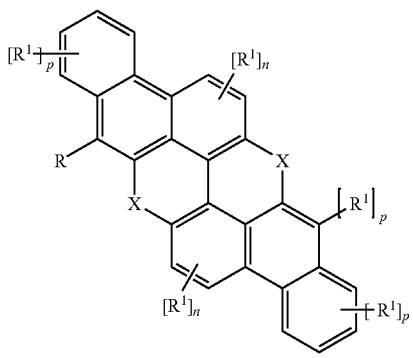

where the following applies to the symbols and indices:

X is on each occurrence, identically or differently, O, S, NR$^1$, C(R$^1$)$_2$, BR$^1$, PR$^1$, POR$^1$, SO or SO$_2$;

R is on each occurrence, identically or differently, an N(Ar)$_2$, C(=O)Ar, P(=O)Ar$_2$, S(=O)Ar, S(=O)$_2$Ar, CR$^2$=CR$^2$Ar, OAr, SAr, Si(R$^1$)$_3$ group, a straight-chain alkyl group having 1 to 40 C atoms, a branched or cyclic alkyl group having 3 to 40 C atoms, each of which may be substituted by one or more radicals R$^2$ and in which one or more H atoms may be replaced by F, Cl, Br, I, CN or NO$_2$, a straight-chain alkoxy group having 2 to 40 C atoms or a branched or cyclic alkoxy group having 3 to 40 C atoms, where the alkoxy group may in each case be substituted by one or more radicals R$^2$, where one or more non-adjacent CH$_2$ groups in the alkoxy groups may be replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms may be replaced by F, Cl, Br, I, CN or NO$_2$, or an aromatic or heteroaromatic ring system having 5 to 60 aromatic ring atoms, each of which may be substituted by one or more non-aromatic radicals R$^1$; R here may also form a mono- or polycyclic ring system with adjacent substituents R$^1$;

R$^1$ is on each occurrence, identically or differently, H, F, Cl, Br, I, CHO, N(Ar)$_2$, C(=O)Ar, P(=O)Ar$_2$, S(=O)Ar, S(=O)$_2$Ar, CR$^2$=CR$^2$Ar, OAr, SAr, CN, NO$_2$, Si(R$^{23}$, B(OR$^2$)$_2$, OSO$_2$R$^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals R$^2$, where one or more non-adjacent CH$_2$ groups may be replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms may be replaced by F, Cl, Br, I, CN or NO$_2$, or an aromatic or heteroaromatic ring system having 5 to 60 aromatic ring atoms, each of which may be substituted by one or more non-aromatic radicals R$^1$, or a combination of these systems; two or more adjacent substituents R$^1$ here may also form a mono- or polycyclic ring system with one another or R$^1$ with R;

Ar is on each occurrence, identically or differently, an aromatic or heteroaromatic ring system having 5 to 40 aromatic ring atoms, which may be substituted by one or more non-aromatic radicals R$^1$; two radicals Ar which are bonded to the same nitrogen or phosphorus atom may also be linked to one another here by a single bond or a bridge selected from B(R$^2$), C(R$^2$)$_2$, Si(R$^2$)$_2$, C=O, C=NR$^2$, C=C(R$^2$)$_2$, O, S, S=O, SO$_2$, N(R$^2$), P(R$^2$) and P(=O)R$^2$;

R$^2$ is on each occurrence, identically or differently, H or an aliphatic, aromatic and/or heteroaromatic hydrocarbon radical having 1 to 20 C atoms, in which, in addition, H atoms may be replaced by F; two or more adjacent substituents R$^2$ here may also form a mono- or polycyclic aliphatic or aromatic ring system with one another;

n is on each occurrence, identically or differently, 0, 1 or 2;

m is on each occurrence, identically or differently, 0, 1, 2 or 3;

p is on each occurrence, identically or differently, 0, 1, 2, 3 or 4;

q is on each occurrence, identically or differently, 0 or 1;

the following compounds are excluded from the invention:

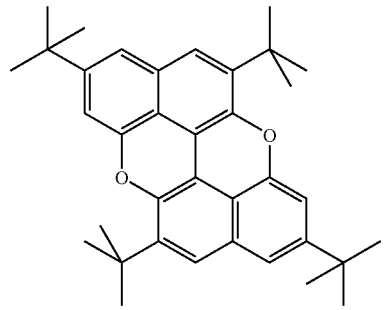

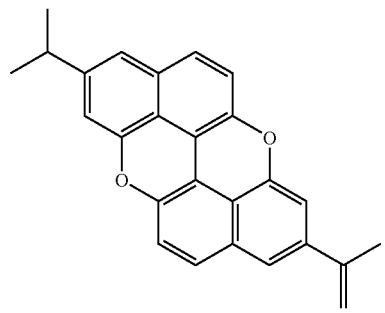

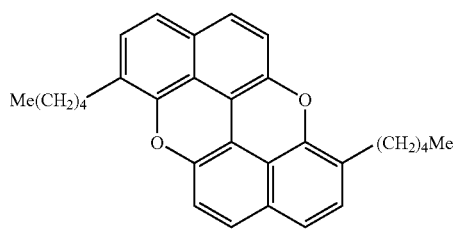

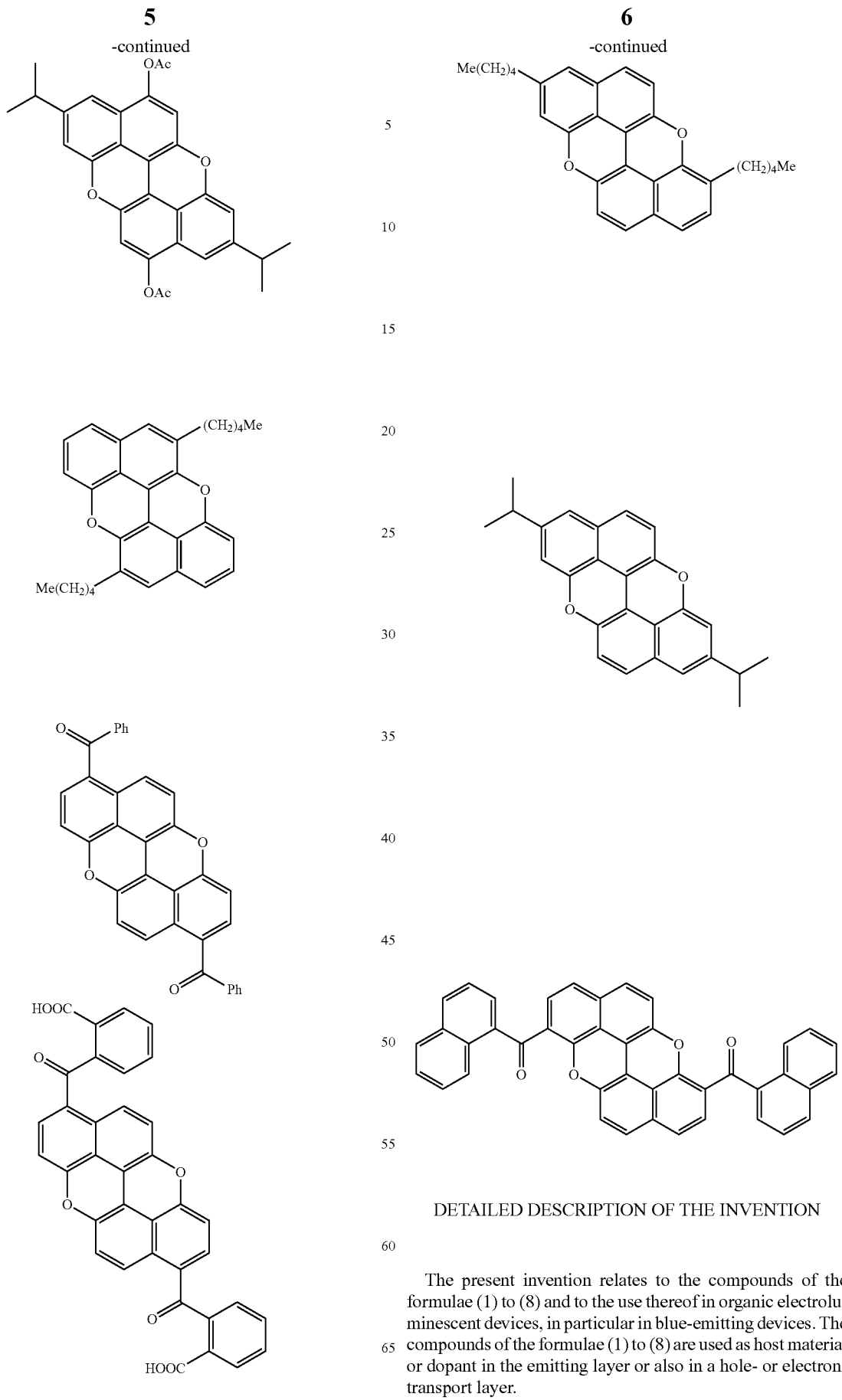
DETAILED DESCRIPTION OF THE INVENTION
The present invention relates to the compounds of the formulae (1) to (8) and to the use thereof in organic electroluminescent devices, in particular in blue-emitting devices. The compounds of the formulae (1) to (8) are used as host material or dopant in the emitting layer or also in a hole- or electron-transport layer.

The invention furthermore relates to the compounds of the following formulae (5) to (8):

formula (5)

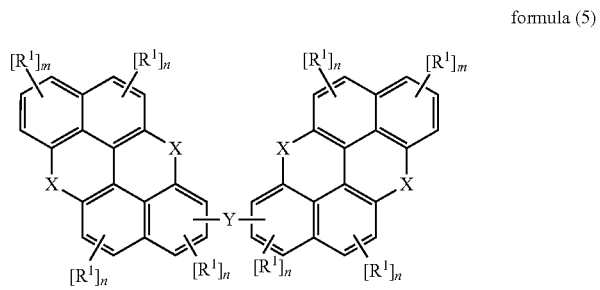

formula (6)

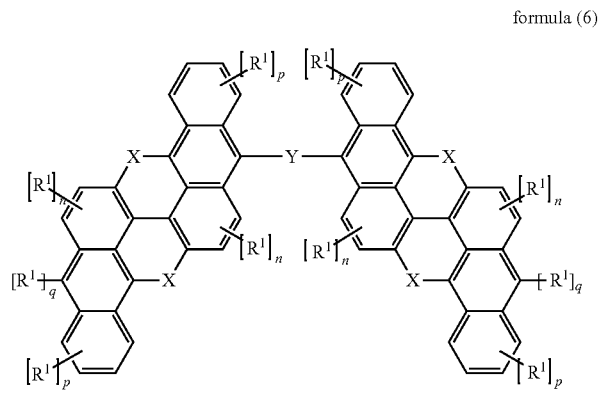

formula (7)

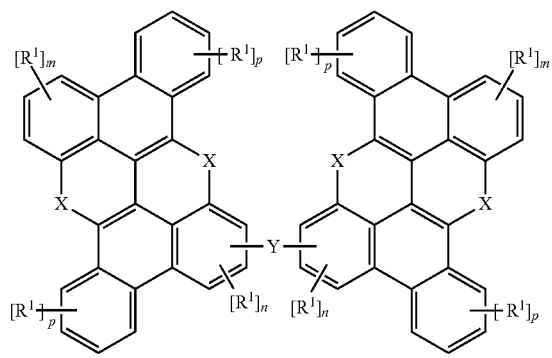

formula (8)

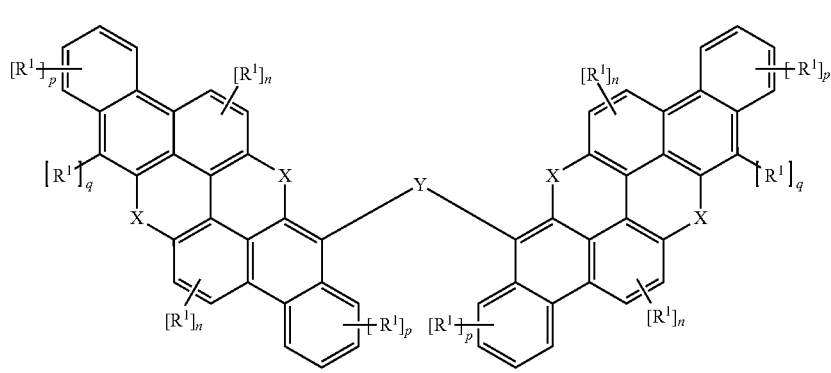

where $R^1$, $R^2$, X, m, n, p and q have the same meaning as described above, and furthermore:

Y is a single bond, a C(=O), P(=O)Ar, S(=O), S(=O)$_2$, N(Ar), O, S group, an alkylene or alkylidene group having 1 to 20 C atoms or a divalent aromatic ring system having 5 to 40 aromatic ring atoms, which may be substituted by one or more non-aromatic radicals $R^1$.

If Y represents a group of the formula P(=O)Ar or N(Ar), the group Ar here may also represent a further group having the skeleton of the formulae (1) to (4), resulting in the formation of $C_3$-symmetrical compounds.

For reasons of clarity, the numbering is shown for the example of peri-xanthenoxanthene in the following formula:

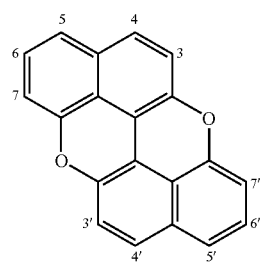

The compounds of the formulae (1) to (8) preferably have a glass transition temperature $T_g$ of greater than 70° C., particularly preferably greater than 100° C., very particularly preferably greater than 130° C.

For the purposes of this invention, adjacent radicals R and $R^1$ are taken to mean radicals which are either bonded to the same carbon atom or are bonded to adjacent carbon atoms.

For the purposes of this invention, an aryl group contains 6 to 40 C atoms; for the purposes of this invention, a heteroaryl group contains 2 to 40 C atoms and at least 1 heteroatom, with the proviso that the sum of C atoms and heteroatoms is at least 5. The heteroatoms are preferably selected from N, O and/or S. An aryl group or heteroaryl group here is taken to mean either a single aromatic ring, i.e. benzene, or a single heteroaromatic ring, for example pyridine, pyrimidine, thiophene, etc. or a condensed aryl or heteroaryl group, for example naphthalene, anthracene, pyrene, quinoline, isoquinoline, etc.

For the purposes of this invention, an aromatic ring system contains 6 to 60 C atoms in the ring system. For the purposes of this invention, a heteroaromatic ring system contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which a plurality of aryl or heteroaryl groups may also be interrupted by a short non-aromatic unit (preferably less than 10% of the atoms other than H), such as, for example, an $sp^3$-hybridised C, N or O atom. Thus, for example, systems such as 9,9'-spirobifluorene, 9,9-diarylfluorene, triarylamine, diaryl ether, stilbene, benzophenone, etc., are also intended to be taken to mean aromatic ring systems for the purposes of this invention. An aromatic or heteroaromatic ring system is likewise taken to mean systems in which a plurality of aryl or heteroaryl groups are linked to one another by single bonds, for example biphenyl, terphenyl or bipyridine. For the purposes of the present invention the skeletons of the formulae (1) to (4), i.e. peri-xanthenoxanthene and the other skeletons shown above, are also taken to mean aromatic ring systems.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. A $C_1$- to $C_{40}$-alkoxy group is particularly preferably taken to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may also in each case be substituted by the above-mentioned radicals R and which can be linked to the aromatic or heteroaromatic ring system via any desired positions, is taken to mean, in particular, groups derived from benzene, naphthalene, anthracene, phenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, peri-xanthenoxanthene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole. Furthermore, aromatic ring systems are also taken to mean any desired combination of the above-mentioned aryl groups, for example binaphthyl, naphthylanthryl, etc.

Preference is given to structures of the formulae (9) to (24):

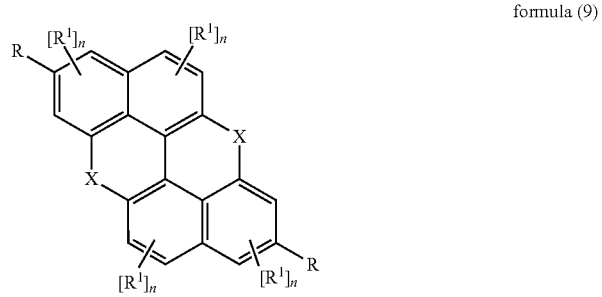

formula (9)

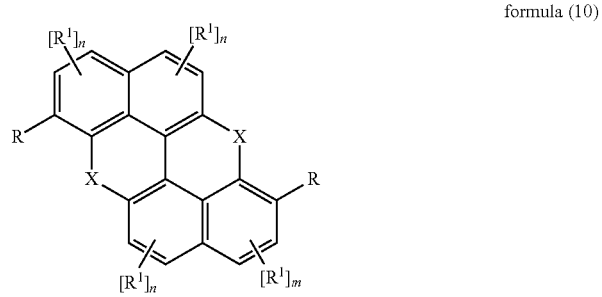

formula (10)

-continued
formula (11)
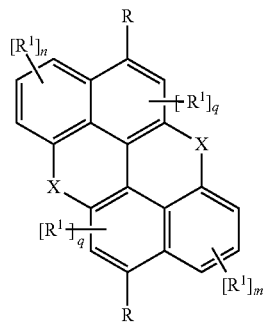
formula (12)
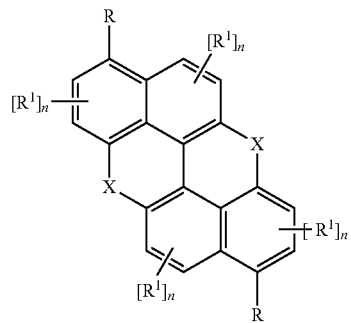
formula (13)
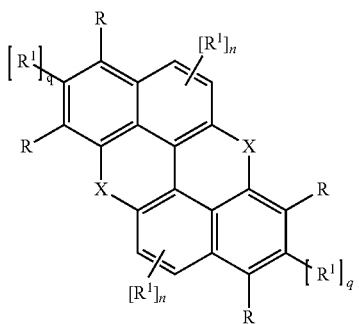
formula (14)
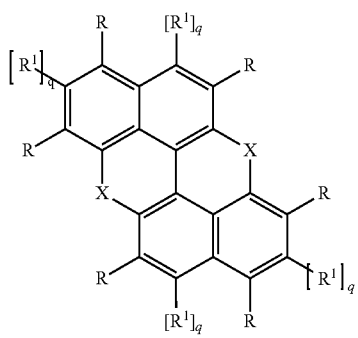
formula (15)
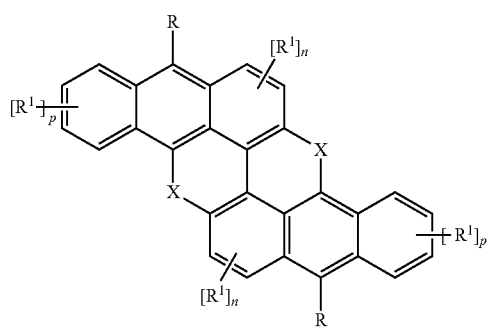
formula (16)
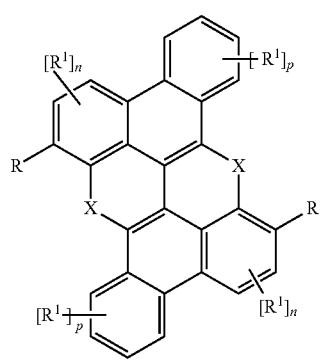
formula (17)
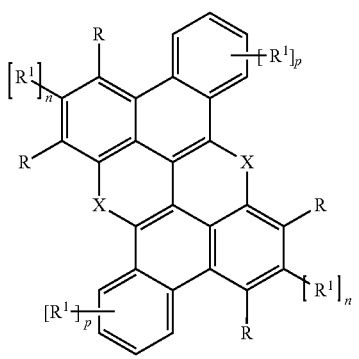
formula (18)
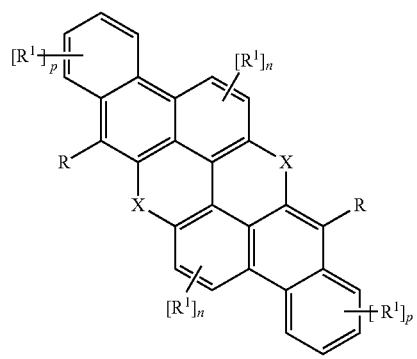

formula (19)
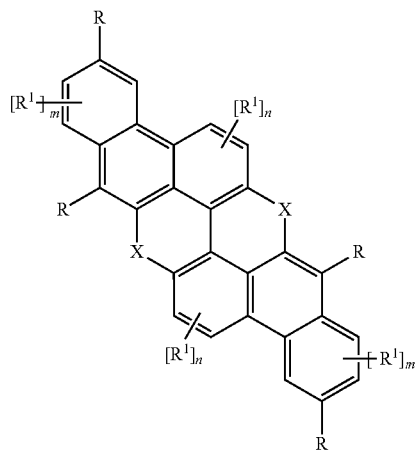
formula (20)
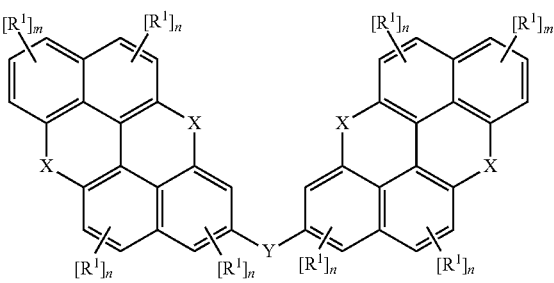
formula (21)
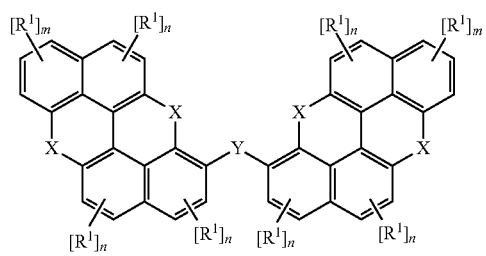
formula (22)
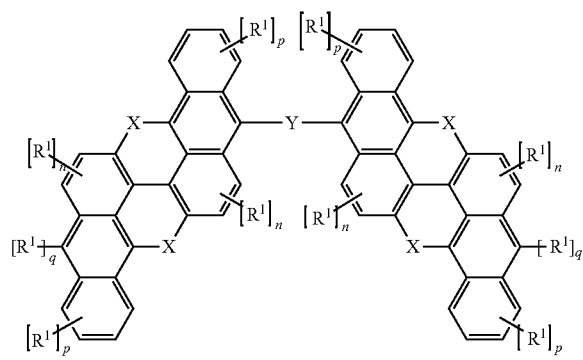
formula (23)
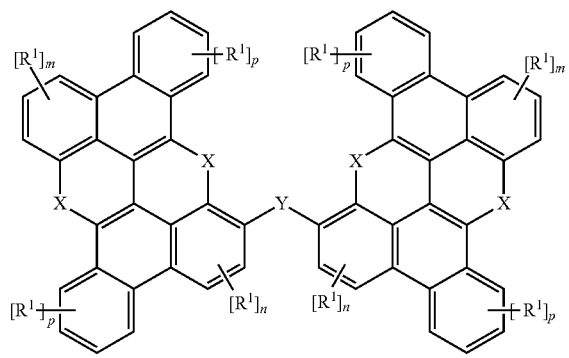
formula (24)
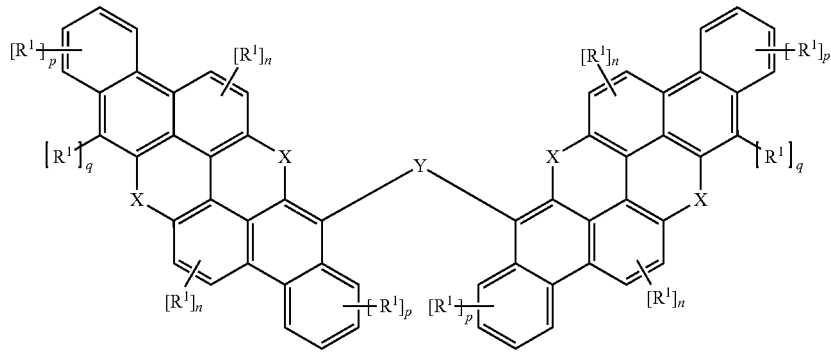
where R, $R^1$, $R^2$, Ar, X, Y, m, n, p and q have the same meaning as described above.

Preference is furthermore given to compounds of the formulae (1) to (8) in which the indices m, n, p and q stand for 0, 1 or 2, particularly preferably for 0 or 1.
In a particularly preferred embodiment, the structures of the formulae (1) to (8) are selected from the formulae (9a) to (24a):
formula (9a)
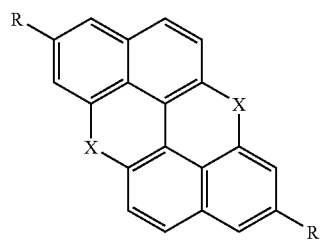
formula (10a)
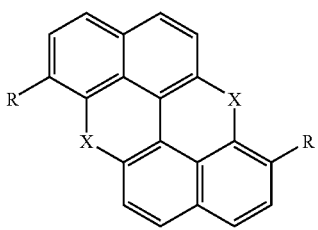
formula (11a)
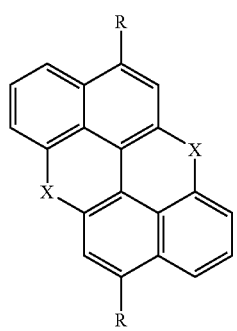
formula (12a)
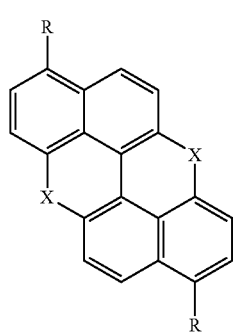
formula (13a)
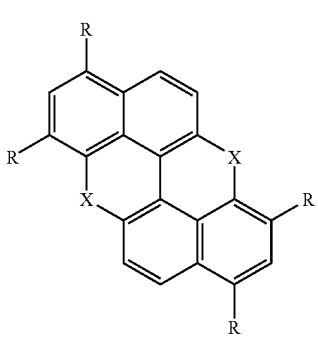
-continued
formula (14a)
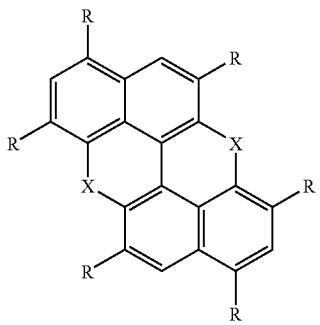
formula (15a)
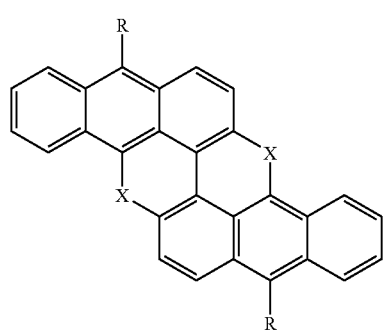
formula (16a)
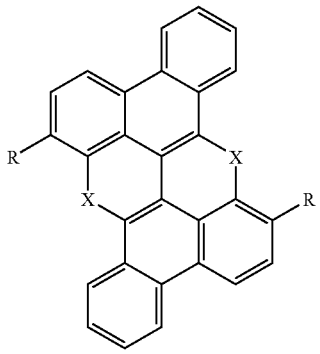
formula (17a)
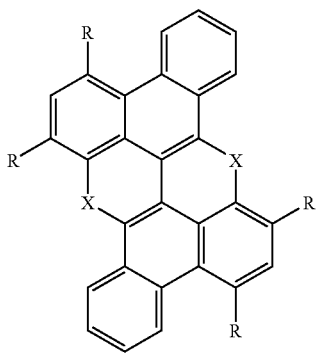

formula (18a)

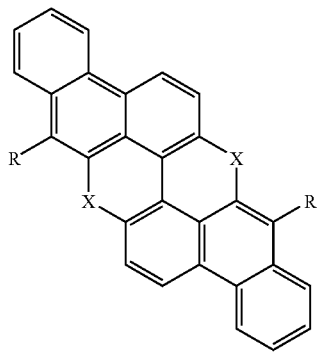

formula (19a)

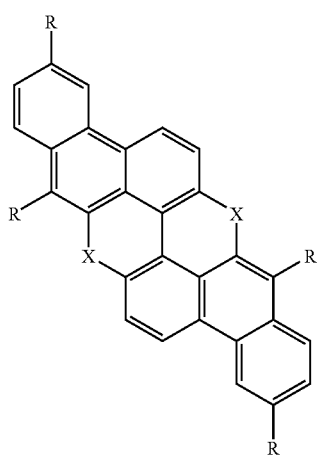

formula (20a)

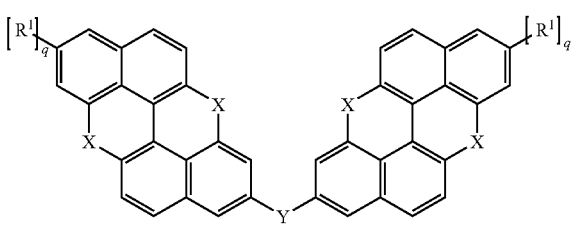

formula (21a)

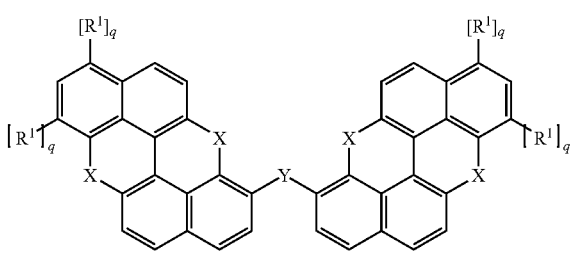

formula (22a)

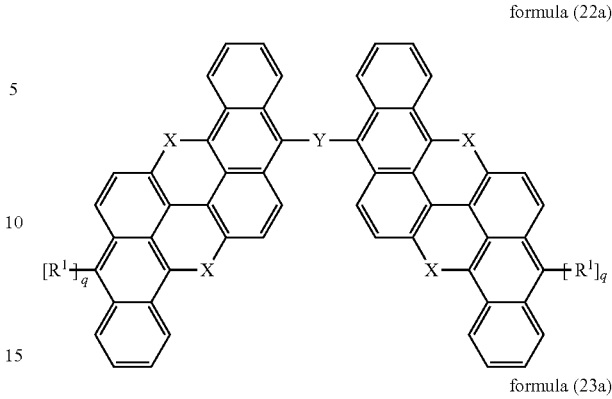

formula (23a)

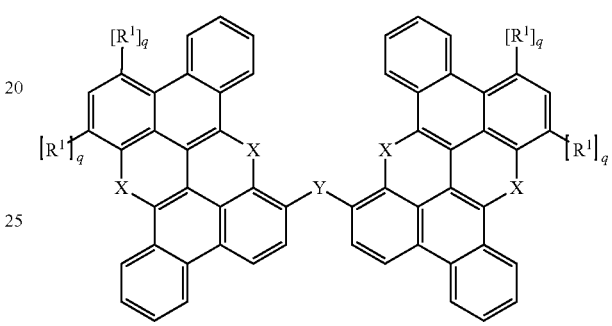

formula (24a)

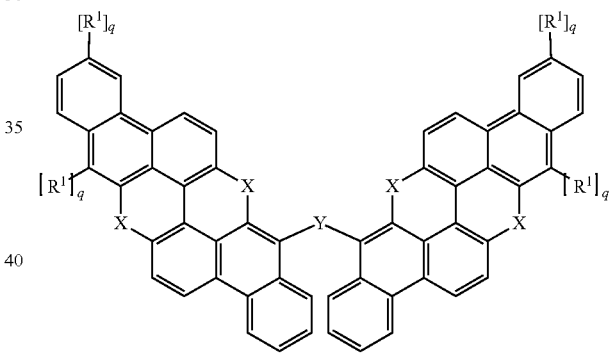

where R, $R^1$, Ar, X, Y and q have the same meaning as described above.

Preference is furthermore given to compounds of the formulae (1) to (8) in which the symbol X stands for O, S or $C(R^1)_2$, particularly preferably for O or $C(R^1)_2$. If the symbol X stands for a $C(R^1)_2$ group, the two radicals $R^1$ in this group may also form a ring system with one another. Preferred radicals $R^1$ in the $C(R^1)_2$ group are methyl, phenyl, ortho-tolyl, para-tolyl, para-tert-butylphenyl or two phenyl groups, which form a ring system with one another and thus build up a spiro system.

Preference is furthermore given to compounds of the formulae (1) to (4) and (9) to (19) or (9a) to (19a) in which the symbol R, identically or differently on each occurrence, stands for an $N(Ar)_2$, C(=O)Ar, P(=O)$Ar_2$, group, a straight-chain alkyl group having 1 to 4 C atoms or a branched alkyl group having 3 to 5 C atoms or an aromatic or heteroaromatic ring system having 5 to 25 aromatic ring atoms, which may be substituted by one or more non-aromatic radicals $R^1$.

Particular preference is given to compounds of the formulae (1) to (4) and (9) to (19) or (9a) to (19a) in which the symbol R, identically or differently on each occurrence, stands for an N(Ar)$_2$, C(=O)Ar group or an aromatic ring system having 6 to 20 aromatic ring atoms, which may be substituted by one or more non-aromatic radicals R$^1$.

If the symbol R stands for an N(Ar)$_2$ group, it preferably stands for a group of the following formula (25) or (26):

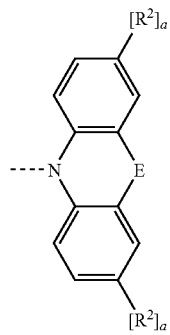

formula (25)

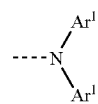

formula (26)

where R$^2$ has the meaning indicated above, and furthermore:
E stands for a single bond, O, S, N(R$^2$) or C(R$^2$)$_2$;
Ar$^1$ is, identically or differently on each occurrence, an aryl or heteroaryl group having 5 to 20 aromatic ring atoms or a triarylamine group having 15 to 30 aromatic ring atoms, each of which may be substituted by one or more radicals R$^2$, preferably an aryl or heteroaryl group having 6 to 14 aromatic ring atoms or a triarylamine group having 18 to 22 aromatic ring atoms, each of which may be substituted by one or more radicals R$^2$;

a is on each occurrence, identically or differently, 0 or 1.

Ar$^1$ particularly preferably stands, identically or differently, for phenyl, 1-naphthyl, 2-naphthyl, triphenylamine, naphthyldiphenylamine or dinaphthylphenylamine, each of which may be substituted by one or more alkyl groups having 1 to 4 C atoms or by fluorine.

Preference is furthermore given to compounds of the formulae (5) to (8) and (20) to (24) or (20a) to (24a) in which the symbol Y stands for a C(=O) or N(Ar) group or for a divalent aryl group having 6 to 16 C atoms, which may be substituted by one or more non-aromatic radicals R$^1$.

Preference is furthermore given to compounds of the formulae (5) to (8) and (20) to (24) or (10a) to (24a) in which the symbol R$^1$ has the same meaning as R and in which, in particular, the same preference as described above for R also applies.

Preference is furthermore given to compounds of the formulae (1) to (24) or (9a) to (24a) which have a symmetrical structure with respect to the substituents present, in particular structures which have at least one twofold axis of rotation. In the structures of the formulae (9a) to (19a), all radicals R within a compound are particularly preferably selected identically. In the structures of the formulae (20a) to (24a), all radicals R$^1$ within a compound are furthermore particularly preferably selected identically.

Examples of preferred compounds according to the invention are structures (1) to (182) depicted below.

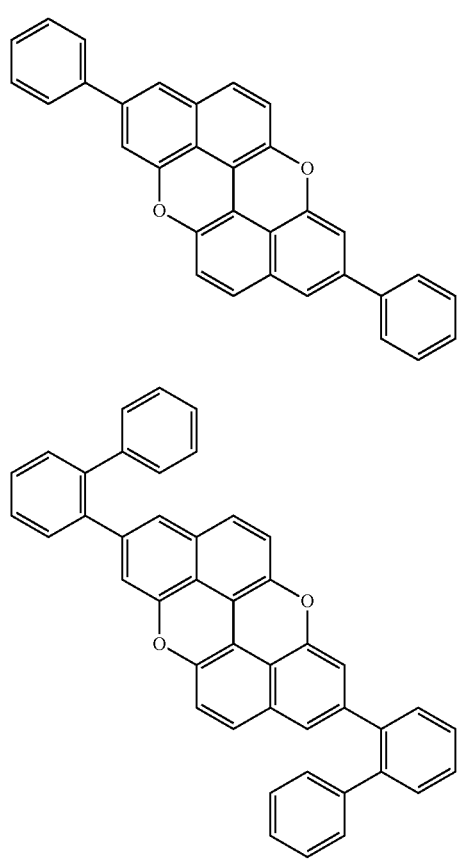

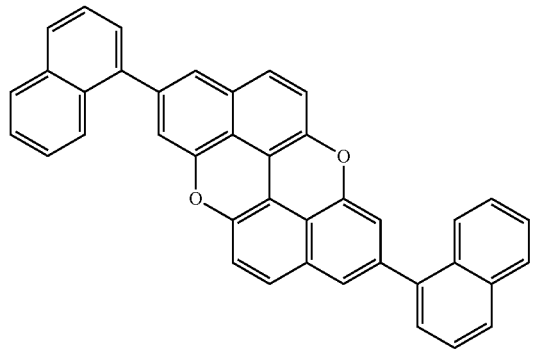

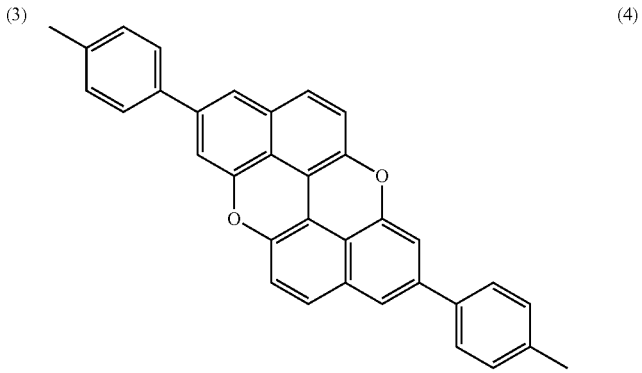

-continued
(5)
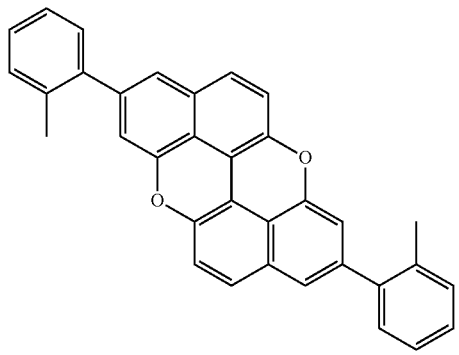
(6)
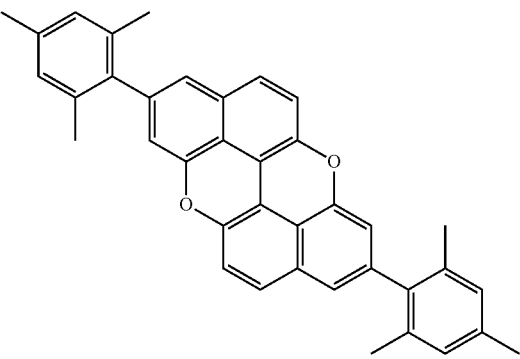
(7)
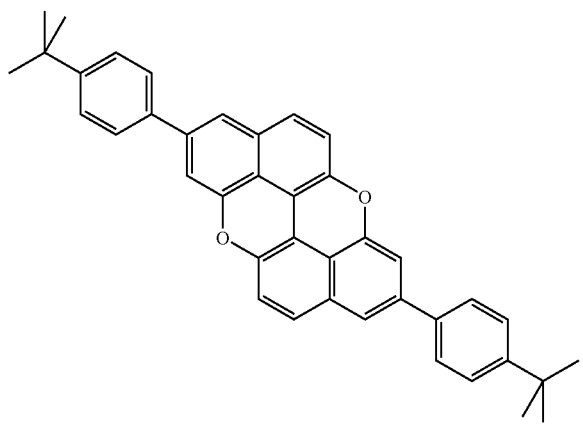
(8)
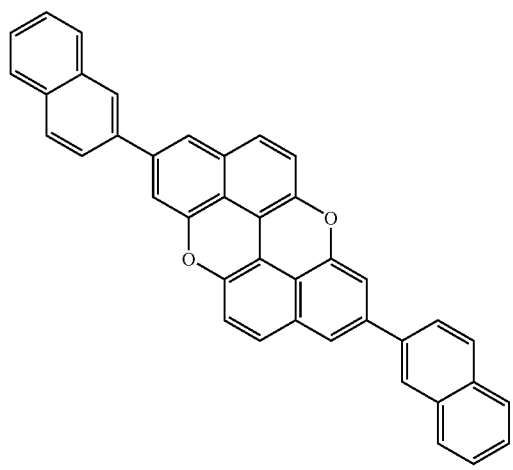
(9)
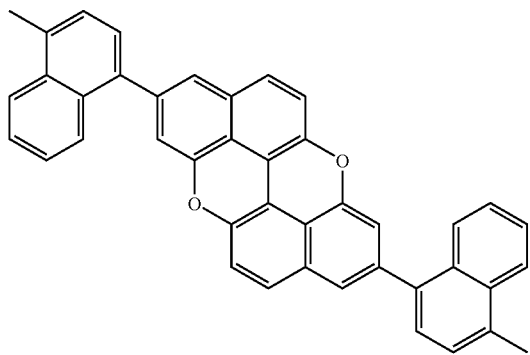
(10)
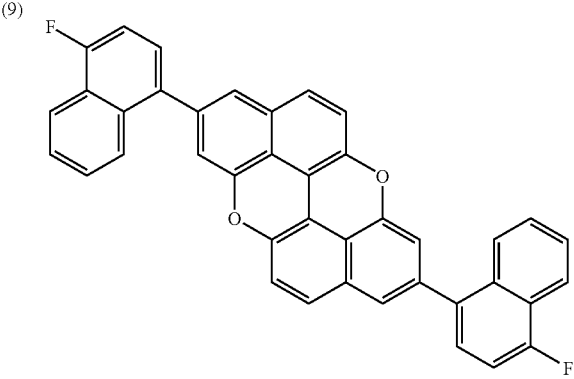

-continued
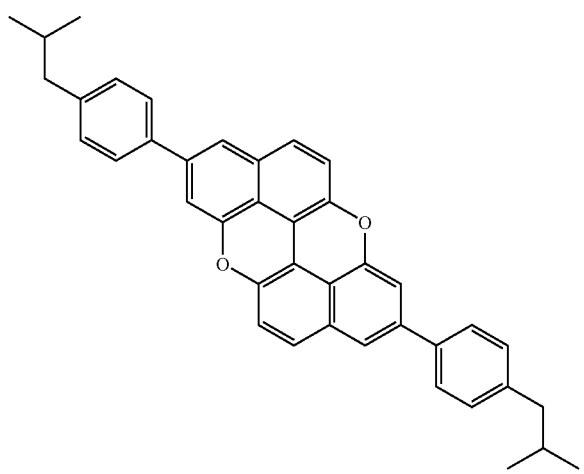
(11)
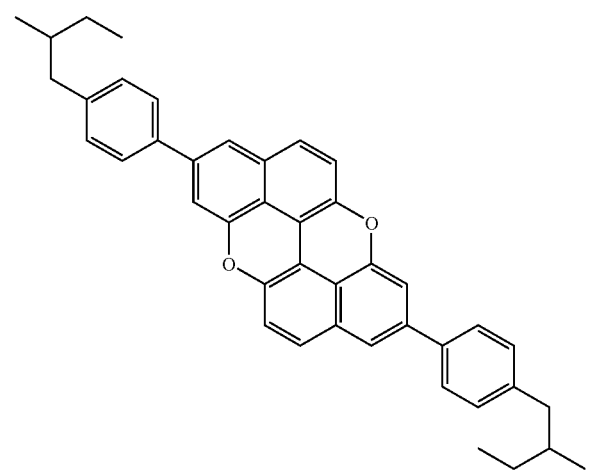
(12)
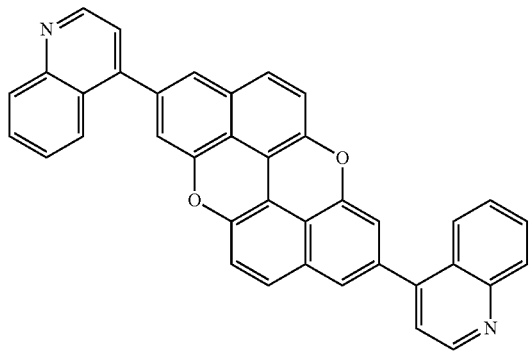
(13)
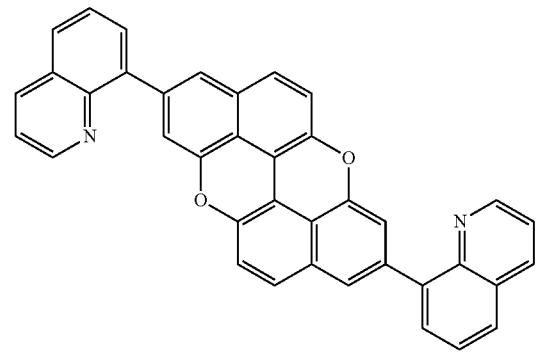
(14)
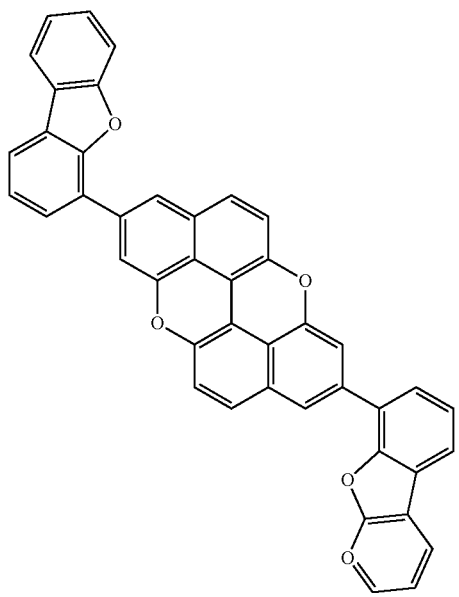
(15)
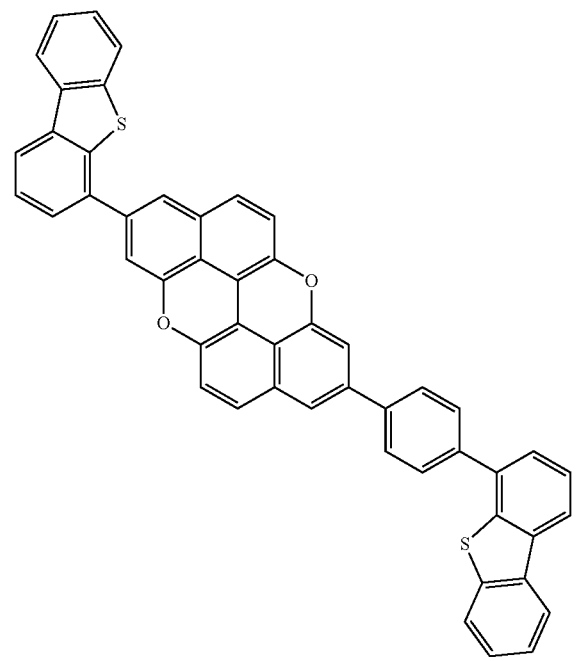
(16)

-continued
(17)
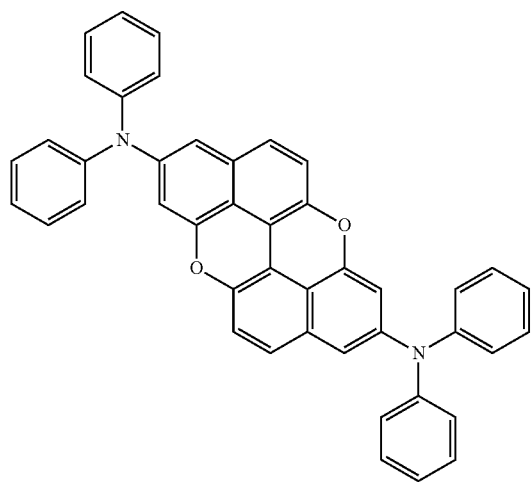
(18)
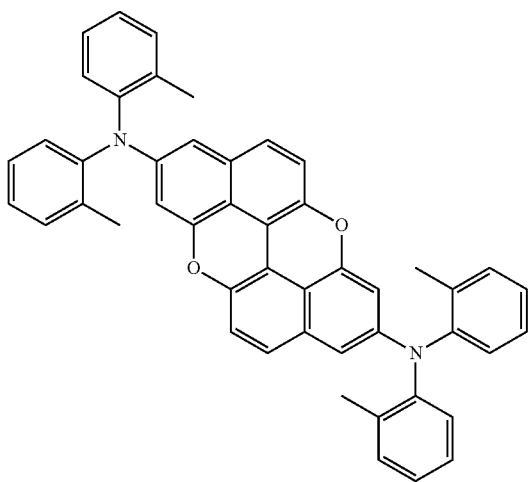
(19)
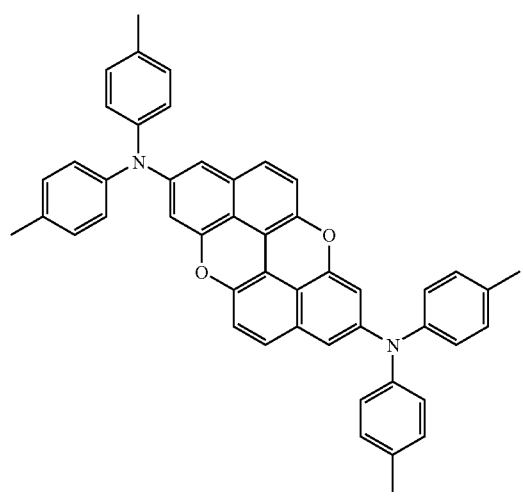
(20)
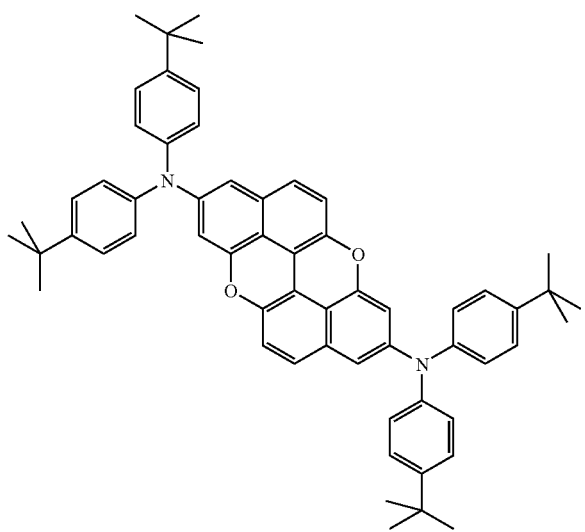
(21)
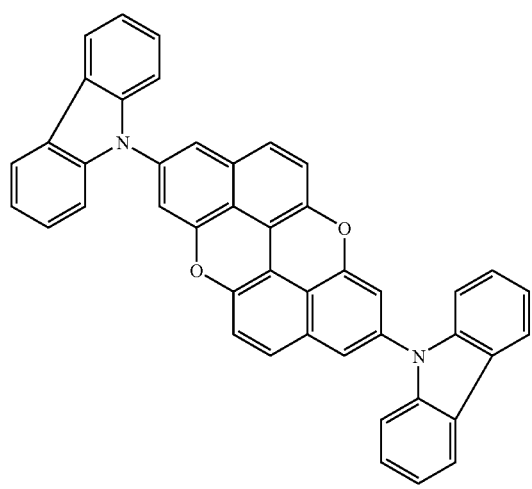
(22)
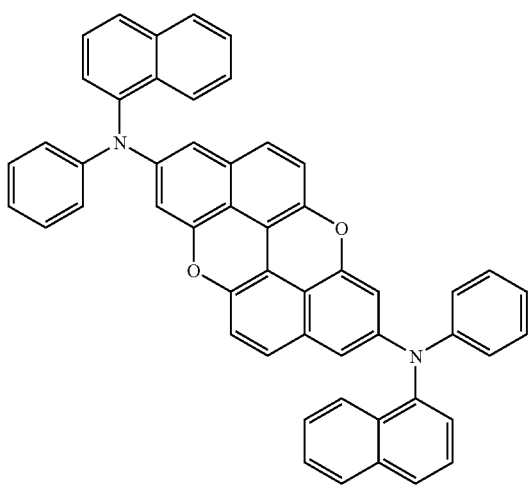

-continued
(23)
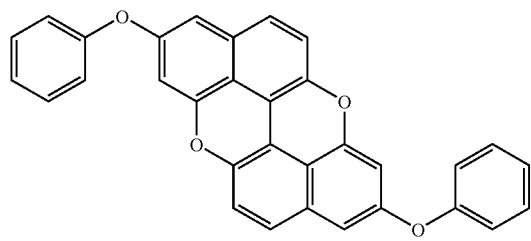
(24)
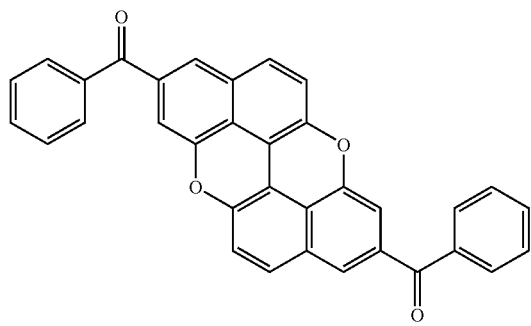
(25)
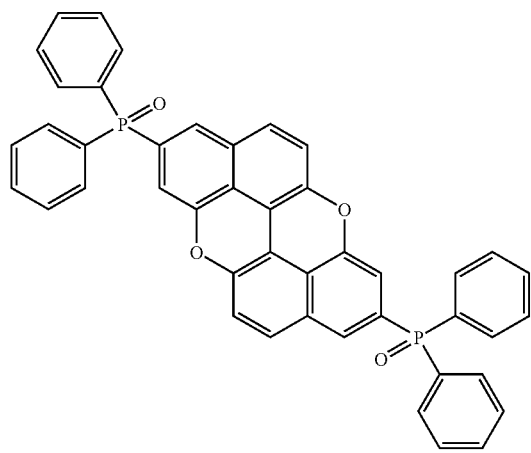
(26)
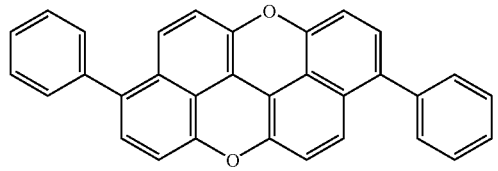
(27)
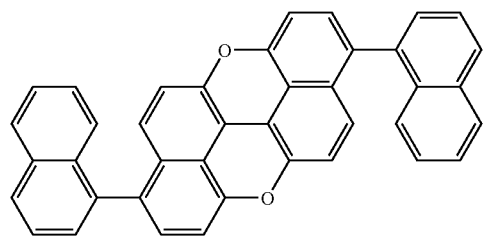
(28)
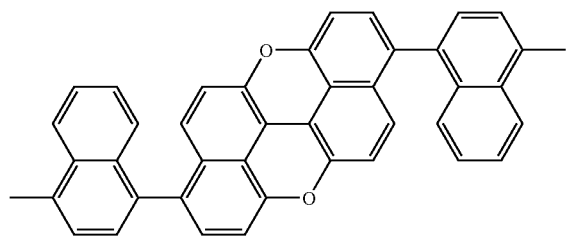
(29)
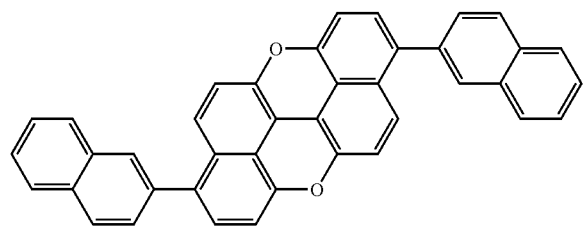
(30)
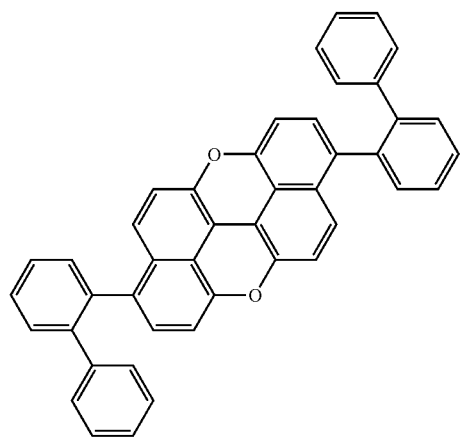

-continued
(31)
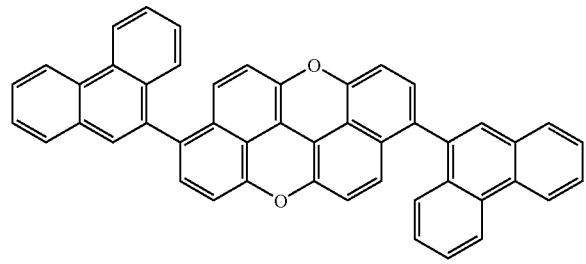
(32)
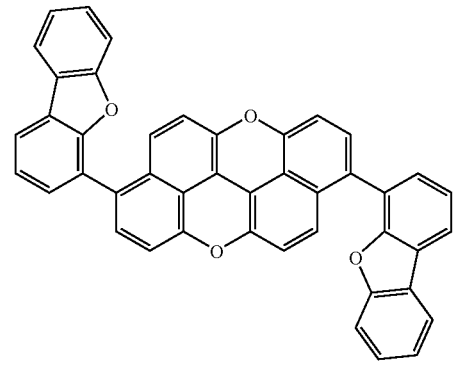
(33)
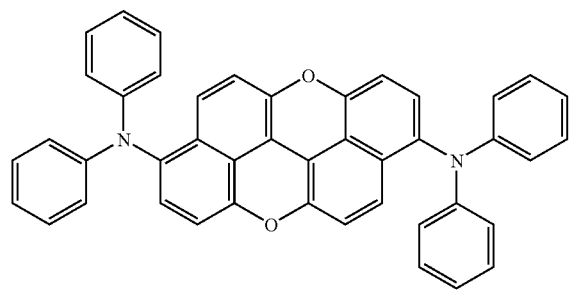
(34)
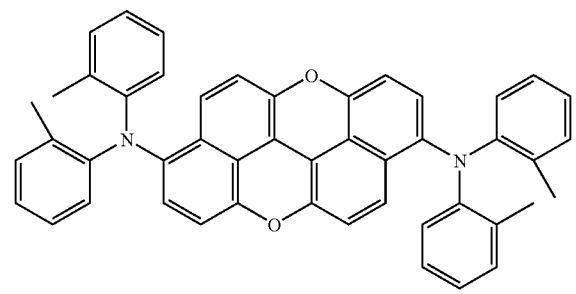
(35)
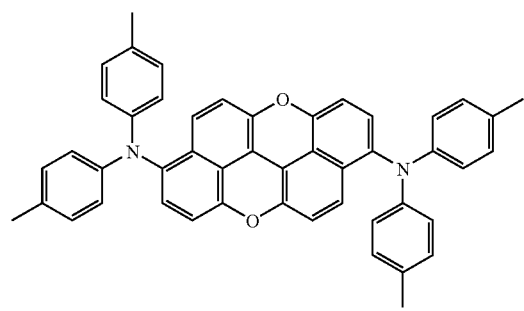
(36)
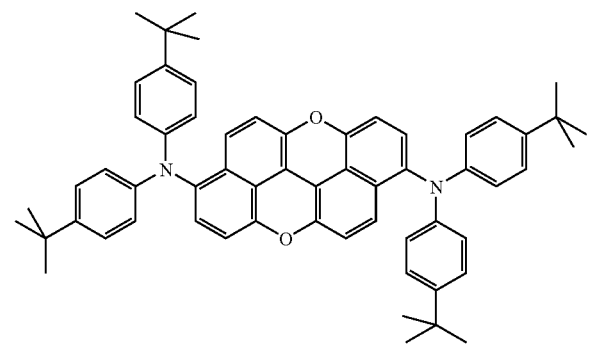
(37)
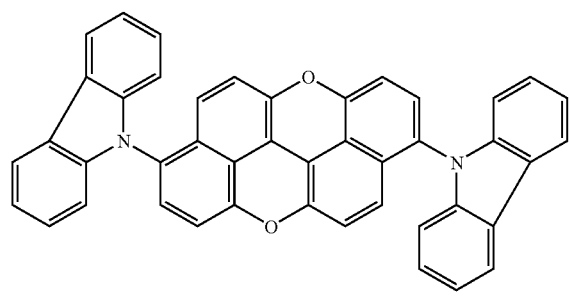
(38)
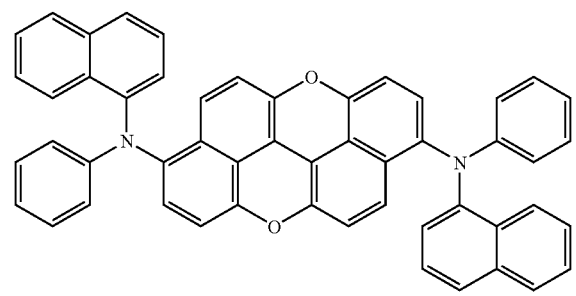

-continued
(39)
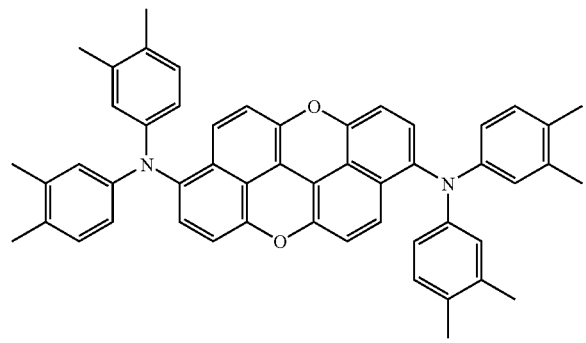
(40)
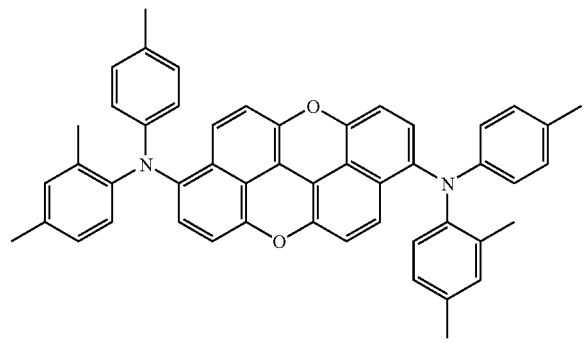
(41)
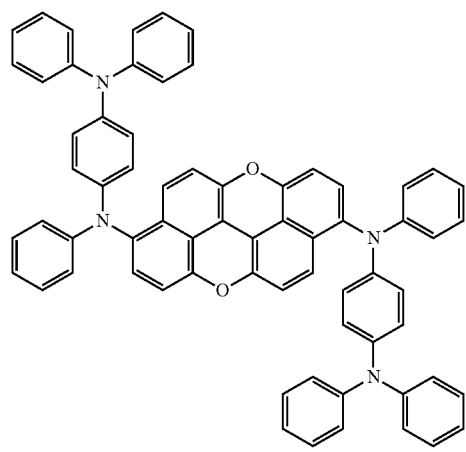
(42)
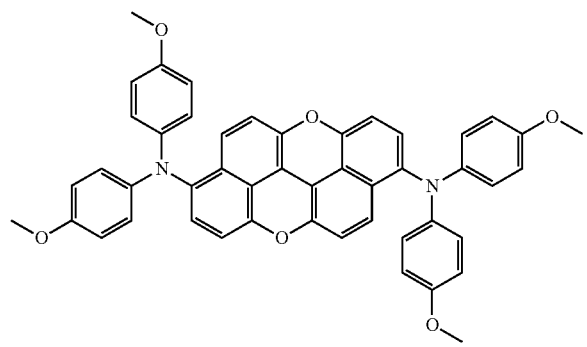
(43)
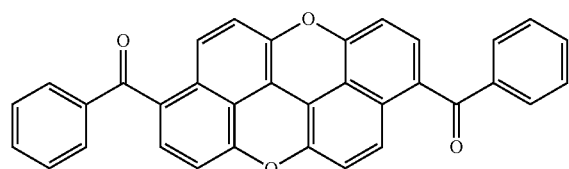
(44)
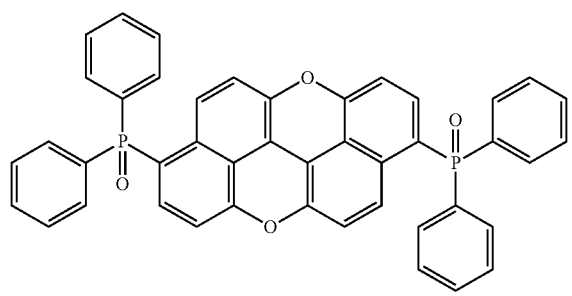

-continued
(45)
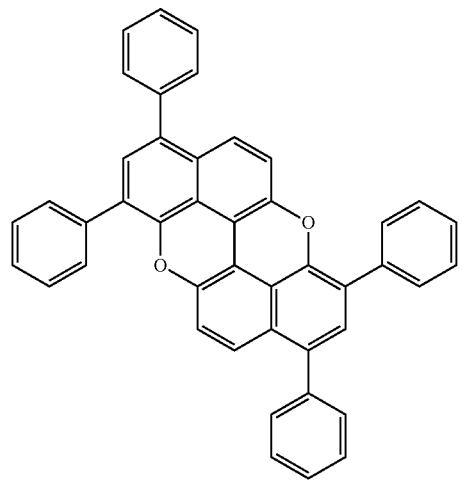
(46)
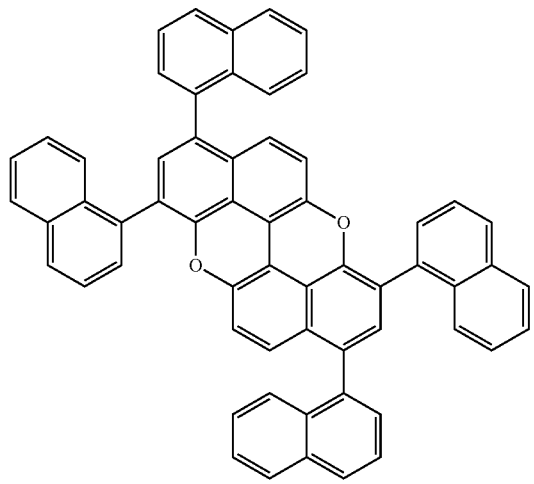
(47)
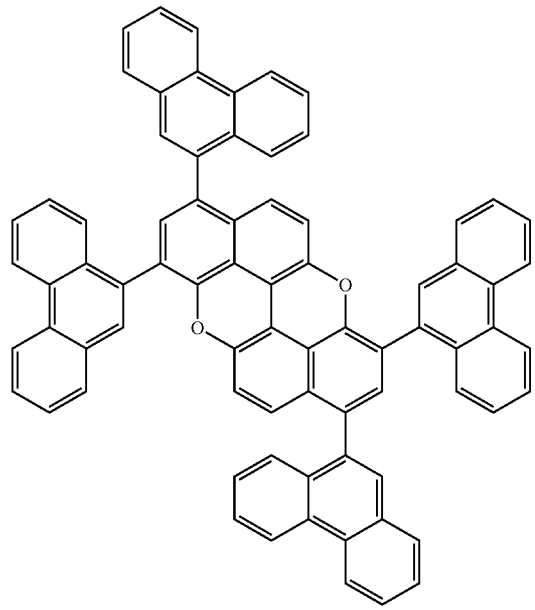
(48)
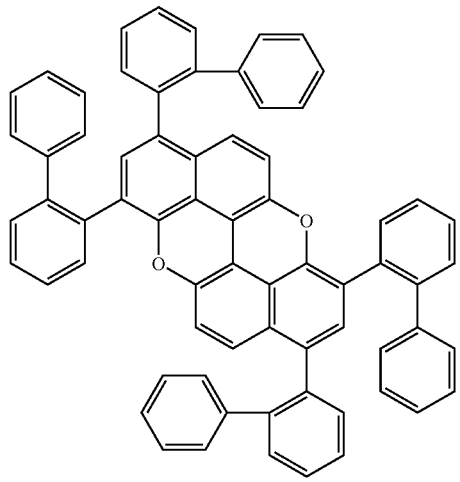
(49)
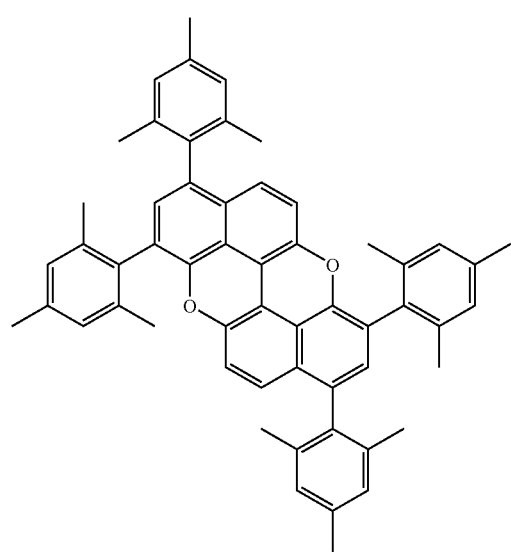
(50)
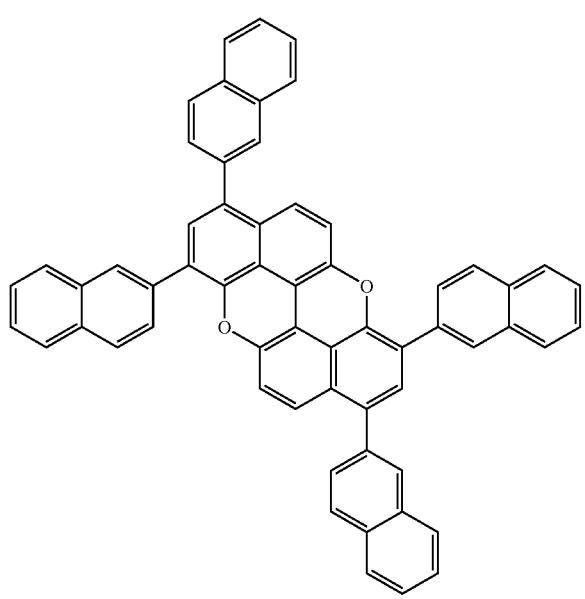

-continued
(51)
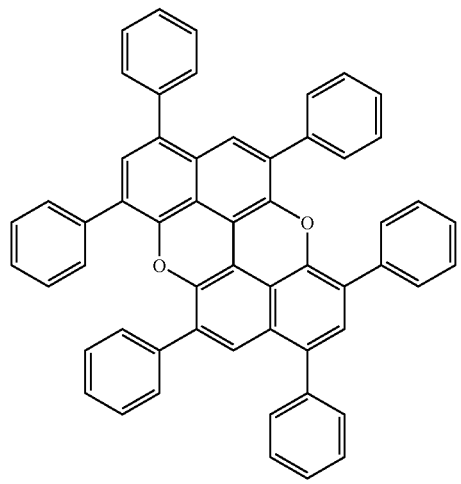
(52)
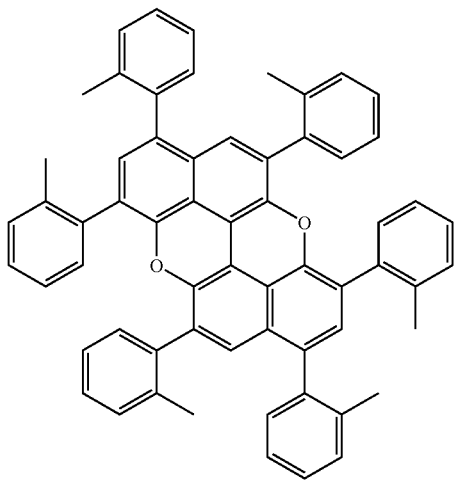
(53)
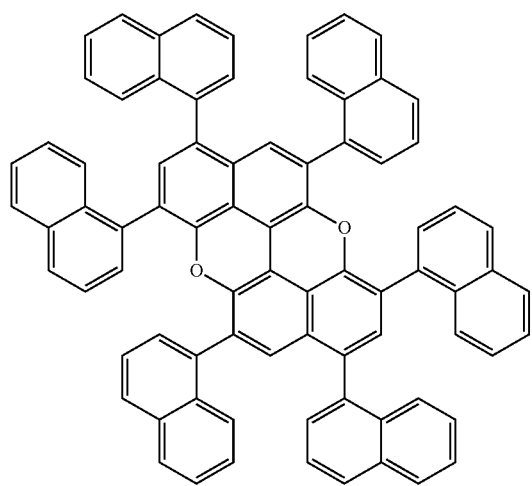
(54)
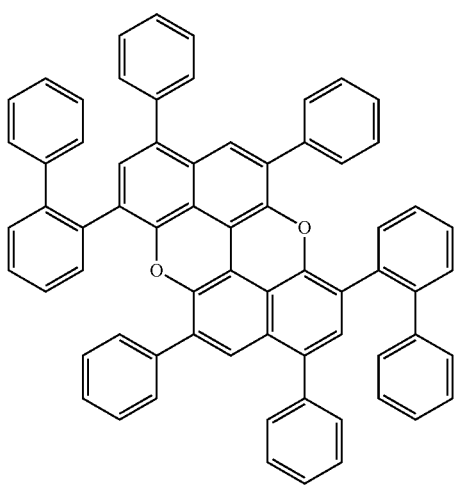
(55)
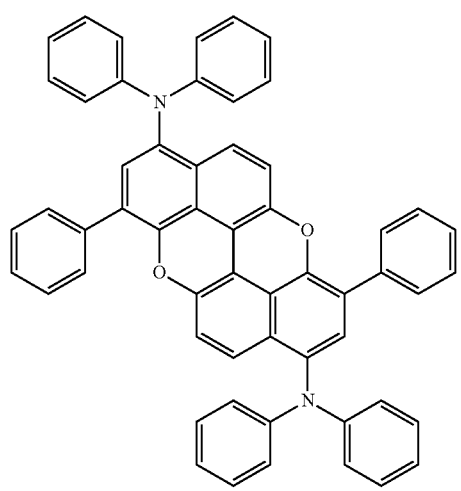
(56)
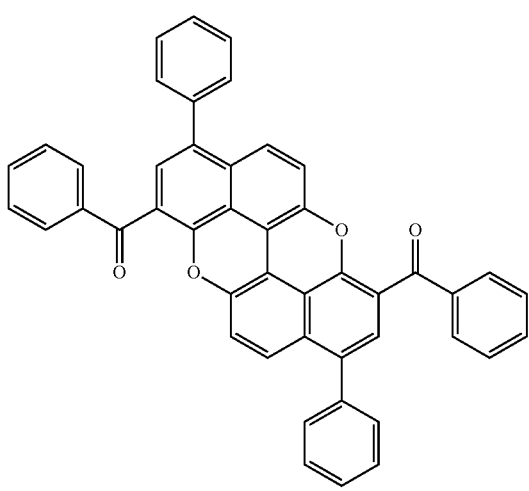

-continued
(57)
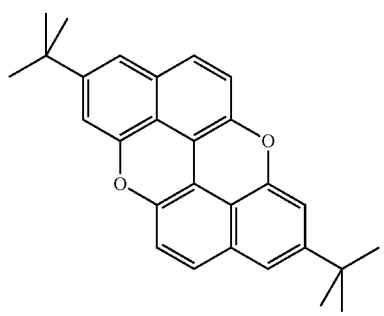
(58)
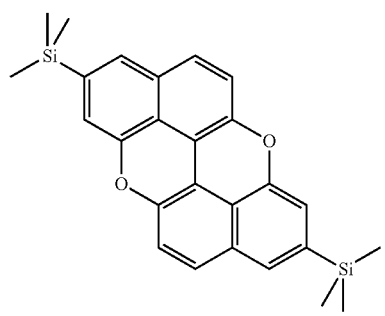
(59)
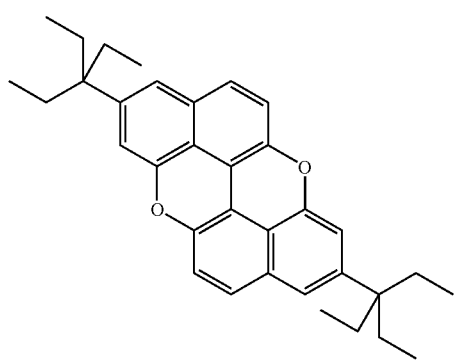
(60)
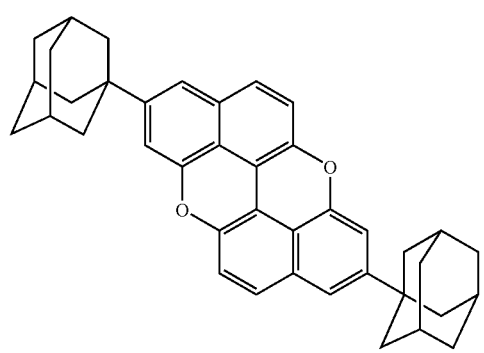
(61)
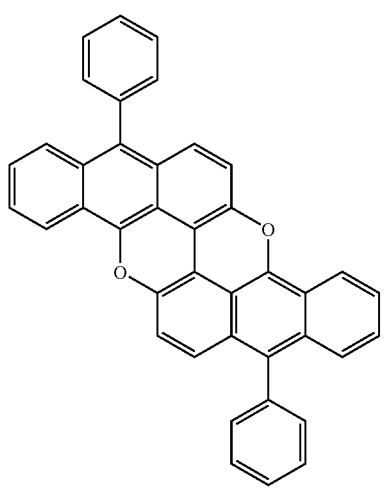
(62)
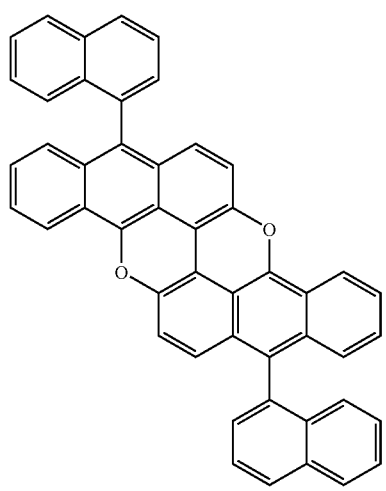

(63)
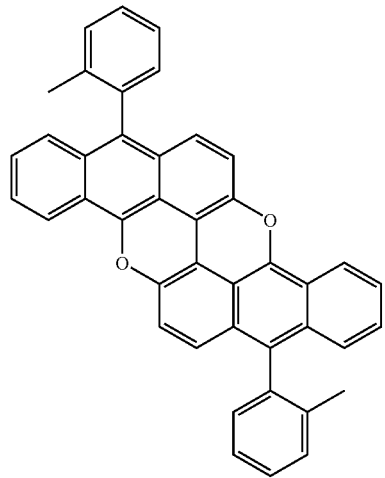
(64)
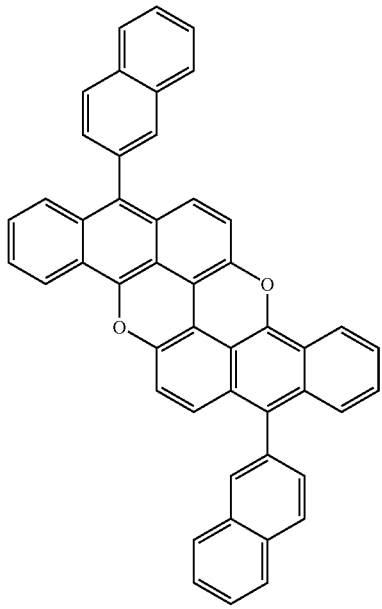
(65)
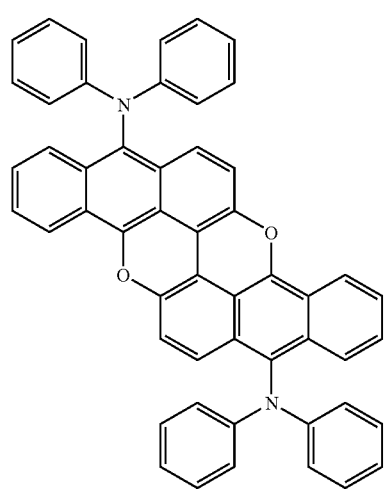
(66)
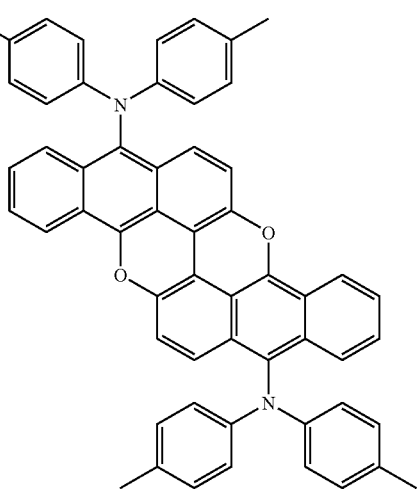

-continued
(67)
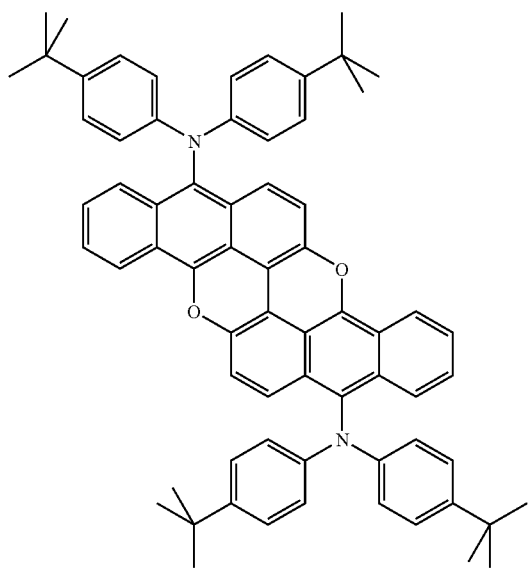
(68)
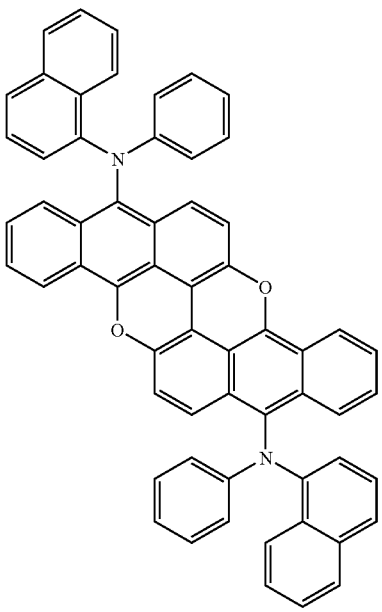
(69)
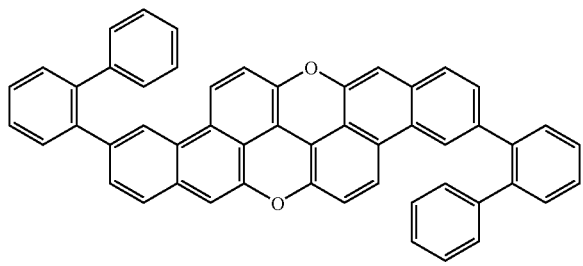
(70)
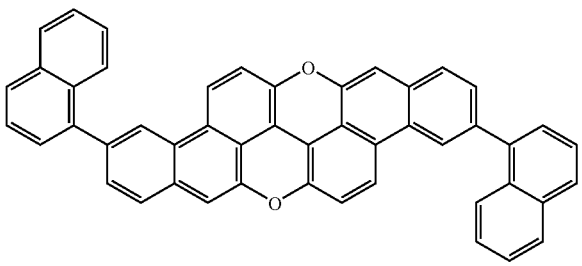
(71)
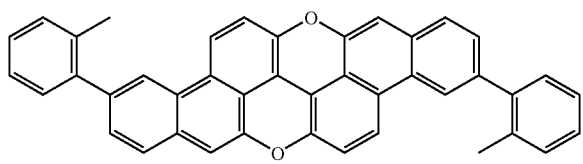
(72)
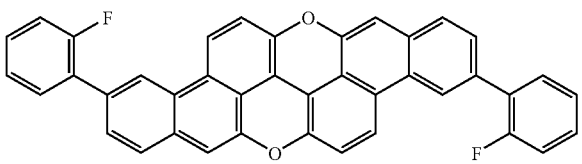
(73)
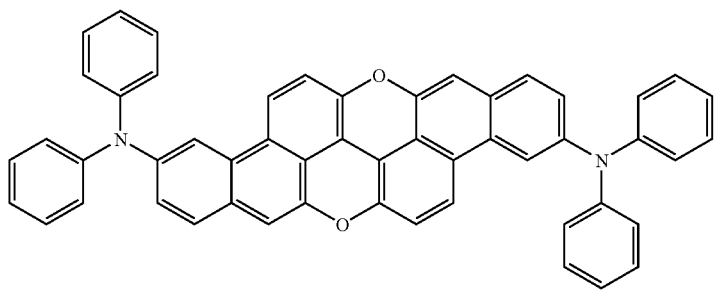

-continued
(74)
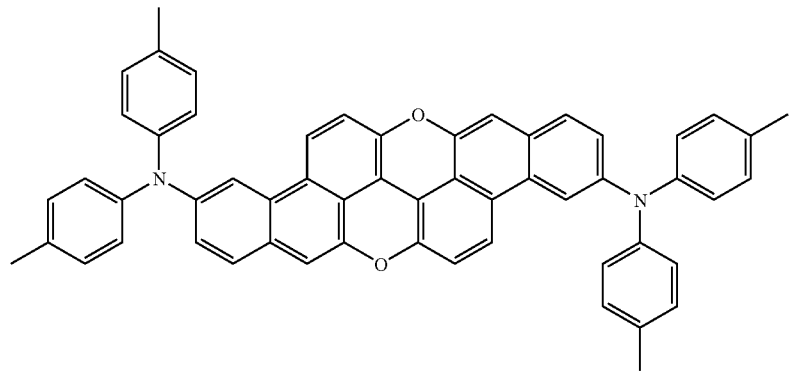
(75)
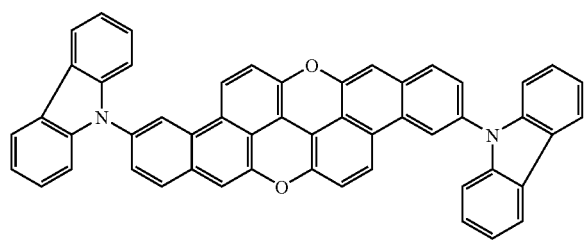
(76)
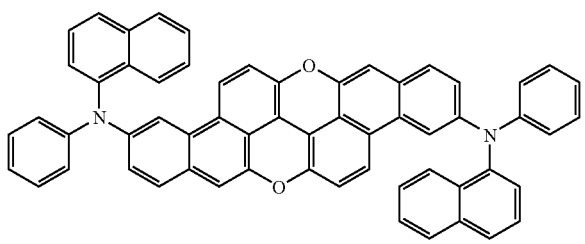
(77)
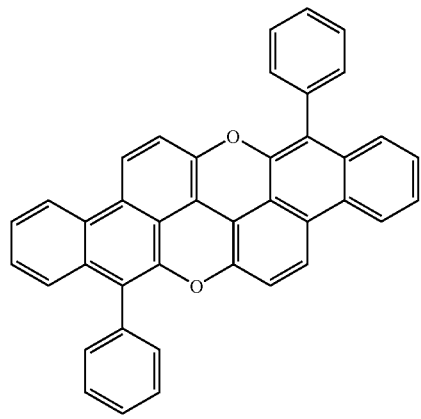
(78)
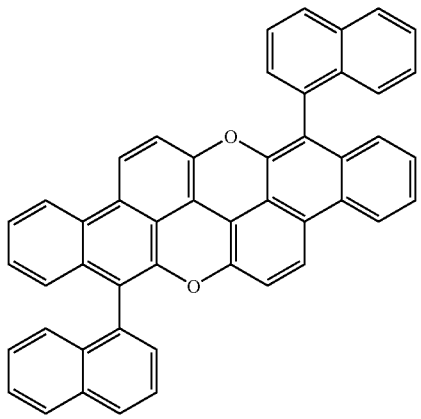
(79)
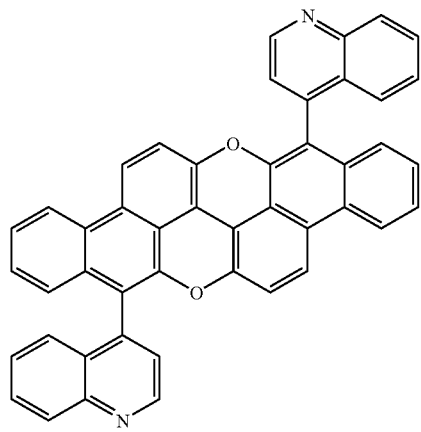
(80)
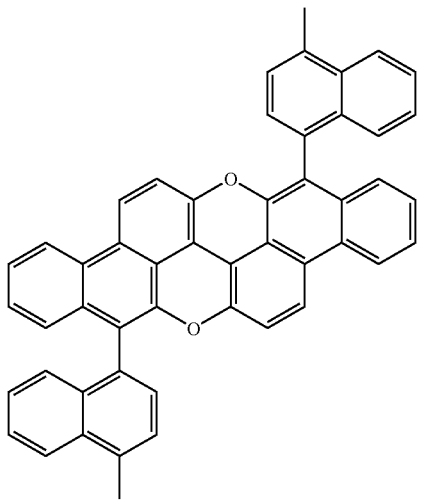

-continued
(81)
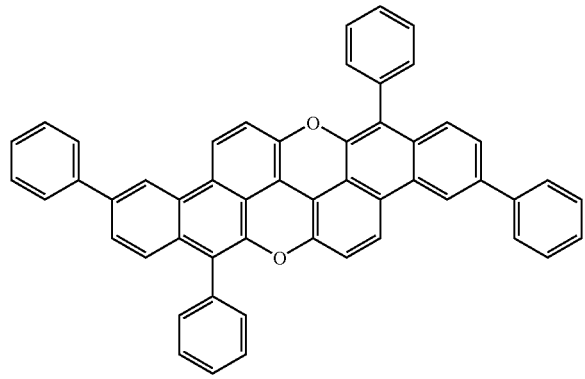
(82)
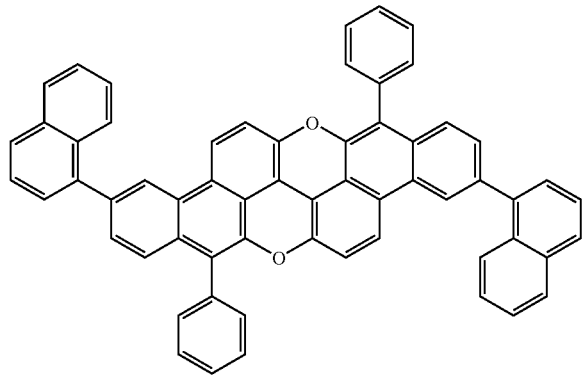
(83)
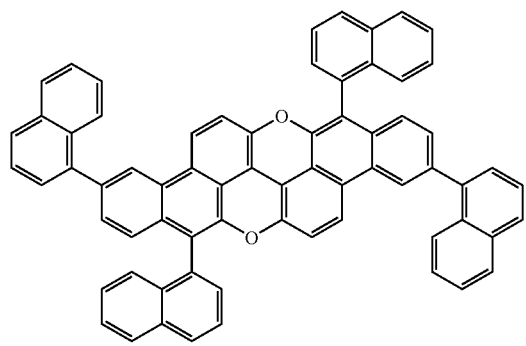
(84)
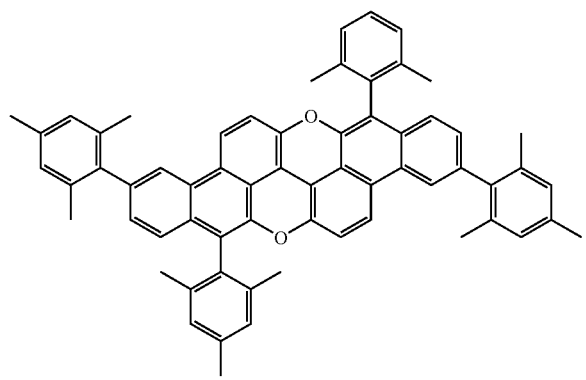
(85)
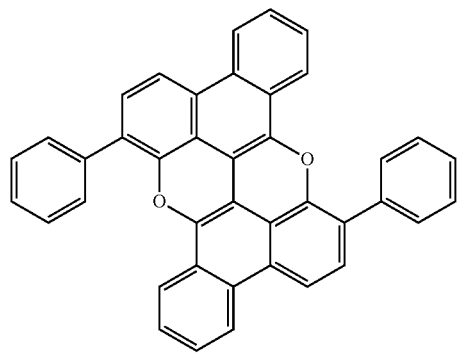
(86)
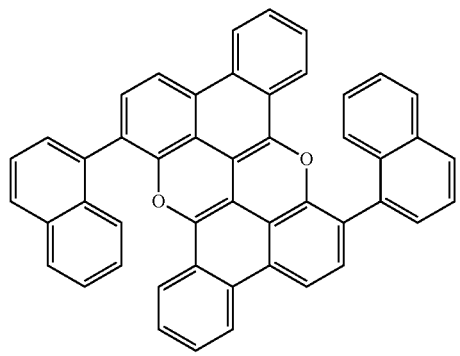
(87)
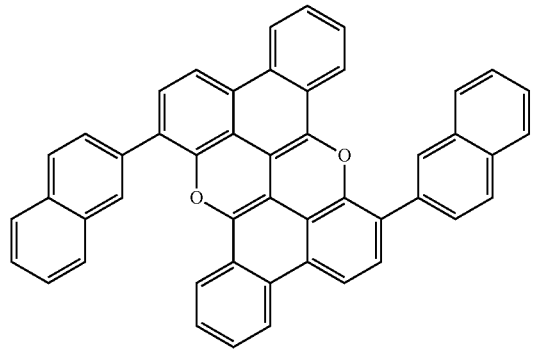
(88)
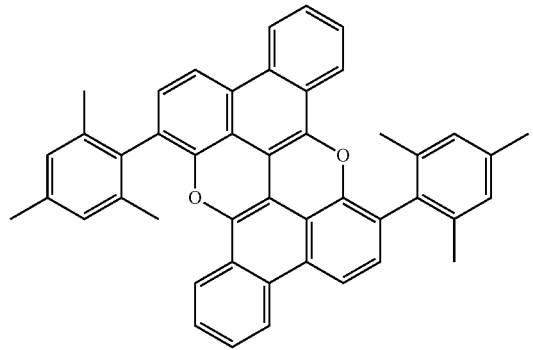

-continued
(89)
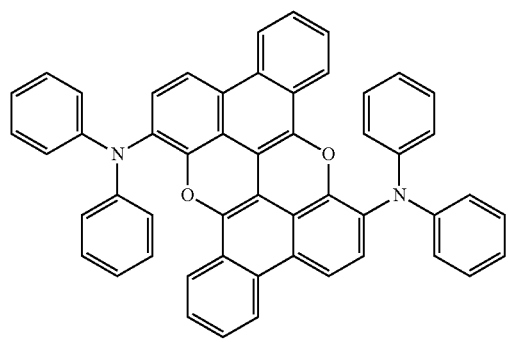
(90)
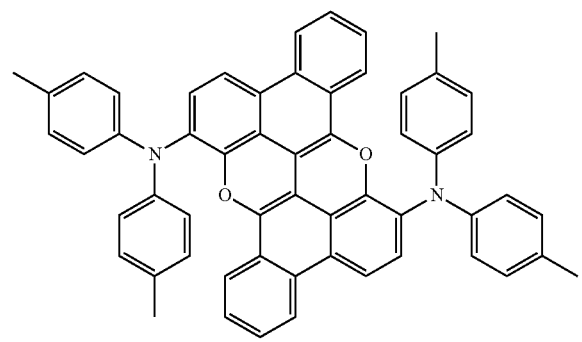
(91)
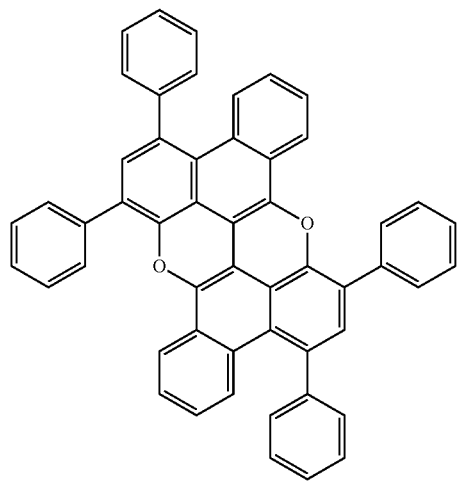
(92)
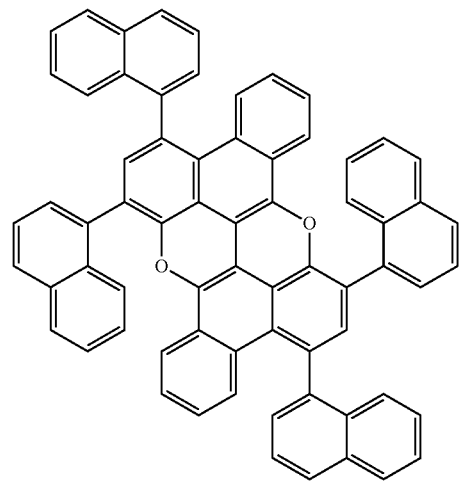
(93)
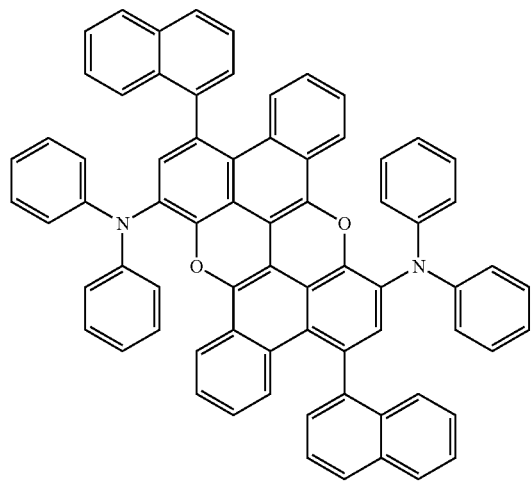
(94)
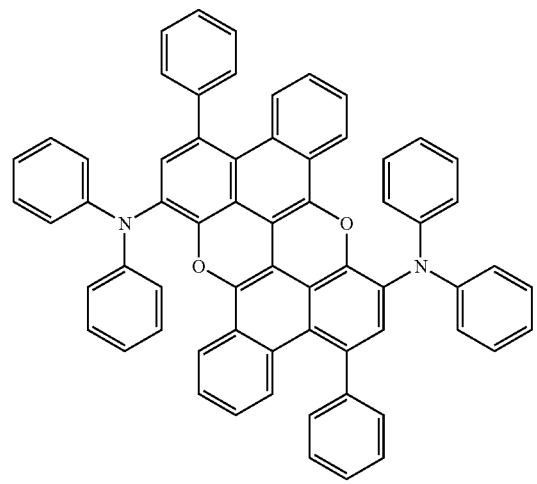

-continued
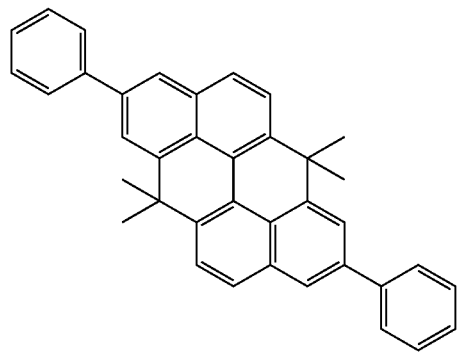
(95)
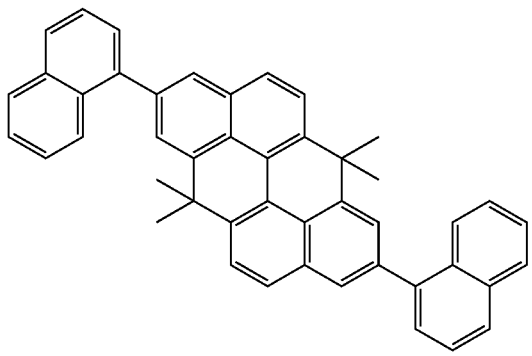
(96)
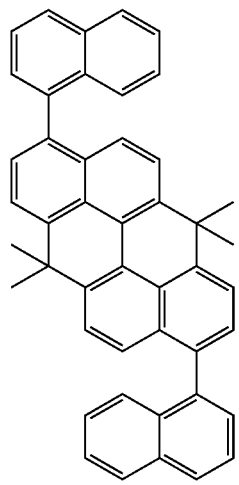
(97)
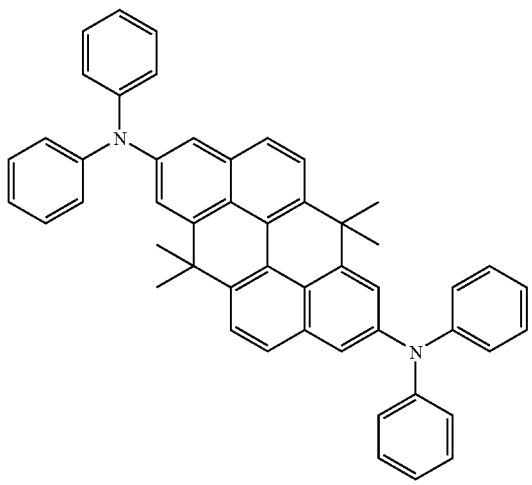
(98)
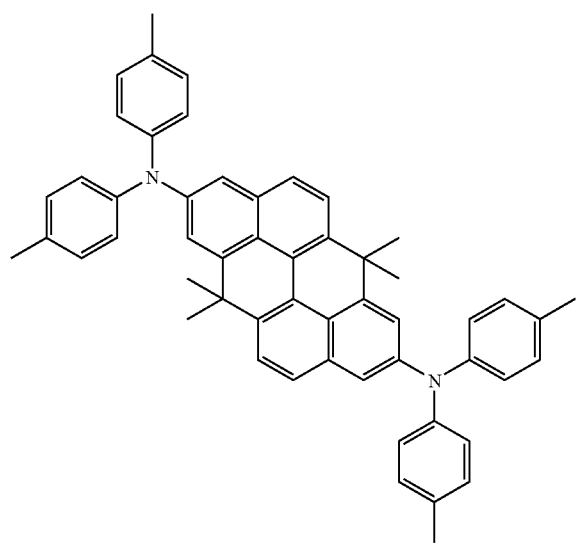
(99)
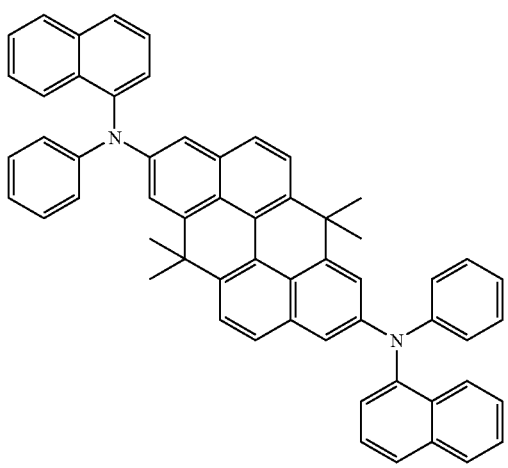
(100)

-continued
(101)
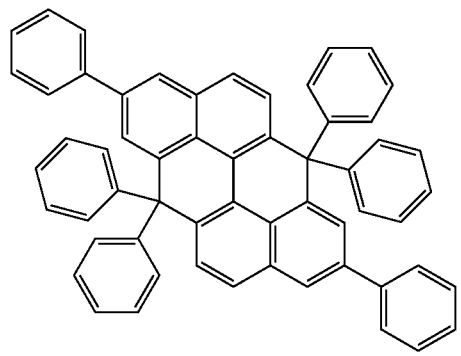
(102)
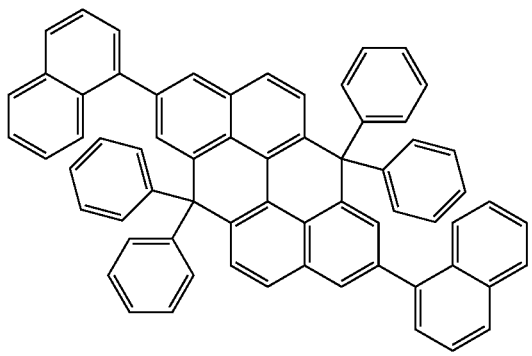
(103)
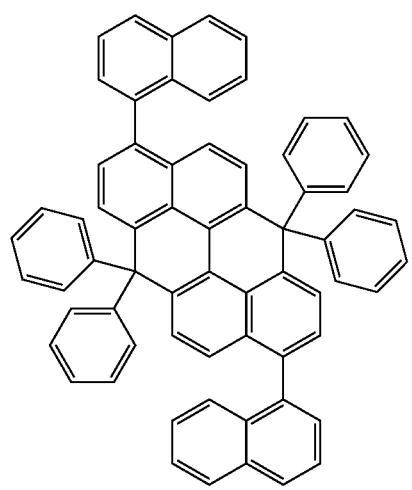
(104)
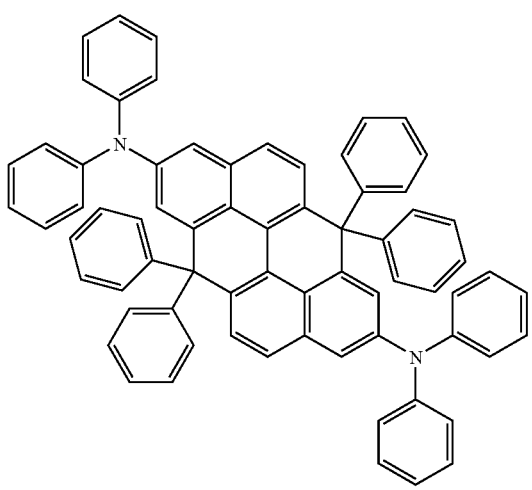
(105)
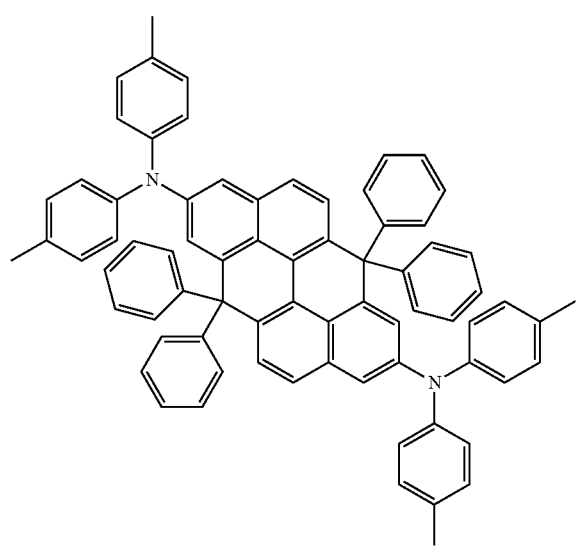
(106)
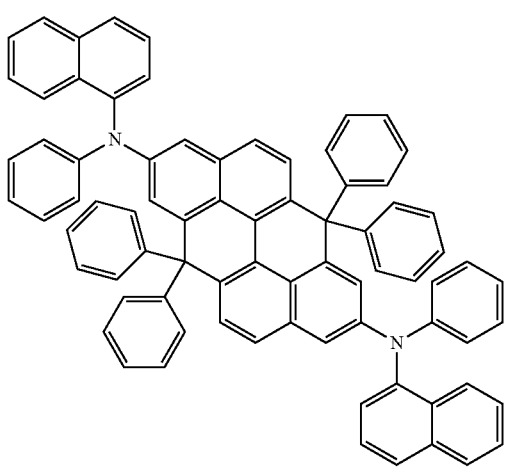

-continued
(107)
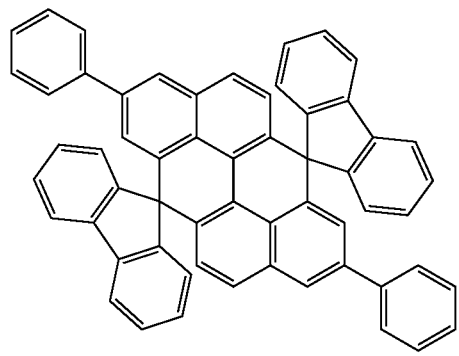
(108)
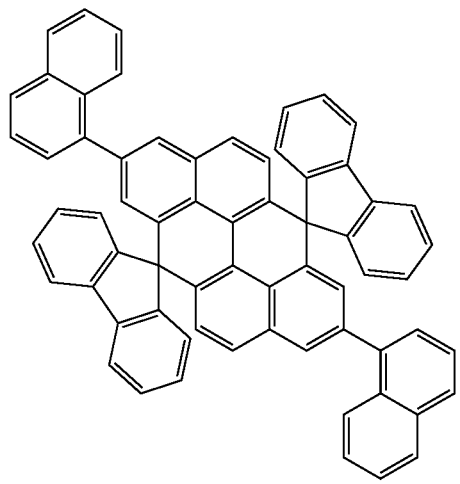
(109)
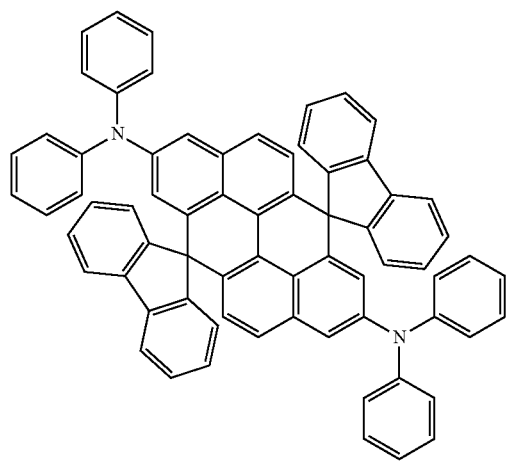
(110)
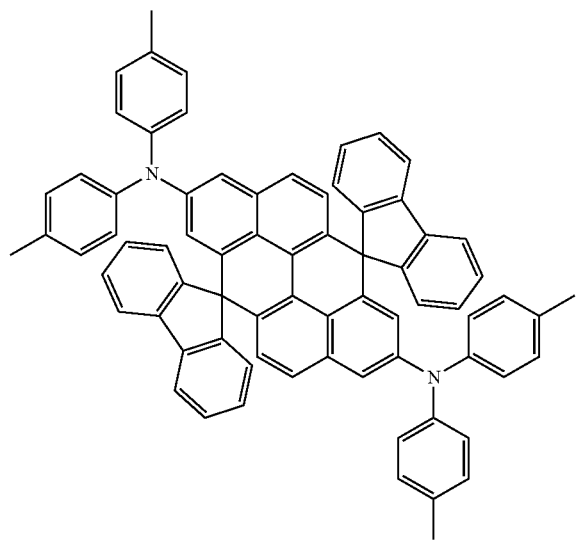
(111)
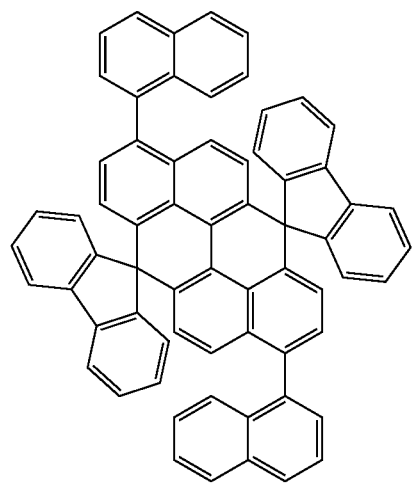
(112)
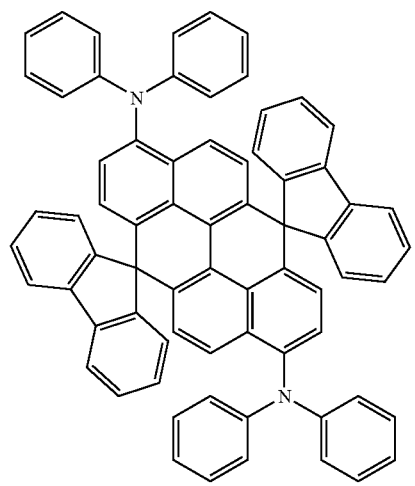

-continued
(113)
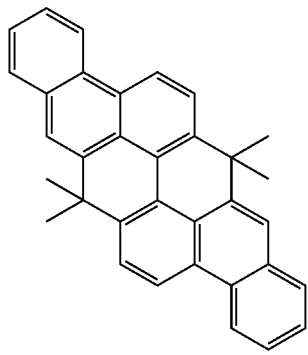
(114)
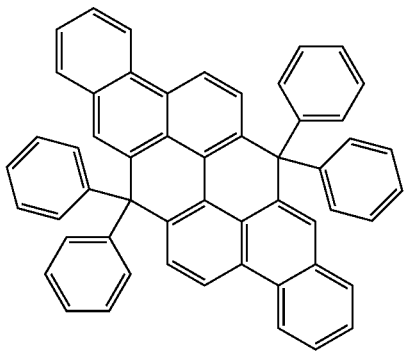
(115)
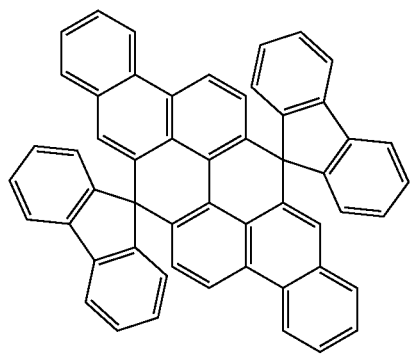
(116)
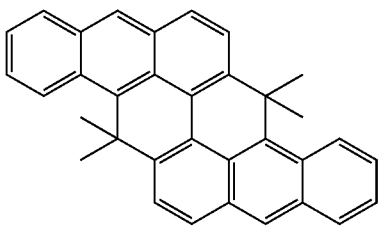
(117)
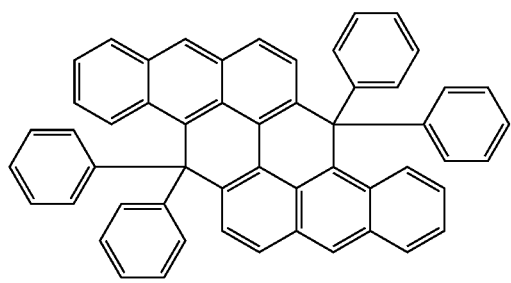
(118)
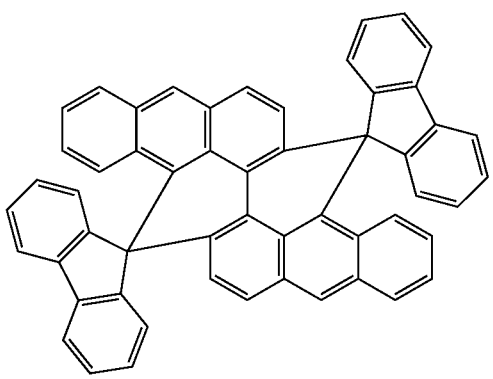
(119)
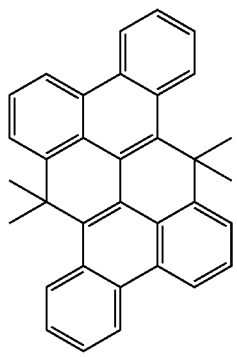
(120)
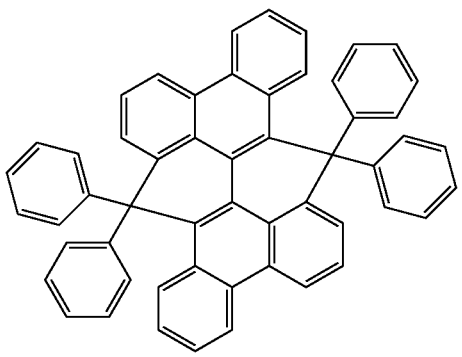

-continued
(121)
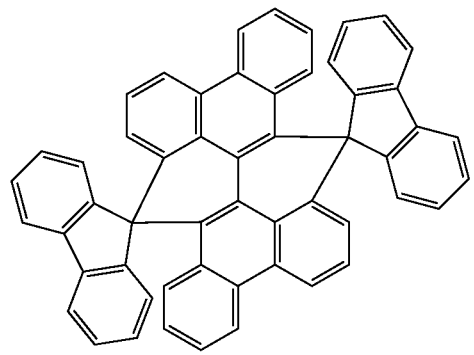
(122)
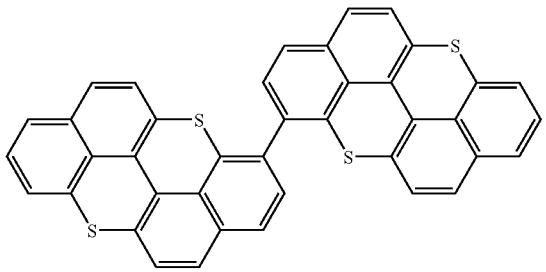
(123)
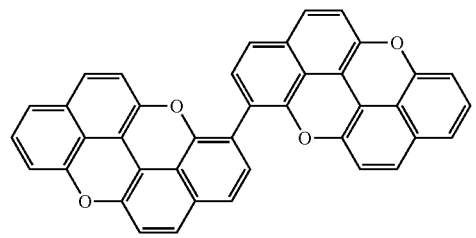
(124)
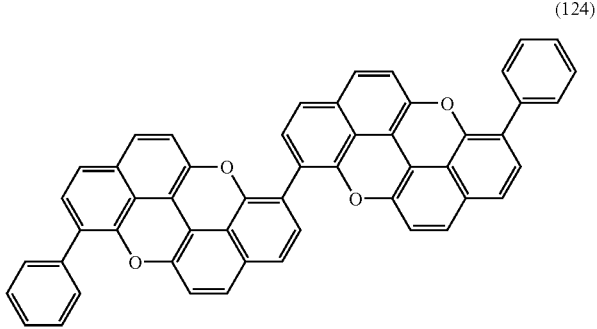
(125)
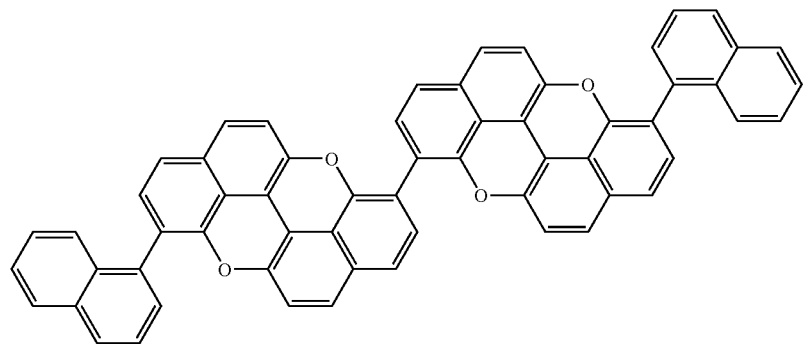
(126)
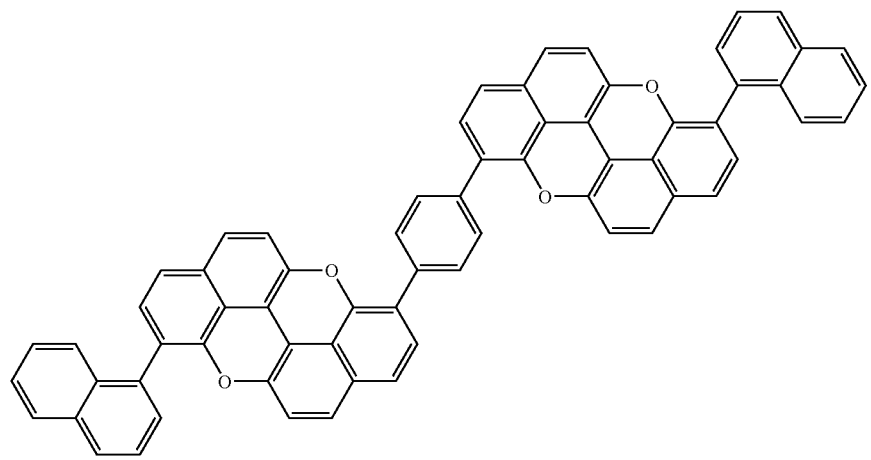

(127)
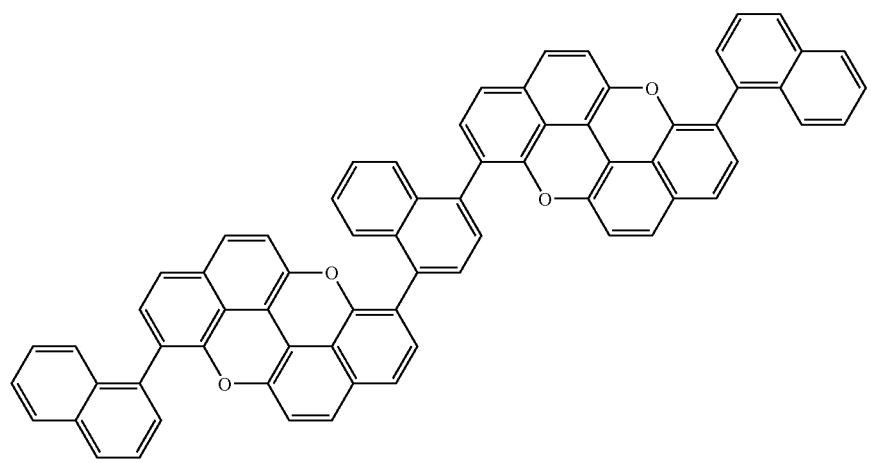
(128)
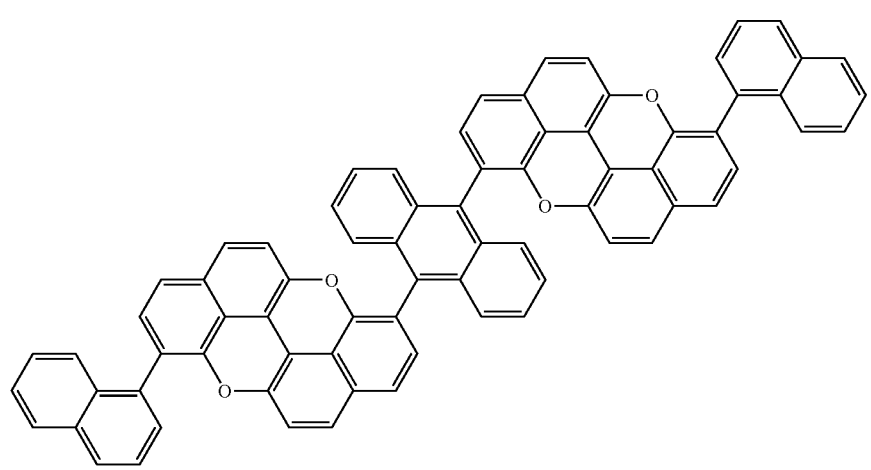
(129)
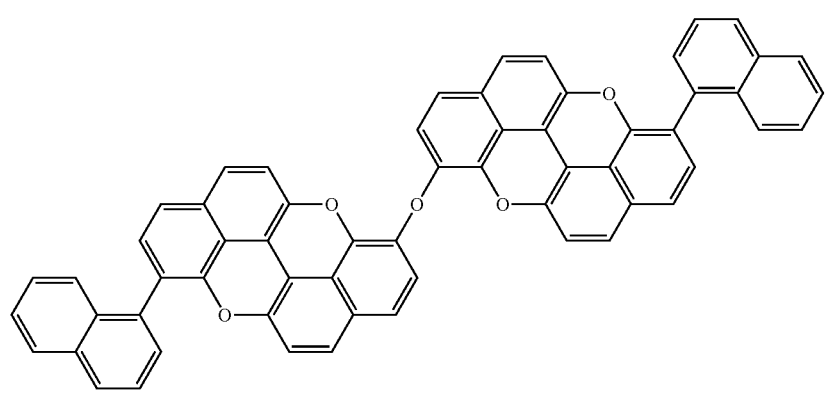
(130)
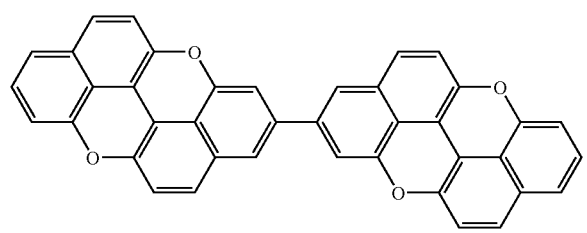
(131)
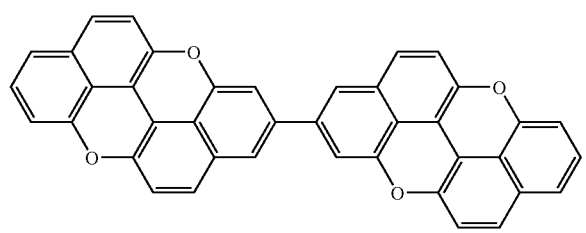

-continued
(132)
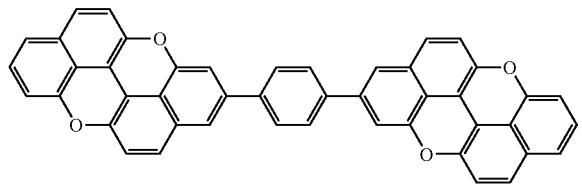
(133)
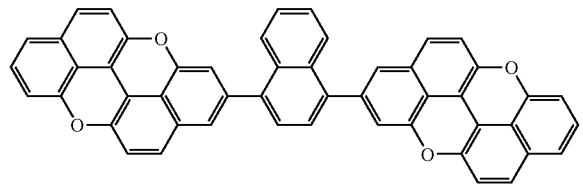
(134)
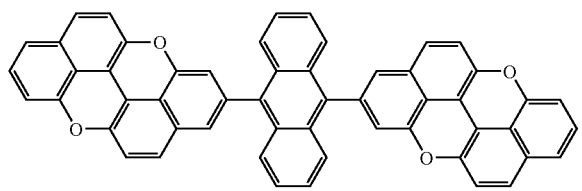
(135)
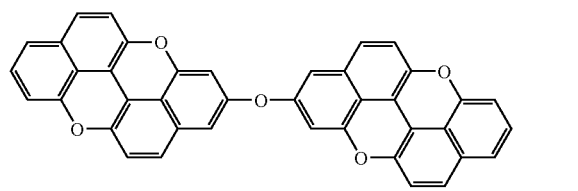
(136)
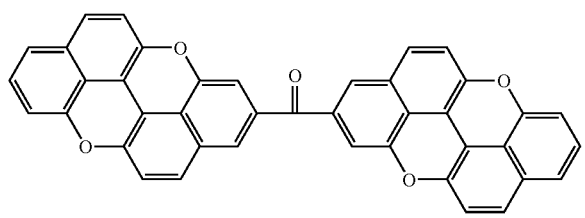
(137)
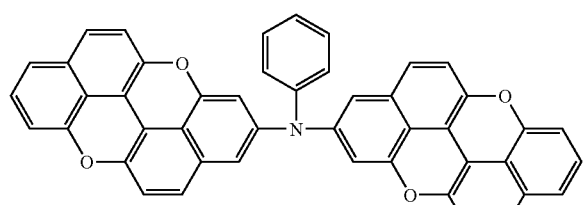
(138)
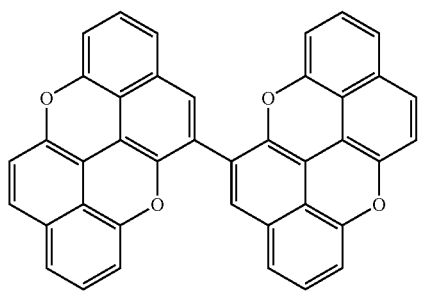
(139)
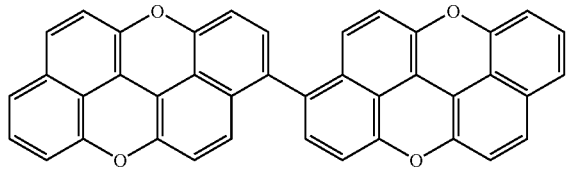
(140)
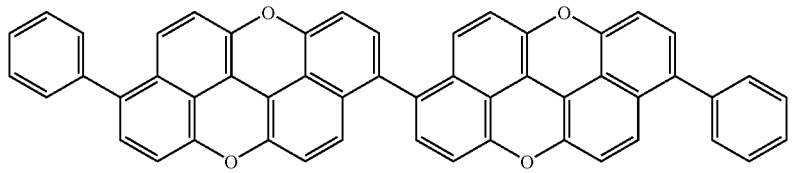
(141)
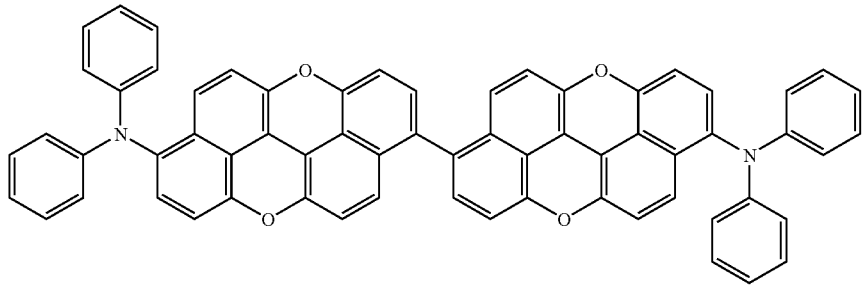

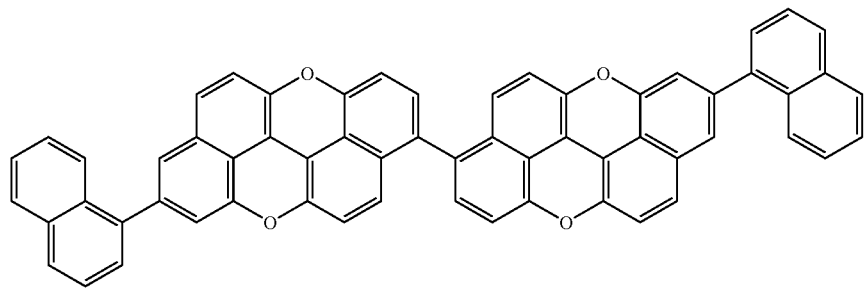
(142)
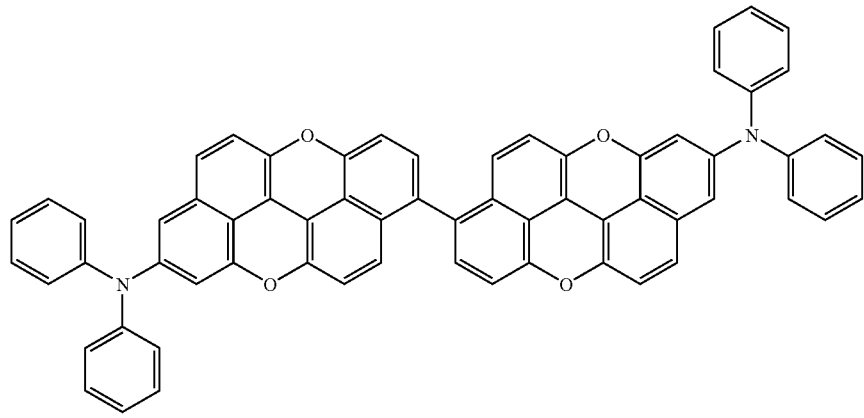
(143)
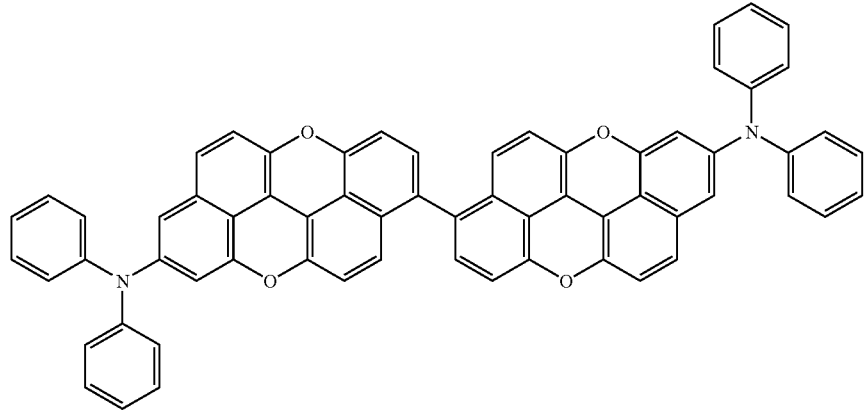
(144)
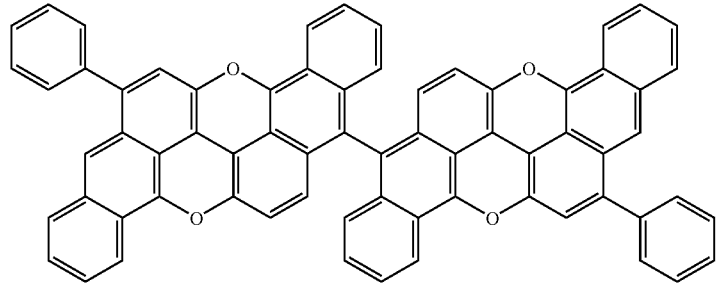
(145)

-continued
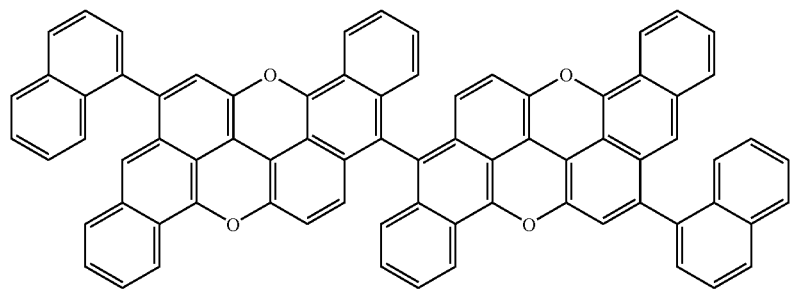
(146)
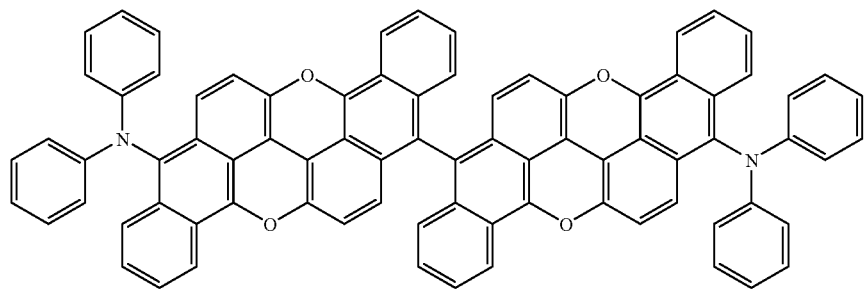
(147)
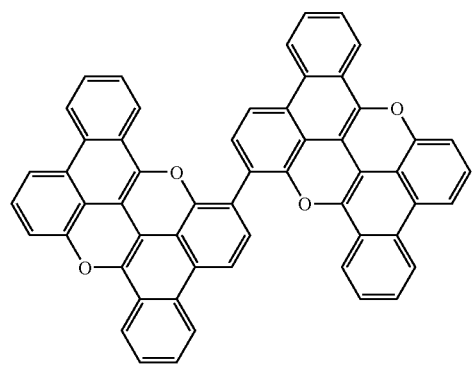
(148)
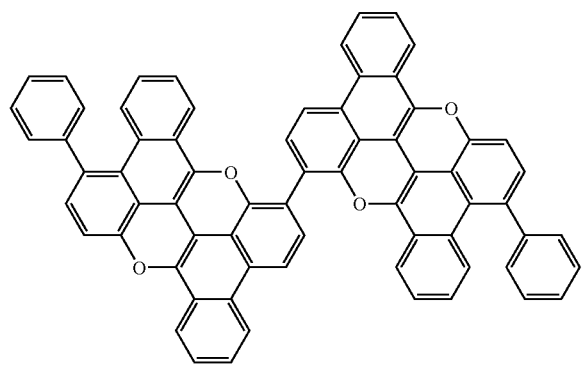
(149)
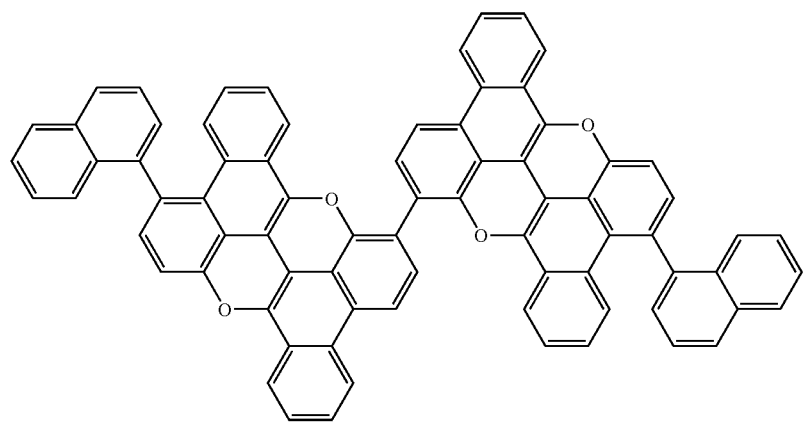
(150)

-continued
(151)
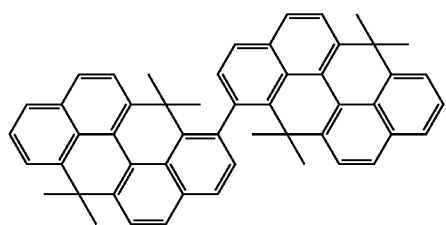
(152)
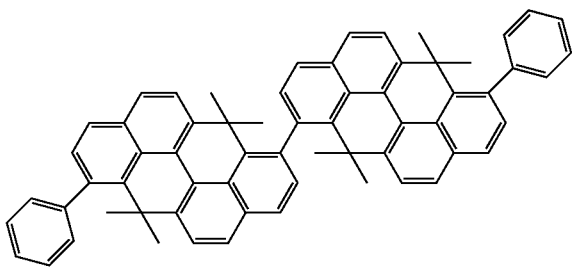
(153)
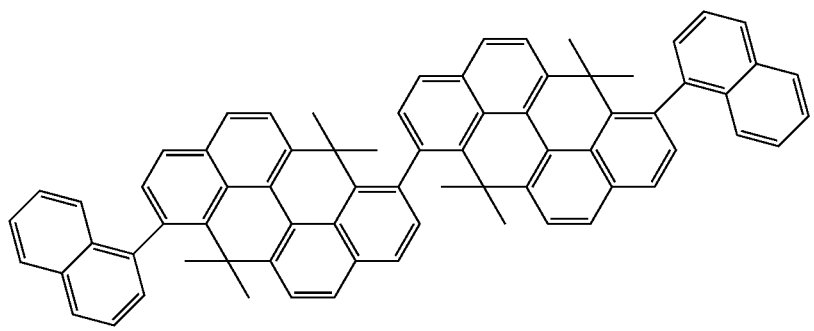
(154)
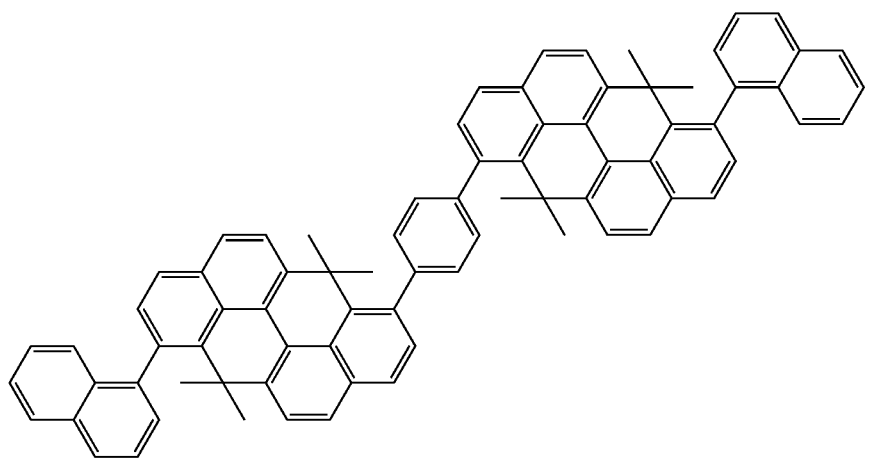
(155)
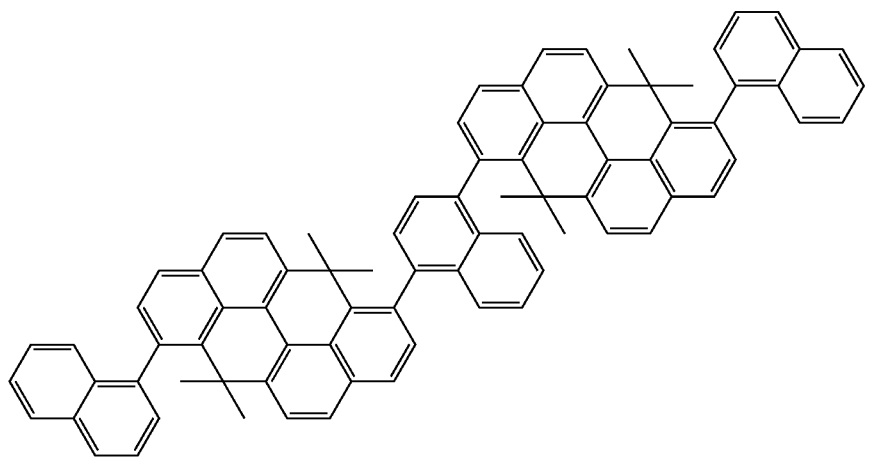

-continued
(156)
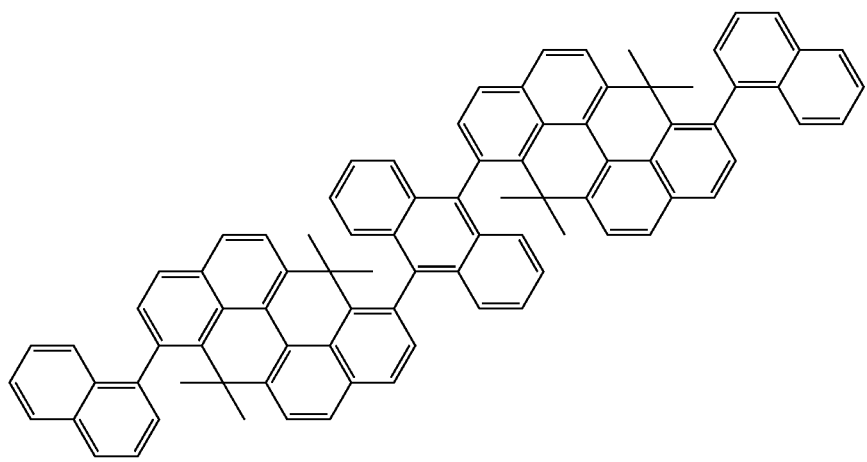
(157)
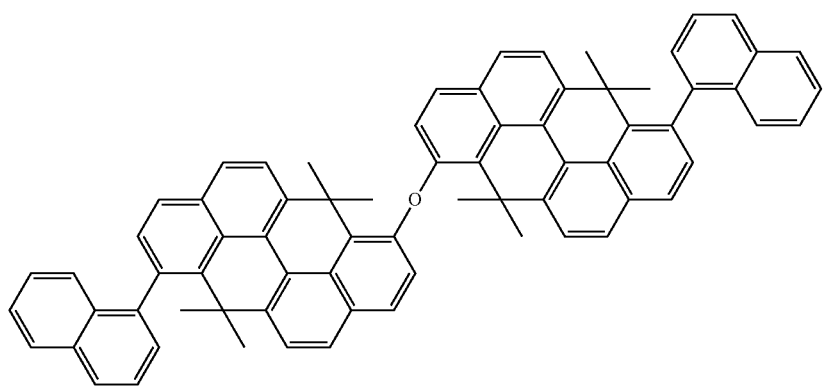
(158)
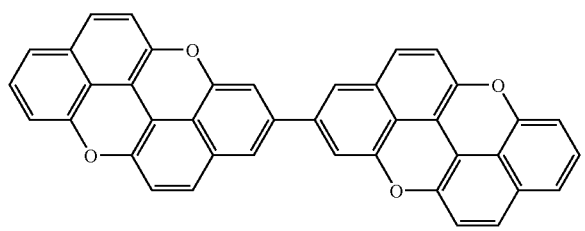
(159)
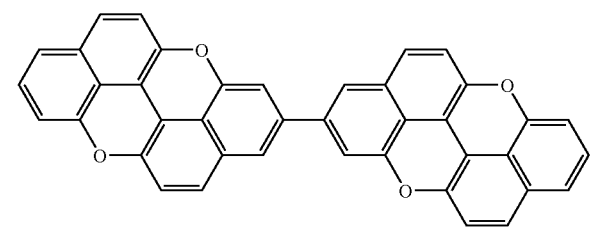
(160)
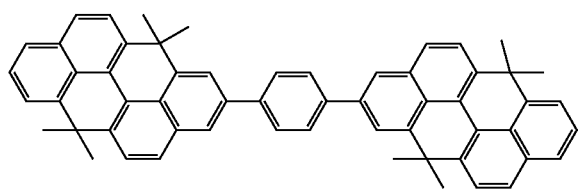
(161)
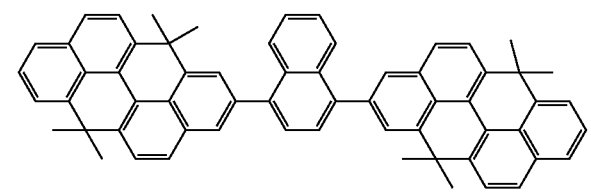
(162)
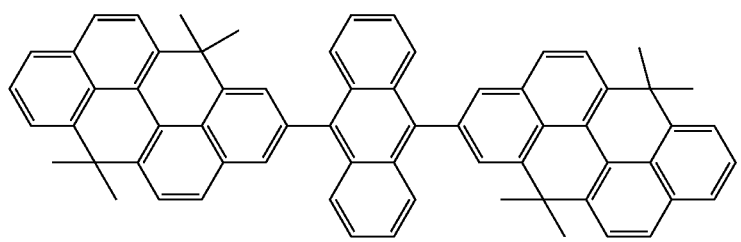

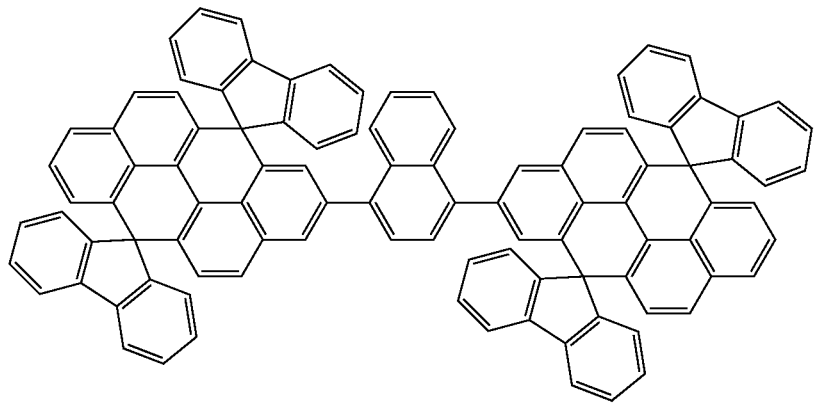
(163)
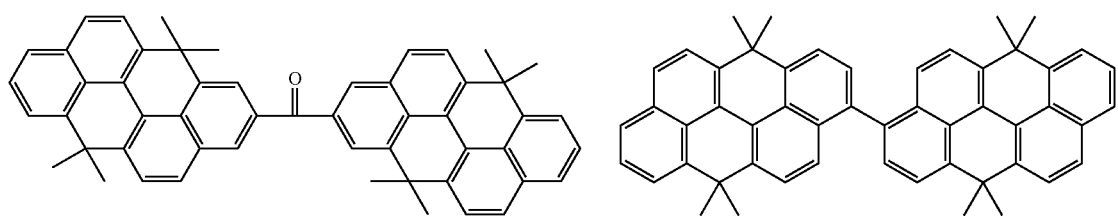
(164) (165)
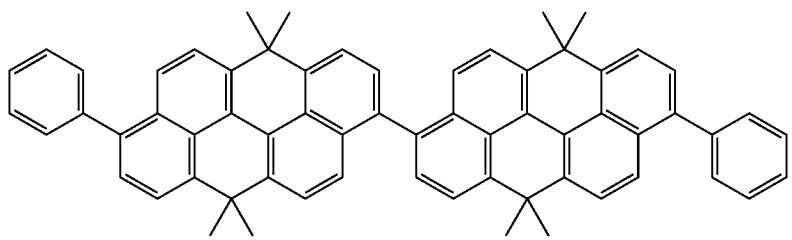
(166)
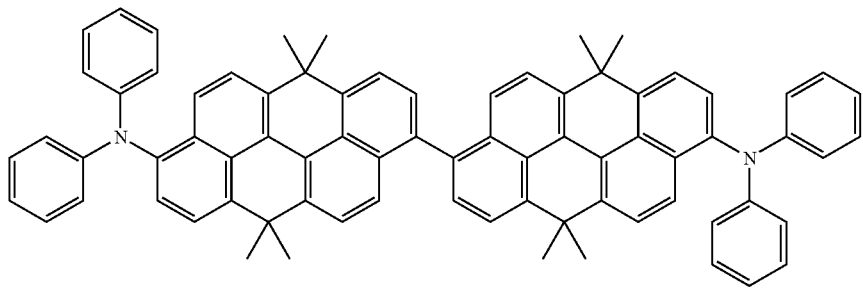
(167)
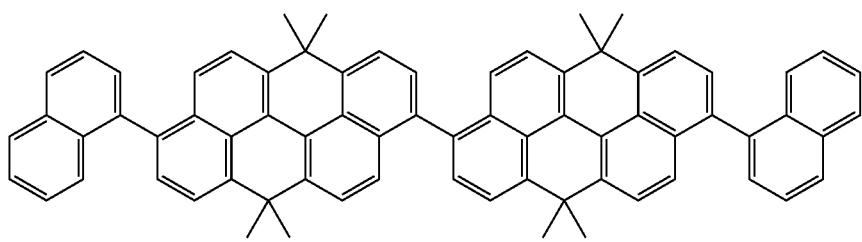
(168)

-continued
(169)
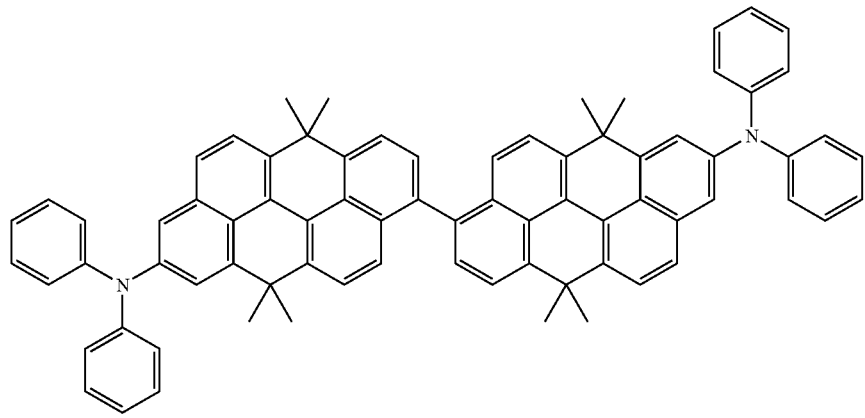
(170)
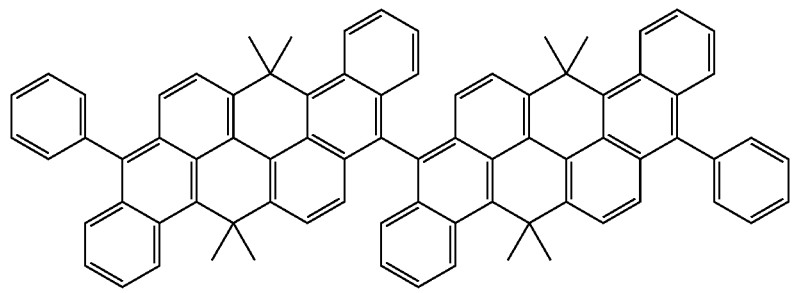
(171)
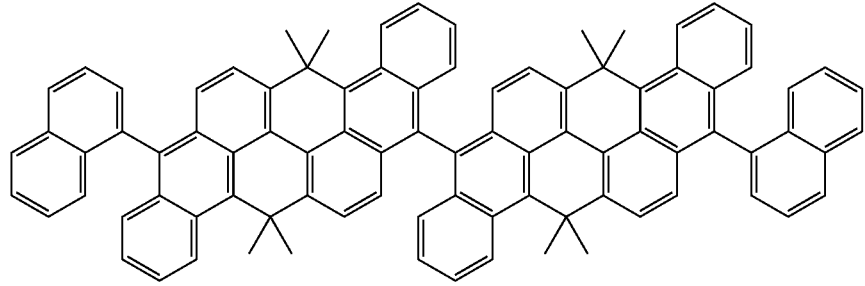
(172)
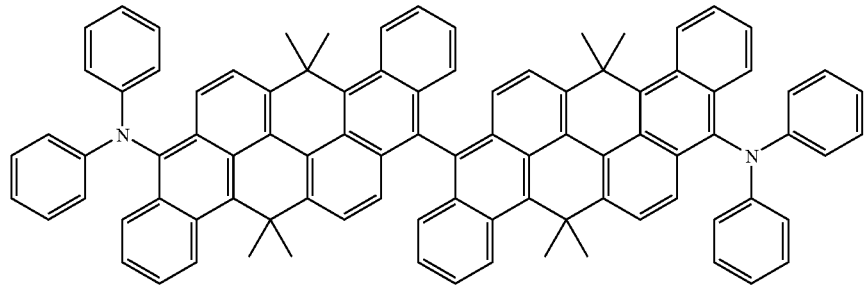
(173)
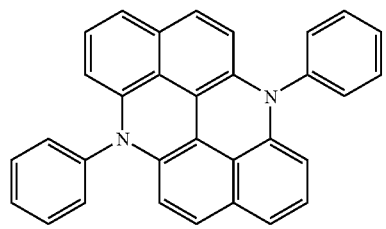
(174)
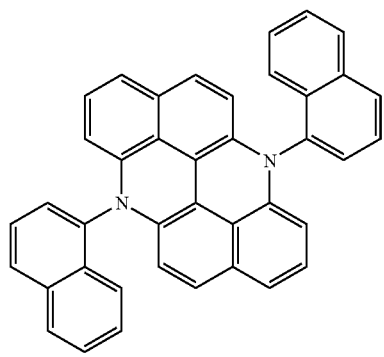

-continued
(175)
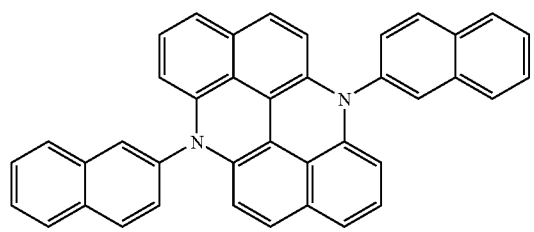
(176)
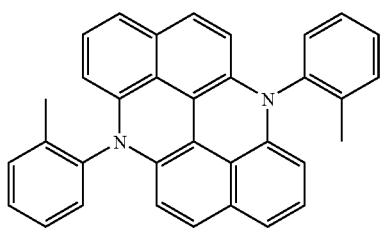
(177)
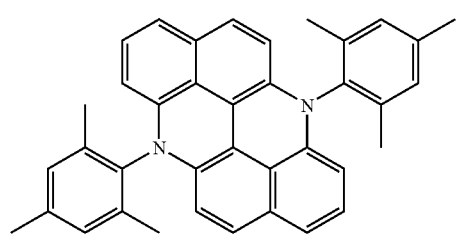
(178)
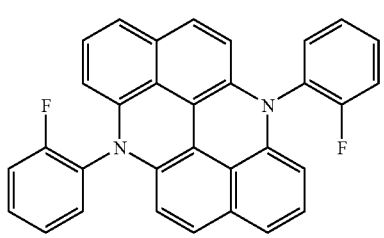
(179)
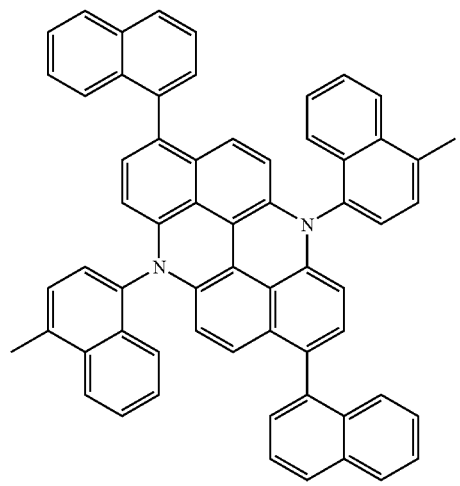
(180)
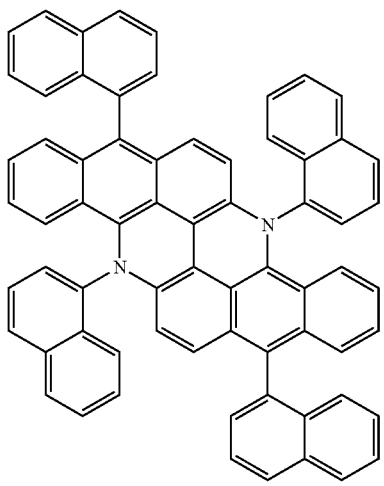
(181)
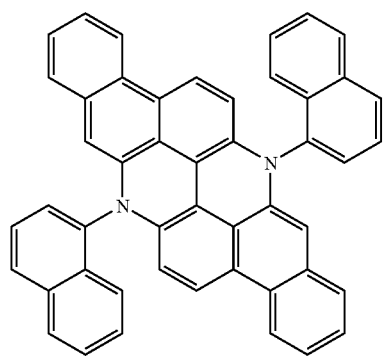
(182)
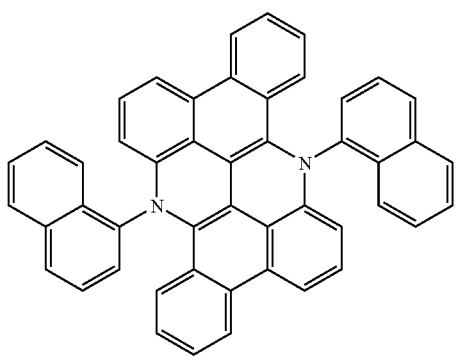

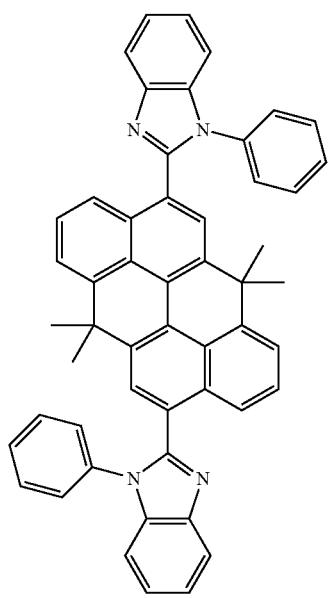
(183)

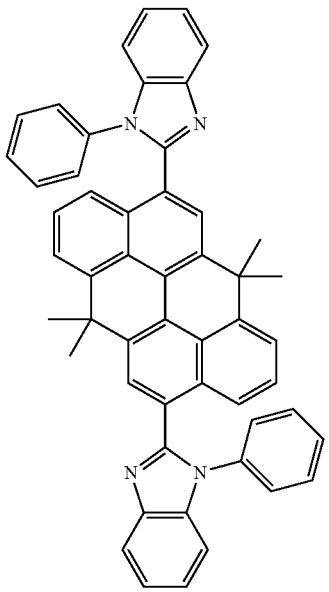
(184)

The compounds according to the invention described above, in particular compounds which are substituted by reactive leaving groups, such as bromine, iodine, boronic acid or boronic acid ester, can also be used as monomers for the preparation of corresponding polymers, oligomers or as the core of dendrimers. The polymerisation here is preferably carried out via the halogen functionality or the boronic acid functionality.

The invention therefore furthermore relates to polymers, oligomers or dendrimers containing one or more compounds of the formulae (1) to (8), where one or more radicals R, $R^1$ and/or $R^2$ represent bonds from the compound of the formulae (1) to (8) to the polymer, oligomer or dendrimer. The polymers, oligomers or dendrimers may be conjugated, partially conjugated or non-conjugated.

The same preferences as described above apply to the recurring units of the formulae (1) to (8).

These monomers are homopolymerised or copolymerised with further monomers. Suitable and preferred comonomers are selected from fluorenes (for example as described in EP 842208 or WO 00/22026), spirobifluorenes (for example as described in EP 707020, EP 894107 or WO 06/061181), para-phenylenes (for example as described in WO 92/18552), carbazoles (for example as described in WO 04/070772 or WO 04/113468), thiophenes (for example as described in EP 1028136), dihydrophenanthrenes (for example as described in WO 05/014689), cis- and trans-indenofluorenes (for example as described in WO 04/041901 or WO 04/113412), ketones (for example as described in WO 05/040302), phenanthrenes (for example as described in WO 05/104264 or WO 07/017,066) or also a plurality of these units. The polymers, oligomers and dendrimers usually also contain further units, for example emitting (fluorescent or phosphorescent) units, such as, for example, vinyltriarylamines (for example as described in the unpublished application DE 102005060473.0) or phosphorescent metal complexes (for example as described in WO 06/003000), and/or charge-transport units, in particular those based on triarylamines.

Depending on whether the unit of the formulae (1) to (8) carries one, two or more functional groups, it is incorporated into the polymer, oligomer or dendrimer as terminal group, as linear recurring unit or as branching unit.

The compounds of the formulae (1) to (8) according to the invention can be prepared by synthetic steps known to the person skilled in the art. Thus, the various substituted skeletons can be prepared, for example, by oxidative coupling of unsubstituted and substituted 1,1'-bi-2-naphthols, as shown in Scheme 1 for the example of peri-xanthenoxanthene and 6,6'-dibromo-peri-xanthenoxanthene. The oxidative cyclisation is carried out either by reaction with stoichiometric or superstoichiometric amounts of transition-metal oxides, such as $MnO_2$, CuO, etc. (DE 545212), or by means of atmospheric oxygen with addition of catalytic amounts of transition-metal compounds and a base (DE 510443).

Scheme 1

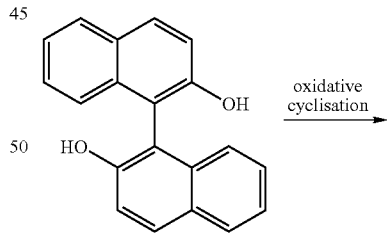

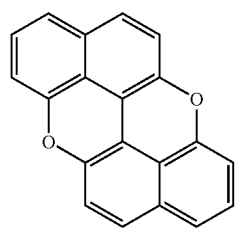

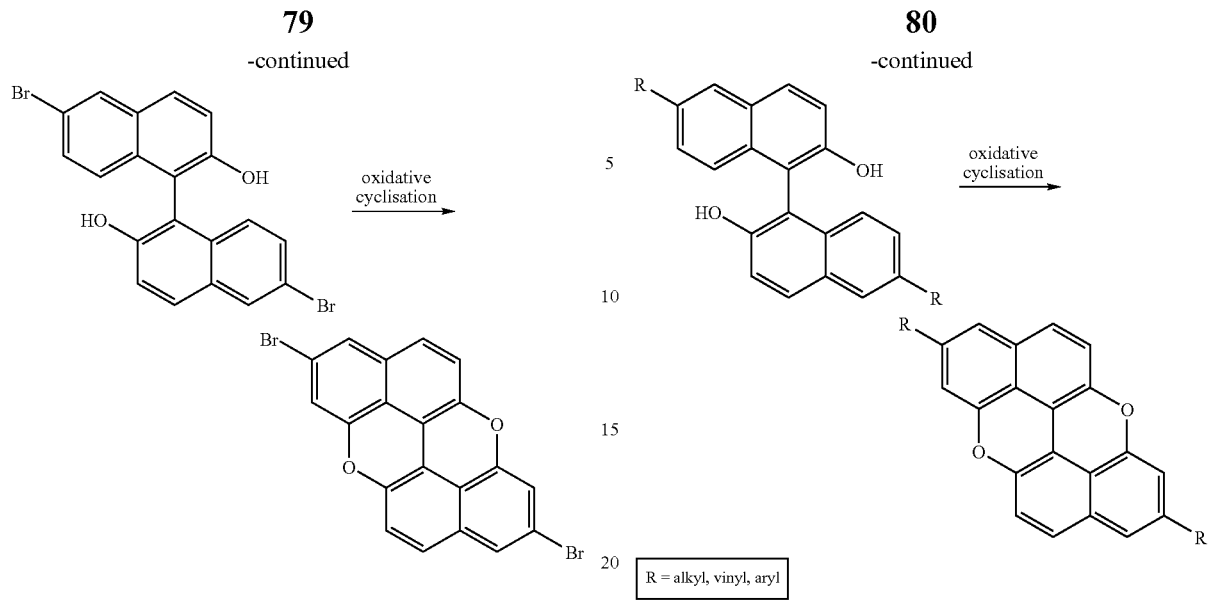

Surprisingly, it has been found that alkyl-, vinyl-, aryl- and diarylamino-substituted 1,1'-bi-2-naphthols can also undergo this coupling (Schemes 2 and 3) without oxidative decomposition of the said radicals occurring. The 6-alkyl-, 6-vinyl-, 6-aryl- and 6-diarylamino-substituted 1,1'-bi-2-naphthols used as starting materials for this coupling are readily accessible from 6-bromo-2-naphthol by reaction with alkyl-, vinyl- or arylboronic acids in a Suzuki coupling or with arylamines in a Hartwig-Buchwald amination and subsequent oxidative coupling of the 6-substituted 2-naphthols to give the 6,6'-substituted 1,1'-bi-2-naphthols using aqueous iron(III) chloride (for example Ding et al., *Tietrahedron* 1996, 52, 1005).

It is also possible to couple analogously 171'-bi-2-anthrols to give compounds of the formula (2), 9,9'-biphenanthrene-10,10'-diols to give compounds of the formula (3) and 1,1'-biphenanthrene-2,2'-diols to give compounds of the formula (4).

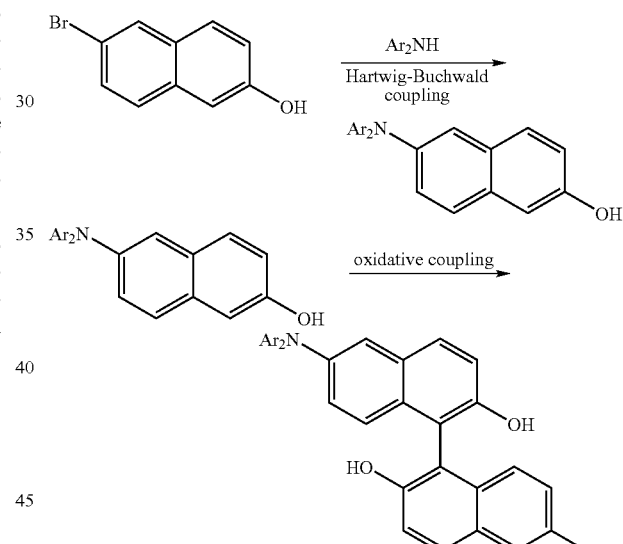

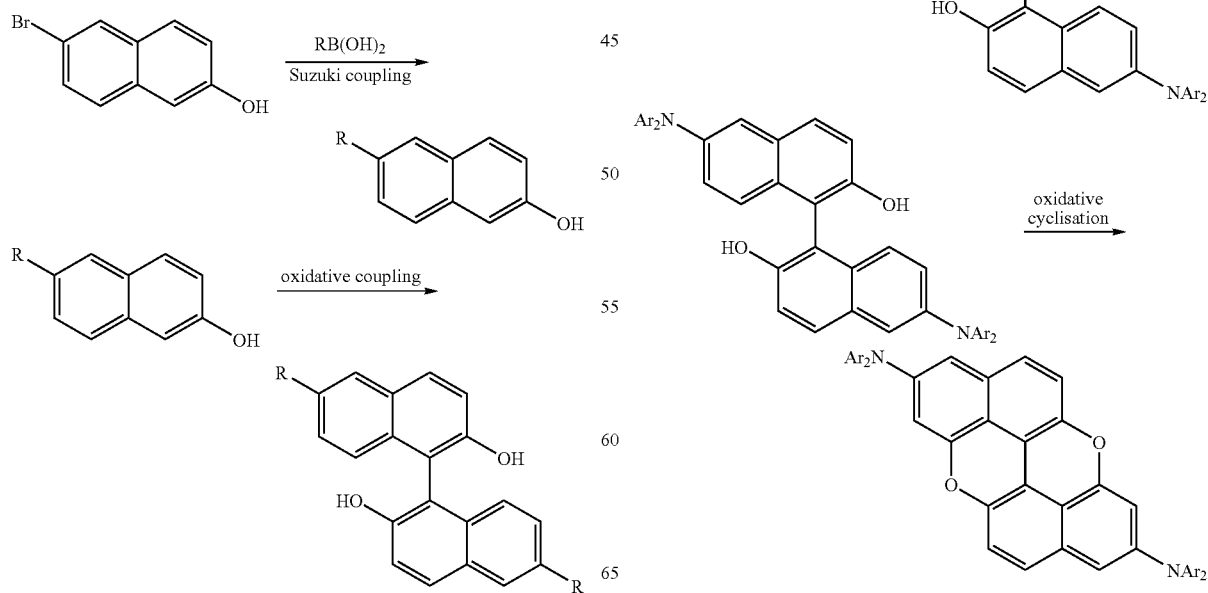

Direct functionalisation of the skeletons, for example by bromination, is likewise possible, as shown by way of example in Scheme 4 for peri-xanthenoxanthenes. The bromination is preferably carried out using N-bromosuccinimide (NBS) in an inert high-boiling solvent, such as o-dichlorobenzene or nitrobenzene, where a suitable stoichiometric ratio of NBS to peri-xanthenoxanthene results in 5-mono-, 5,5'-di-, 5,5',7,7'-tetra- or 3,3',5,5',7,7'-hexabromides. In the case of monobromination, about 15% of 5,5'-dibromo-peri-xanthenoxanthene is formed in addition to about 15% of unchanged peri-xanthenoxanthene, where the latter can easily be removed by boiling the mixture with dichloromethane, and the former can be separated off by fractional crystallisation from chlorobenzene owing to its low solubility.

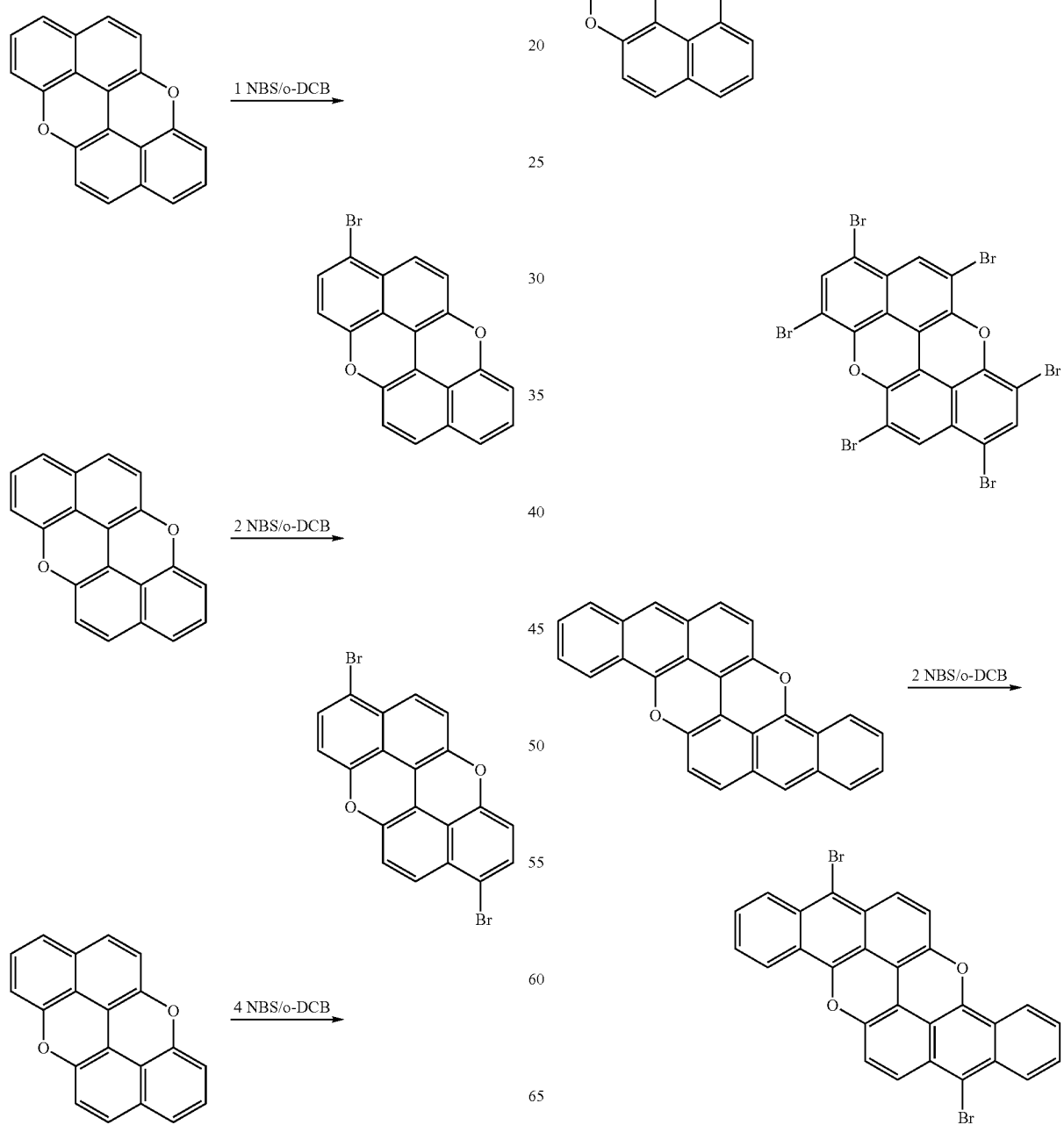

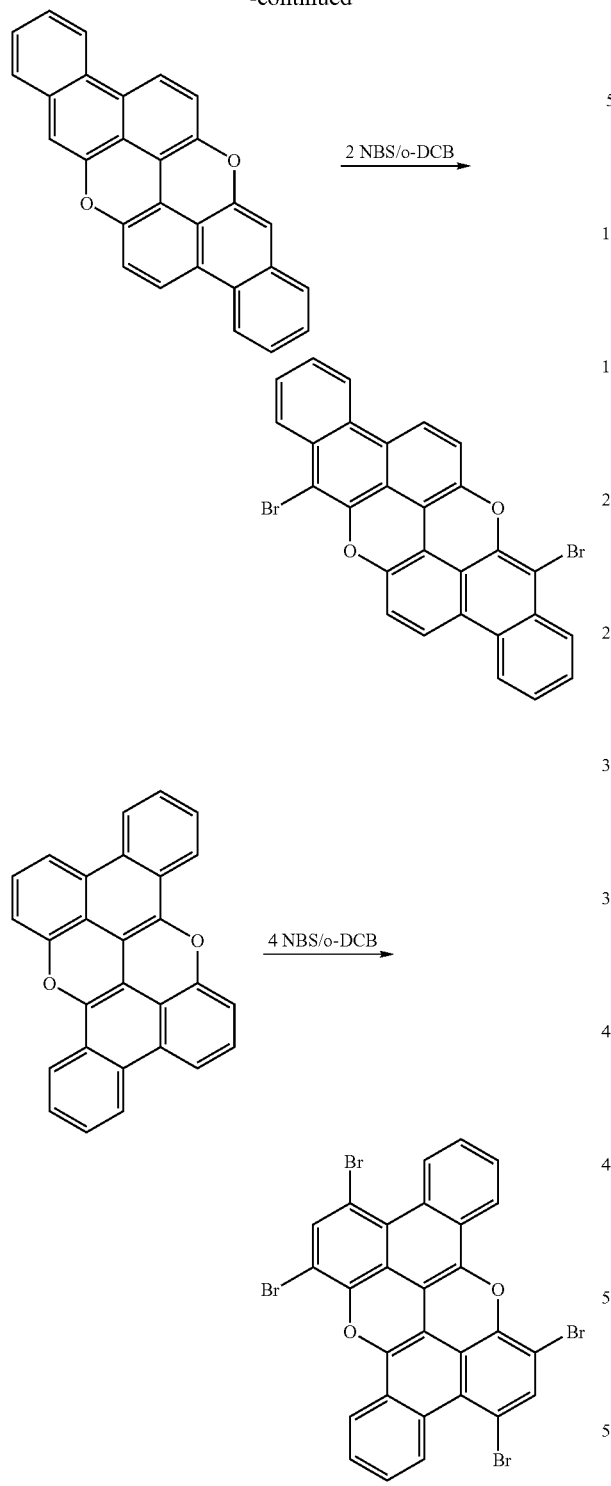
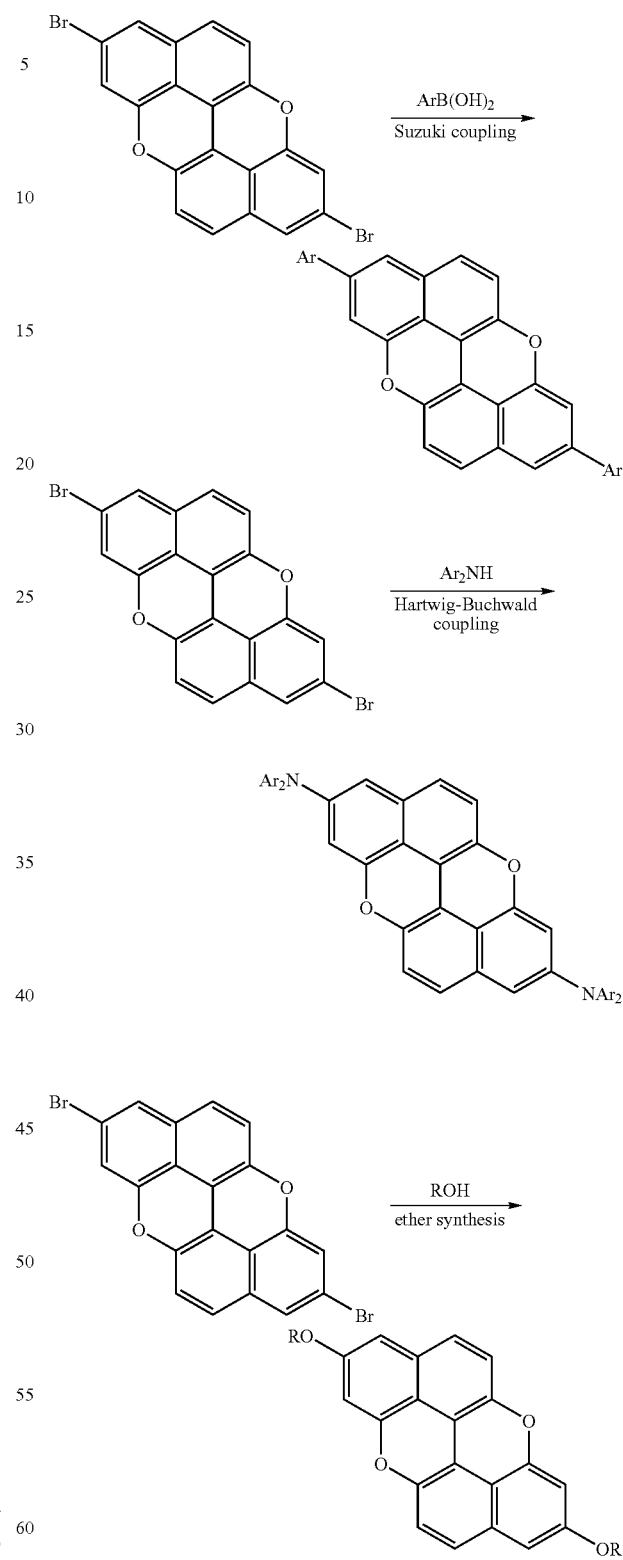

Direct functionalisation (bromination) is complementary to the above-described oxidative cyclisation with respect to the regiochemistry. The two methods together therefore allow targeted functionalisation in all possible positions.

The resultant 5-mono-, 5,5'-di-, 6,6'-di-, 5,5',7,7'-tetra- or 3,3',5,5',7,7'-hexabromides can of course be converted further by standard methods, as shown in Scheme 5 for the example of 6,6'-dibromo-peri-xanthenoxanthene.

Besides bromination, direct conversion of the skeletons into ketones also succeeds by Friedel-Crafts reaction with aromatic acid chlorides in the presence of Lewis acids, such as aluminium chloride (Scheme 6) (Pummerer et al., *Annalen der Chemie* 1942, 553, 103).

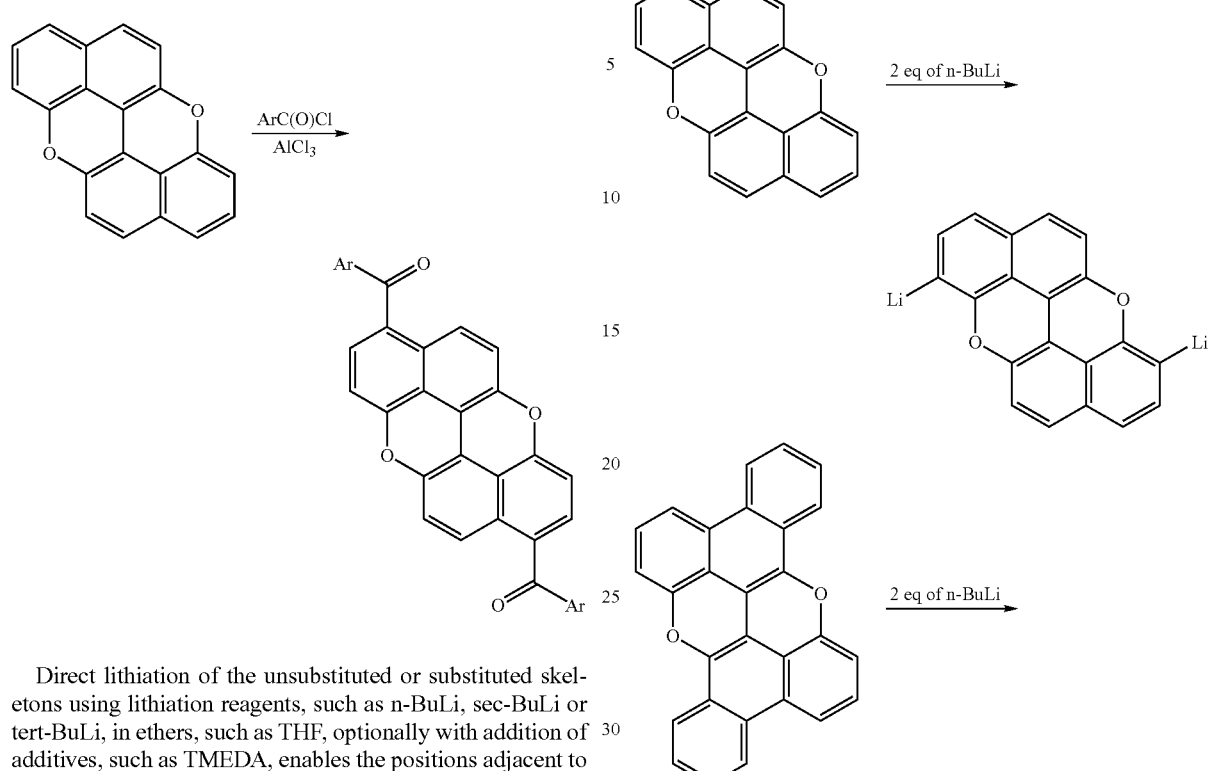

Direct lithiation of the unsubstituted or substituted skeletons using lithiation reagents, such as n-BuLi, sec-BuLi or tert-BuLi, in ethers, such as THF, optionally with addition of additives, such as TMEDA, enables the positions adjacent to the heteroatoms to be functionalised specifically (Scheme 7). The organolithium compounds obtained from the bromides by transmetallation can be reacted entirely analogously. The organolithium compounds can be reacted by conventional methods with electrophiles, such as iodine, boronic acid esters, organotin compounds, chlorophosphines, nitriles, carbamoyl chlorides, etc., or dimerised using oxidants, such as anhydrous copper(II) chloride (Scheme 8).

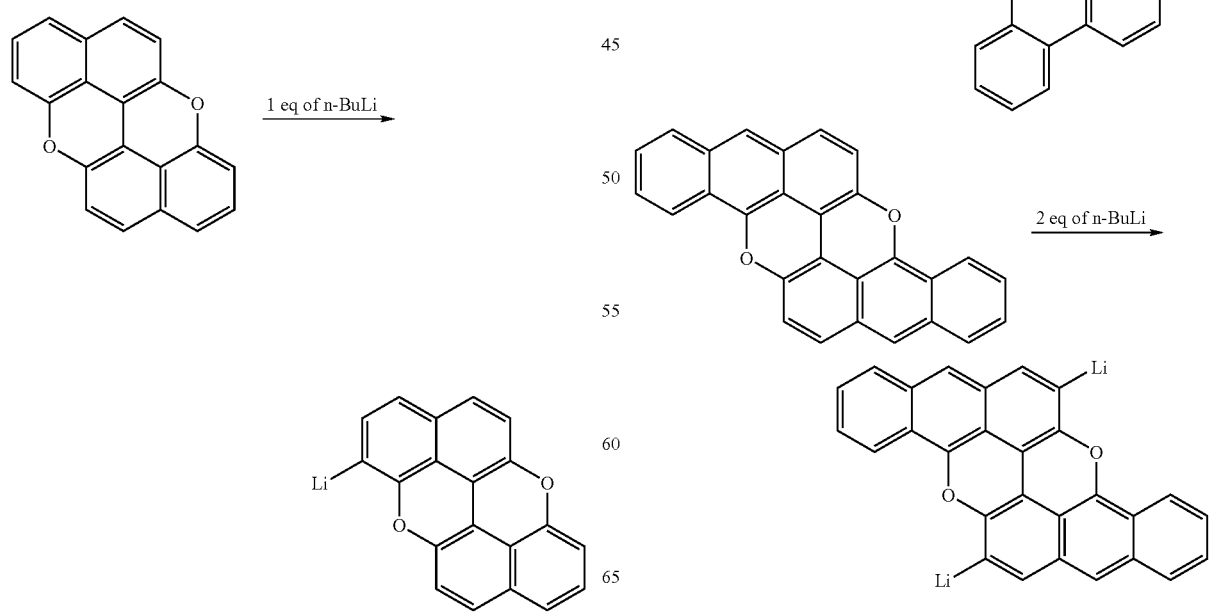

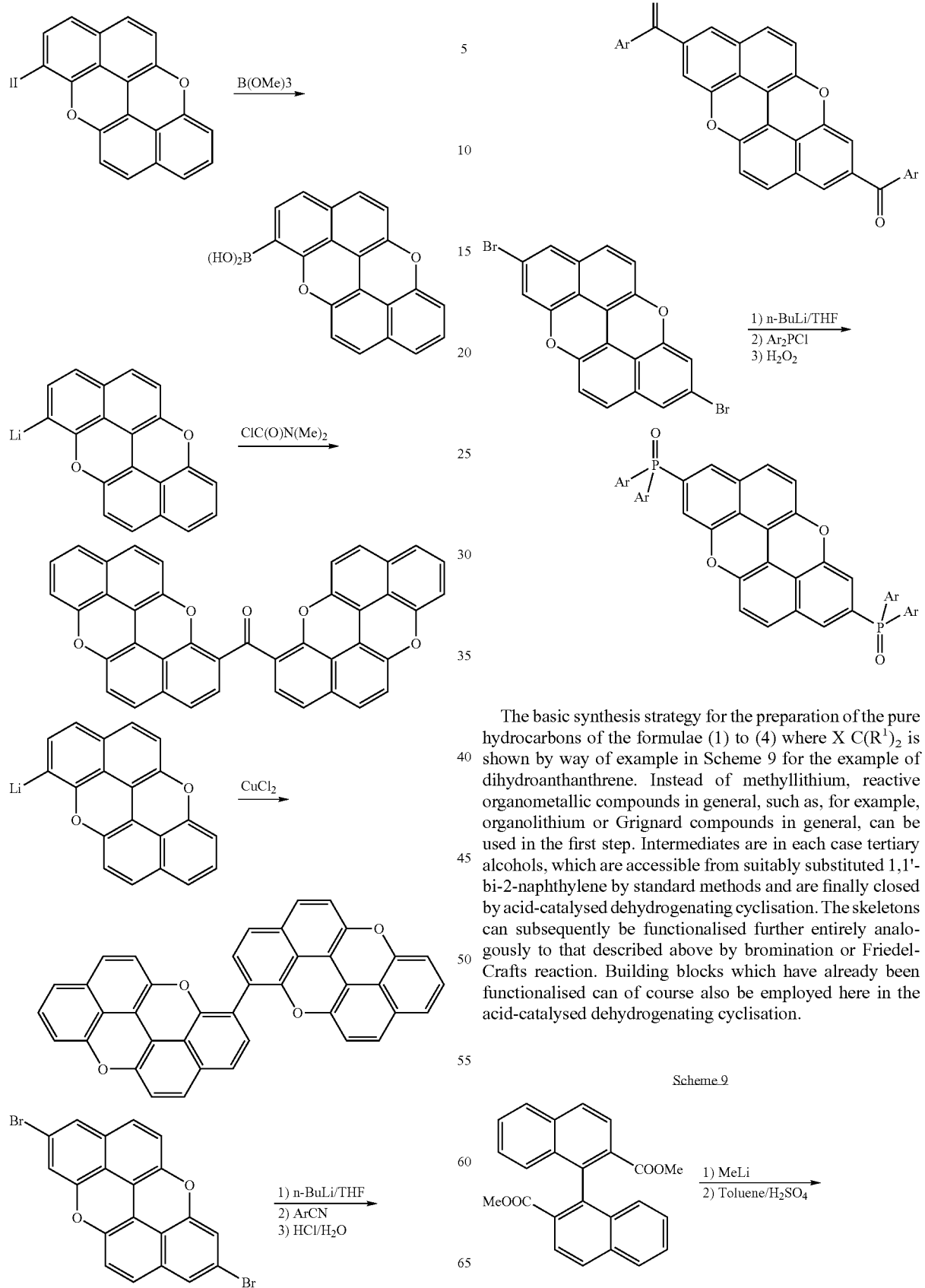

The basic synthesis strategy for the preparation of the pure hydrocarbons of the formulae (1) to (4) where X C(R$^1$)$_2$ is shown by way of example in Scheme 9 for the example of dihydroanthanthrene. Instead of methyllithium, reactive organometallic compounds in general, such as, for example, organolithium or Grignard compounds in general, can be used in the first step. Intermediates are in each case tertiary alcohols, which are accessible from suitably substituted 1,1'-bi-2-naphthylene by standard methods and are finally closed by acid-catalysed dehydrogenating cyclisation. The skeletons can subsequently be functionalised further entirely analogously to that described above by bromination or Friedel-Crafts reaction. Building blocks which have already been functionalised can of course also be employed here in the acid-catalysed dehydrogenating cyclisation.

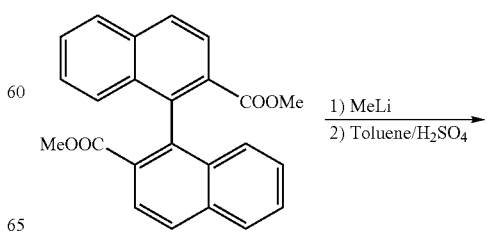

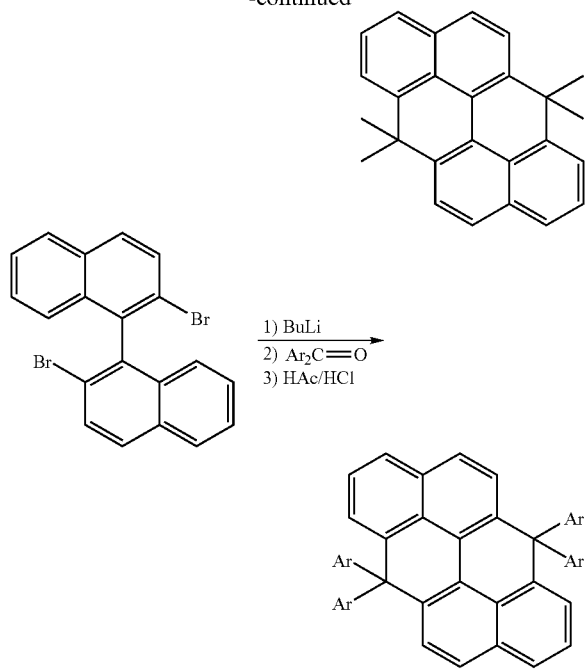

The invention furthermore relates to a process for the preparation of the compounds of the formulae (1) to (4) in which X=O, characterised by oxidative cyclisation of the binaphthol or bianthrol or biphenanthrol derivative which has already been correspondingly functionalised, in accordance with Scheme 2.

The invention furthermore relates to a process for the preparation of the compounds of the formulae (1) to (4) in which X=C(R$^1$)$_2$, characterised by acid-catalysed dehydrating cyclisation of the binaphthyl or bianthryl or biphenanthryl derivative which has optionally already been correspondingly functionalised and which is in each case substituted by two groups of the formula —C(R$^1$)$_2$(OH) in the ortho-positions to the link of the binaphthyl or bianthryl or biphenanthryl, in accordance with Scheme 9.

The functionalised compounds, for example the brominated compounds, can be employed as monomers for the preparation of polymers, oligomers or dendrimers, either directly or after conversion into a boronic acid derivative.

The compounds of the formulae (1) to (8) are suitable for use in electronic devices, in particular in organic electroluminescent devices (OLEDs, PLEDs). Depending on the substitution, the compounds are employed in different functions and layers.

The invention therefore furthermore relates to the use of compounds of the formulae (1) to (8) in electronic devices, in particular in organic electroluminescent devices.

The invention furthermore relates to electronic devices comprising at least one compound of the formulae (1) to (8), in particular organic electroluminescent devices, comprising anode, cathode and at least one emitting layer, characterised in that at least one organic layer, which may be an emitting layer or another layer, comprises at least one compound of the formulae (1) to (8).

Apart from the cathode, anode and the emitting layer, the organic electroluminescent device may also comprise further layers. These are selected, for example, from hole-injection layer, hole-transport layer, electron-transport layer, electron-injection layer and/or charge-generation layer (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*). However, it should be pointed out that each of these layers does not necessarily have to be present.

In a further preferred embodiment of the invention, the organic electroluminescent device comprises a plurality of emitting layers, where at least one organic layer comprises at least one compound of the formulae (1) to (8). These emission layers particularly preferably have in total a plurality of emission maxima between 380 nm and 750 nm, resulting overall in white emission, i.e. different emitting compounds which are able to fluoresce or phosphoresce are used in the emitting layer. Particular preference is given to three-layer systems where at least one of these layers comprises at least one compound of the formulae (1) to (8) and where the three layers exhibit blue, green and orange or red emission (for the basic structure see, for example, WO 05/011013). Likewise suitable for white emission are emitters which have broad-band emission bands and thus exhibit white emission.

In a preferred embodiment of the invention, the compounds of the formulae (1) to (8) are employed as emitting materials. In particular, the compounds are suitable as emitting compounds if the symbols X stand for O, S or N(R$^1$), in particular for O. Depending on the nature of the substituents R and the position in which these substituents are bonded, the compounds according to the invention are suitable as emitting materials for different emission colours. Thus, for example, the compounds of the formula (9) in which the substituents R stand for aromatic or heteroaromatic groups exhibit blue emission, while compounds of the formula (10) or (11) with the same substituents R exhibit blue-green emission. By contrast, compounds of the formula (12) which have four aromatic or heteroaromatic substituents R exhibit intense green emission.

The proportion of the compound of the formulae (1) to (8) in the mixture of the emitting layer is between 0.1 and 50.0% by weight, preferably between 0.5 and 20.0% by weight, particularly preferably between 1.0 and 10.0% by weight. The proportion of the host material is correspondingly between 50.0 and 99.9% by weight, preferably between 80.0 and 99.5% by weight, particularly preferably between 90.0 and 99.0% by weight.

Suitable host materials are materials from various classes of substance. Preferred host materials are selected from the classes of the oligoarylenes (for example 2,2',7,7'-tetraphenylspirobifluorene as described in EP 676461 or dinaphthylanthracene), in particular the oligoarylenes containing condensed aromatic groups, the oligoarylenevinylenes (for example DPVBi or spiro-DPVBi as described in EP 676461), the polypodal metal complexes (for example as described in WO 04/081017), the hole-conducting compounds (for example as described in WO 04/058911), the electron-conducting compounds, in particular ketones, phosphine oxides, sulfoxides, etc. (for example as described in WO 05/084081 and WO 05/084082), the atropisomers (for example as described in WO 06/048268) or the boronic acid derivatives (for example as described in WO 06/117052). Suitable host materials are furthermore also the compounds of the formulae (1) to (8) according to the invention, in particular the derivatives described below for this use. Apart from the compounds according to the invention, particularly preferred host materials are selected from the classes of the oligoarylenes containing naphthalene, anthracene and/or pyrene or atropisomers of these compounds, the oligoarylenevinylenes, the ketones, the phosphine oxides and the sulfoxides. Apart from the compounds according to the invention, very particularly preferred host materials are selected from the classes of the oligoarylenes containing anthracene and/or pyrene or atropisomers of these compounds, the phosphine oxides and the sulfoxides. For the purposes of this invention, an oligoarylene is intended to be taken to mean a compound in which at least three aryl or arylene groups are bonded to one another.

In a further embodiment of the invention, the compounds of the formulae (1) to (8) are employed as host material. Suitable as host material are, in particular, compounds in which the symbols X stand for $C(R^1)_2$. In this case, one or more substituents R are furthermore preferably selected from aryl or heteroaryl groups, in particular phenyl, o-, m- or p-biphenyl, 1- or 2-naphthyl, 2-fluorenyl and 2-spirobifluorenyl, each of which may be substituted by one or more radicals $R^2$. The compounds can be employed as host material for fluorescent or phosphorescent dopants, in particular for fluorescent dopants.

A host material in a system comprising host and dopant is taken to mean the component which is present in the higher proportion in the system. In a system comprising one host and a plurality of dopants, the host is taken to mean the component whose proportion in the mixture is the highest.

The proportion of the host material of the formulae (1) to (8) in the emitting layer is between 50.0 and 99.9% by weight, preferably between 80.0 and 99.5% by weight, particularly preferably between 90.0 and 99.0% by weight. The proportion of the dopant is correspondingly between 0.1 and 50.0% by weight, preferably between 0.5 and 20.0% by weight, particularly preferably between 1.0 and 10.0% by weight.

Preferred dopants in fluorescent devices are selected from the class of the monostyrylamines, distyrylamines, tristyrylamines, tetrastyrylamines and arylamines. A monostyrylamine is taken to mean a compound which contains one styryl group and at least one amine, which is preferably aromatic. A distyrylamine is taken to mean a compound which contains two styryl groups and at least one amine, which is preferably aromatic. A tristyrylamine is taken to mean a compound which contains three styryl groups and at least one amine, which is preferably aromatic. A tetrastyrylamine is taken to mean a compound which contains four styryl groups and at least one amine, which is preferably aromatic. For the purposes of this invention, an arylamine or an aromatic amine is taken to mean a compound which contains three aromatic or heteroaromatic ring systems bonded directly to the nitrogen, at least one of which is preferably a condensed ring system having at least 14 aromatic ring atoms. The styryl groups are particularly preferably stilbenes, which may also be further substituted on the double bond or on the aromatic rings. Examples of dopants of this type are substituted or unsubstituted tristilbenamines or further dopants which are described, for example, in WO 06/000388, WO 06/000389 and WO 06/058737 and in the unpublished patent applications DE 102005058543.4 and DE 102006015183.6. Compounds as described in WO 06/122630 and as described in the unpublished application DE 102006025846.0 are furthermore preferred as dopants. Suitable dopants are likewise the compounds according to the invention described here, in particular the compounds mentioned as dopants above.

In still a further preferred embodiment of the invention, the compounds of the formulae (1) to (8) are employed as hole-transport material or as hole-injection material. Suitable as hole-transport or hole-injection material are, in particular, compounds in which the symbol X stands for O, S or $N(R^1)$, in particular for O. It may be preferred for the compounds to be substituted by at least one $N(Ar)_2$ group, preferably by at least two $N(Ar)_2$ groups, and/or for the group Y to represent an N(Ar) group. The $N(Ar)_2$ groups are preferably selected from the formulae (24) and (25) described above. However, even if no substituents of the formula $N(Ar)_2$ are present, the compounds of the formulae (1) to (8) are good hole-transport or hole-injection materials. The compound is preferably employed in a hole-transport or hole-injection layer. For the purposes of this invention, a hole-injection layer is a layer which is directly adjacent to the anode. For the purposes of this invention, a hole-transport layer is a layer which is between a hole-injection layer and an emission layer. If the compounds of the formulae (1) to (8) are used as hole-transport or hole-injection material, it may be preferred for them to be doped with electron-acceptor compounds, for example with $F_4$-TCNQ or with compounds as described in EP 1476881 or EP 1596445.

In still a further embodiment of the invention, the compounds of the formulae (1) to (8) are employed in an electron-transport layer and/or in a hole-blocking layer. This preferably applies if the symbols X stand for $C(R^1)_2$, and in particular if one or more substituents R and/or $R^1$ stand for a group of the formula $C(=O)Ar$ or $P(=O)Ar_2$ and/or if the group Y stands for a group of the formula $C(=O)$ or $P(=O)Ar$.

Compounds as already described above as hole-transport material can also be employed as n-dopant, which releases at least one electron to the electron-transport material, in an electron-transport layer.

In still a further embodiment of the invention, the compounds of the formulae (1) to (8) are employed as electron-transport material. This preferably applies if the symbols X stand for $C(R^1)_2$, $BR^1$, $POR^1$, SO or $SO_2$ and in particular if one or more substituents R and/or $R^1$ contain at least one $C=O$, $P(=O)$ and/or $SO_2$ unit or if one or more substituents P and/or $R^1$ contain an electron-deficient heterocycle. Particularly suitable electron-deficient heterocycles are imidazole, pyrazole, thiazole, benzimidazole, benzothiazole, triazole, oxadiazole, benzothiadiazole, phenanthroline, etc. These groups are particularly preferably bonded directly to the central unit according to the invention. It may furthermore be preferred for the compound to be doped with electron-donor compounds.

Recurring units of the formulae (1) to (8) may also be employed in polymers as polymer backbone, as emitting unit or as hole-transport unit. The preferred substitution patterns here correspond to those described above.

Preference is furthermore given to an organic electroluminescent device, characterised in that one or more layers are coated by means of a sublimation process, in which the materials are vapour-deposited in vacuum sublimation units at a pressure below $10^{-5}$ mbar, preferably below $10^{-6}$ mbar, particularly preferably below $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar.

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds are necessary for this purpose. High solubility can be achieved by suitable substitution of the compounds.

The compounds according to the invention have the following surprising advantages over the prior art on use in organic electroluminescent devices:

1. The compounds according to the invention are accessible synthetically in a few steps with high yield. The compounds are obtained in high purity, even as the crude product. Since very high purity requirements are made of organic materials for electronic applications, this is a technical advantage since subsequent purification of the compounds is considerably simplified.

2. The compounds according to the invention have very good efficiencies and lifetimes in organic electroluminescent devices.
3. The compounds according to the invention have high thermal stability and can be sublimed without decomposition. This considerably simplifies purification thereof by sublimation and vacuum production of the electroluminescent device.
4. The compounds according to the invention have lower oxygen and light sensitivity than compounds used in accordance with the prior art as blue and green emitters, in particular than bis(diarylamine) derivatives of condensed aromatic compounds, such as anthracene, pyrene or chrysene.

The present application text is directed to the use of the compounds according to the invention in relation to OLEDs and PLEDs and the corresponding displays. In spite of this restriction of the description, it is possible for the person skilled in the art, without further inventive step, also to employ the compounds according to the invention in other electronic devices, for example in organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photoreceptors.

The present invention likewise relates to the use of the compounds according to the invention in the corresponding devices and to these devices themselves.

The invention is explained in greater detail by the following examples, without wishing it to be restricted thereby.

EXAMPLES

The following syntheses are carried out under a protective-gas atmosphere, unless indicated otherwise. The starting materials can be purchased from ALDRICH or ABCR. Peri-xanthenoxanthene and 6,6'-dibromo-peri-xanthenoxanthene are prepared in accordance with DE 545212.

Example 1

5,5'-Dibromo-peri-xanthenoxanthene

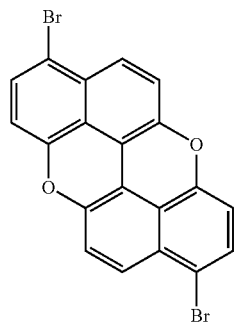

A suspension of 28.2 g (100 mmol) of peri-xanthenoxanthene and 36.5 g (205 mmol) of N-bromosuccinimide in 200 ml of o-dichlorobenzene is stirred at 180° C. for 6 h. After cooling, the solid is filtered off with suction, washed five times with 200 ml of ethanol each time and dried in vacuo. Recrystallisation of the crude product twice from o-dichlorobenzene gives 41.4 g (94 mmol) of 5,5'-dibromo-peri-xanthenoxanthene, corresponding to 94.0% of theory, with a purity of 99.0% according to HPLC.

Example 2

5,5',7,7'-Tetrabromo-peri-xanthenoxanthene

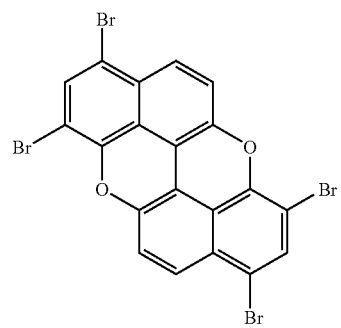

A suspension of 28.2 g (100 mmol) of peri-xanthenoxanthene and 73.0 g (410 mmol) of N-bromosuccinimide in 300 ml of o-dichlorobenzene is stirred at 180° C. for 16 h. After cooling, the solid is filtered off with suction, washed five times with 200 ml of ethanol each time and dried in vacuo. Recrystallisation of the crude product twice from o-dichlorobenzene gives 55.0 g (92 mmol) of 5,5',7,7'-tetrabromo-peri-xanthenoxanthene, corresponding to 92.0% of theory, with a purity of 99.0% according to HPLC.

Example 3

3,3',5,5',7,7'-Hexabromo-peri-xanthenoxanthene

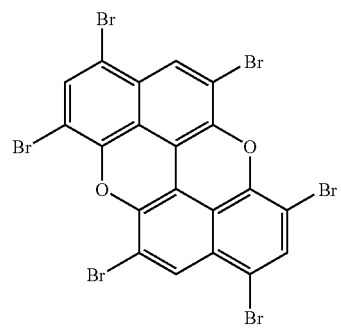

A suspension of 28.2 g (100 mmol) of peri-xanthenoxanthene and 142.4 g (800 mmol) of N-bromosuccinimide in 500 ml of o-dichlorobenzene is stirred at 180° C. for 28 h. After cooling, the solid is filtered off with suction, washed five times with 200 ml of ethanol each time and dried in vacuo. Purification of the crude product three times with boiling o-dichlorobenzene gives 72.5 g (96 mmol) of 3,3',5,5',7,7'- hexabromo-peri-xanthenoxanthene, corresponding to 96.0% of theory, with a purity of 99.0% according to HPLC.

Example 4

6,6'-Bis(1-naphthyl)-peri-xanthenoxanthene

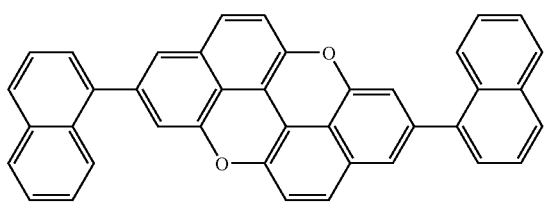

913 mg (3 mmol) of tri-o-tolylphosphine and then 112 mg (0.5 mmol) of palladium(II) acetate are added to a suspension of 22.0 g (50 mmol) of 6,6'-dibromo-peri-xanthenoxanthene, 22.4 g (130 mmol) of naphthyl-boronic acid and 44.6 g (210 mmol) of tripotassium phosphate in a mixture of 800 ml of toluene, 200 ml of dioxane and 800 ml of water, and the mixture is heated under reflux for 18 h. After cooling, the solid is filtered off with suction, washed three times with 300 ml of water each time, three times with 200 ml of ethanol each time and three times with 200 ml of toluene each time and dried in vacuo. Recrystallisation four times from o-dichlorobenzene and subsequent sublimation at T=350° C. and p=2×10$^{-5}$ mbar gives 16.6 g (31 mmol) of 6,6'-bis(1-naphthyl)-peri-xanthenoxanthene, corresponding to 62.1% of theory, with a purity of 99.9% according to HPLC.

Examples 5 to 10

Analogously to Example 4, the compounds shown in Table 1 are prepared by reaction of the corresponding bromo-peri-xanthenoxanthenes with the corresponding arylboronic acids, purified and sublimed.

In Example 9, 25 mmol of 5,5',7,7'-tetrabromo-peri-xanthenoxanthene are employed. In Example 10, 12.5 mmol of 3,3',5,5',7,7'-hexabromo-peri-xanthenoxanthene are employed.

TABLE 1

| Ex. | Product | Yield |
|---|---|---|
| 5 |  | 67.0% |
| 6 |  | 73.9% |
| 7 |  | 81.3% |
| 8 |  | 84.3% |
| 9 |  | 75.0% |

TABLE 1-continued

| Ex. | Product | Yield |
|---|---|---|
| 10 | 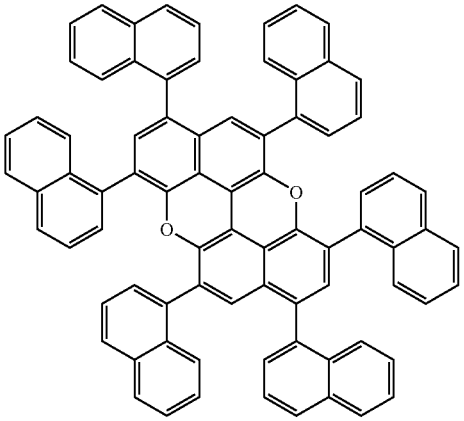 | 58.5% |

Example 11

6,6'-Bis(1-naphthyl)-peri-xanthenoxanthene a) 6-(1-Naphthyl)-2-naphthol

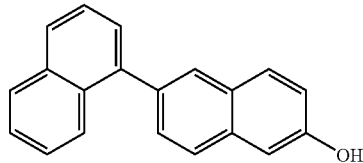

913 mg (3 mmol) of tri-o-tolylphosphine and then 112 mg (0.5 mmol) of palladium(II) acetate are added to a suspension of 111.5 g (500 mmol) of 6-bromo-2-naphthol, 111.8 g (650 mmol) of naphthaleneboronic acid and 224.1 g (1150 mmol) of tripotassium phosphate in a mixture of 1000 ml of toluene, 200 ml of dioxane and 1000 ml of water, and the mixture is heated under reflux for 18 h. After cooling, 200 ml of 2 N hydrochloric acid are added, and the organic phase is separated off, washed three times with 500 ml of 1 N hydrochloric acid, once with 500 ml of saturated sodium chloride solution, filtered through silica gel and evaporated to dryness in vacuo. The residue is recrystallised from 150 ml of toluene. Yield: 113.3 g (419 mmol), 83.8% of theory; purity: 98% according to NMR.

b) 6,6'-(1-Naphthyl)-1,1'-bi-2-naphthol

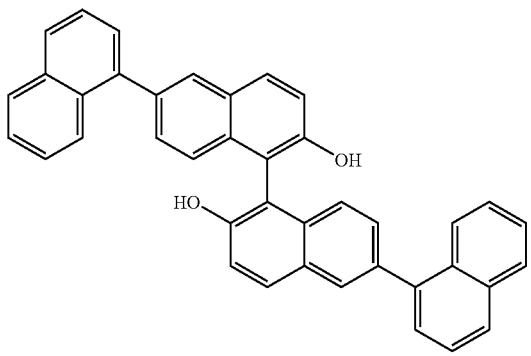

A solution of 53.0 g of iron(III) chloride, anhydrous, dissolved in 300 ml of water is added at 70° C. with stirring to a solution of 58.9 g (218 mmol) of 6-(1-naphthyl)-2-naphthol in 600 ml of ethanol. After the mixture has been stirred at 70° C. for 8 h, the solid is filtered off with suction and washed three times with 300 ml of water each time. The still-moist solid is suspended in 1000 ml of toluene. The solid is dried by removal of 800 ml of toluene by azeotropic distillation with vigorous stirring. After cooling, the solid is filtered off with suction, washed with heptane and dried in vacuo. Yield: 90.4 g (168 mmol), 77.0% of theory; purity: 97% according to NMR.

c) 6,6'-Bis(1-naphthyl)-peri-xanthenoxanthene

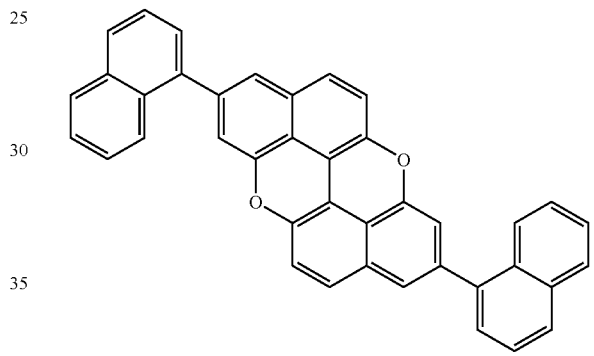

A suspension of 32.3 g (60 mmol) of 6,6'-(1-naphthyl)-1,1'-bi-2-naphthol and 33.4 g (420 mmol) of copper(II) oxide in 500 ml of nitrobenzene is heated on a water separator until the separation of water is complete (typically 2-3 h). The nitrobenzene is then removed by distillation to dryness. The residue is subjected to a Soxhlett extraction with chloroform until the extract running out no longer exhibits blue fluorescence. After the suspension has been cooled, the solid is filtered off with suction and washed with a little chloroform. Recrystallisation of the crude product four times from o-dichlorobenzene and subsequent sublimation at T=350° C. and p=$2\times10^{-5}$ mbar gives 24.7 g (46 mmol) of 6,6'-bis(1-naphthyl)-peri-xanthenoxanthene, corresponding to 77.0% of theory, with a purity of 99.9% according to HPLC.

Examples 12 to 14

Analogously to Example 11, the compounds shown in Table 2 are prepared, purified and sublimed. The yields indicated relate to step 11c). The yields in steps a) and b) are in each case comparable to those from Example 11.

TABLE 2

| Ex. | Product | Yield |
|---|---|---|
| 12 | 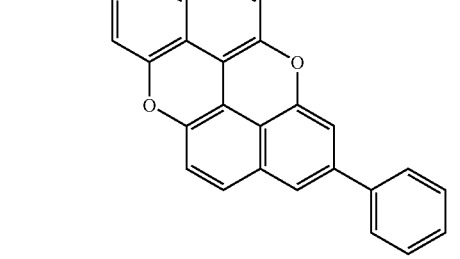 | 86.5% |
| 13 | 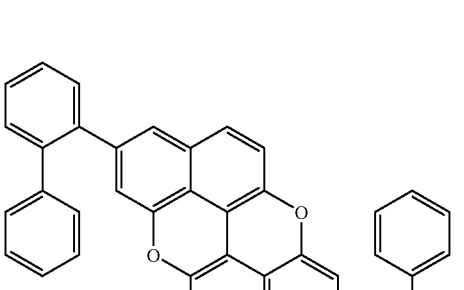 | 87.1% |
| 14 | 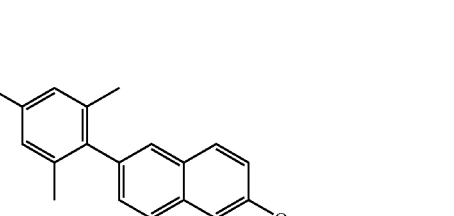 | 84.6% |

Example 16

5,5'-Bis(diphenylamino)-peri-xanthenoxanthene

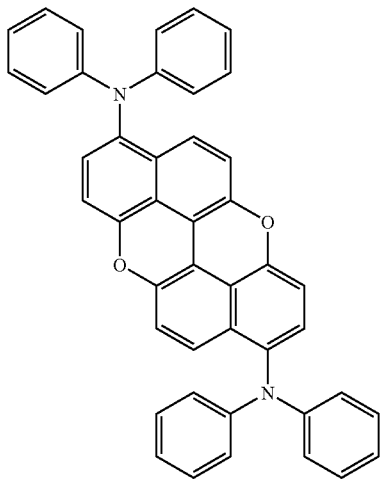

14.4 g (150 mmol) of sodium tert-butoxide, then 271 mg (1.5 mmol) of chloro-di-tert-butylphosphine and then 225 mg (1 mmol) of palladium(II) acetate are added to a suspension of 22.0 g (50 mmol) of 5,5'-dibromo-peri-xanthenoxanthene and 20.3 g (120 mmol) of diphenylamine in 500 ml of toluene, and the mixture is heated under reflux for 16 h. After cooling, 500 ml of water are added, the precipitated solid is filtered off with suction, washed three times with 300 ml of water/ethanol (1:1, v:v) each time and three times with 200 ml of ethanol each time. Recrystallisation of the crude product five times from chlorobenzene and subsequent sublimation at T=365° C. and p=$2 \times 10^{-5}$ mbar gives 17.9 g (29 mmol) of 5,5'-bis(diphenylamino)-peri-xanthenoxanthene, corresponding to 58.0% of theory, with a purity of 99.9% according to HPLC.

Example 16

6,6,12,12-Tetramethyl-4,10-bis(naphth-1-yl)-2,8-bis(bis-3-methylphenyl)amino-6H,12H-dibenzo[def,mno]chrysene

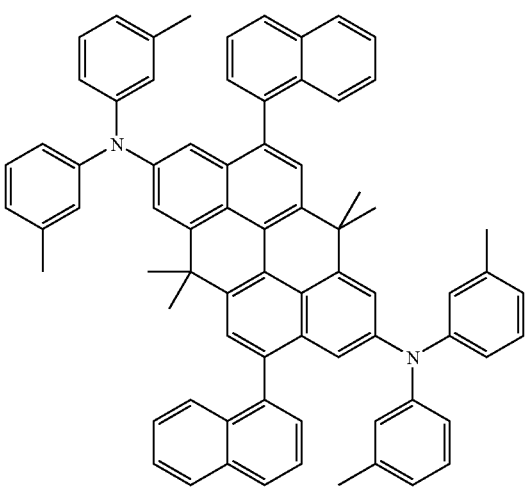

a) 6,6,12,12-Tetramethyl-6H,12H-dibenzo[def,mno]chrysene

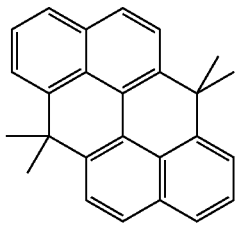

375 ml (600 mmol) of n-methyllithium (1.6 molar in diethyl ether) are added dropwise to a solution, cooled to −78° C., of 37.0 g (100 mmol) of 2,2'-bismethoxycarbonyl-1,1'-binaphthyl in 1000 ml of THF, and the mixture is subsequently stirred for a further 6 h. The mixture is allowed to warm slowly to room temperature, 200 ml of saturated ammonium chloride solution are added, the mixture is stirred vigorously for a further 15 min., and the organic phase is separated off and dried over magnesium sulfate. After removal of the THF, the oily residue is taken up in 500 ml of glacial acetic acid, 5 ml of conc. sulfuric acid are added, and the mixture is heated under reflux for 15 min. After cooling, the colourless crystals are filtered off with suction, washed with glacial acetic acid (3×100 ml) and ethanol (3×100 ml) and dried in vacuo Yield 29.7 g, corresponding to 88.7% of theory; purity 97% according to NMR.

b) 4,10-Dibromo-6,6,12,12-tetramethyl-6H,12H-dibenzo[def,mno]-chrysene

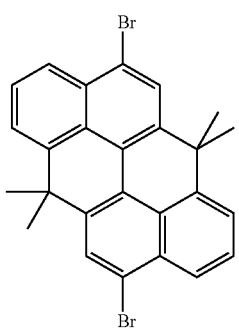

A mixture of 8.2 ml (160 mmol) of bromine in 200 ml of dichloromethane is added dropwise with exclusion of light to a solution, cooled to 0° C., of 26.8 g (80 mmol) of 6,6,12,12-tetramethyl-6H,12H-dibenzo[def,mno]chrysene in 300 ml of dichloromethane. When the addition is complete, the mixture is stirred until decolourised, then 1000 ml of ethanol are added, the mixture is stirred at room temperature for a further 14 h, and the colourless solid is filtered off with suction and subsequently washed with ethanol (3×100 ml) and dried in vacuo. Yield 37.3 g, corresponding to 94.7% of theory; purity 98% according to NMR.

c) 4,10-Bis(naphth-1 yl)-6,6,12,12-tetramethyl-6H,12H-dibenzo-[def,mno]chrysene

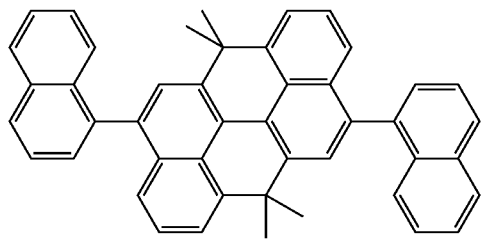

Procedure analogous to Example 4. The 22.0 g (50 mmol) of 6,6'-dibromo-peri-xanthenoxanthene are replaced by 24.6 g (50 mmol) of 4,10-dibromo-6,6,12,12-tetramethyl-6H,12H-dibenzo[def,mno]chrysene. Yield 25.0 g, corresponding to 85.2% of theory; purity 98% according to NMR.

d) 6,6,12,12-Tetramethyl-4,10-bis(naphth-1-yl)-2,8-dibromo-6H,12H-dibenzo[def,mno]chrysene

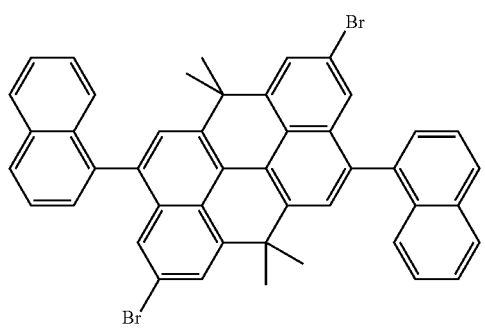

Procedure analogous to Example 16b). The 26.8 g (80 mmol) of 6,6,12,12-tetramethyl-6H,12H-dibenzo[def,mno] chrysene and 8.2 ml (160 mmol) of bromine are replaced by 20.5 g (35 mmol) of 4,10-bis(naphth-1-yl)-6,6,12,12-tetramethyl-6H,12H-dibenzo[def,mno]chrysene and 3.6 ml (70 mmol) of bromine. Recrystallisation of the crude product twice from DMF. Yield 19.6 g, corresponding to 75.2% of theory; purity 99.5% according to NMR.

e) 6,6,12,12-Tetramethyl-4,10-bis(naphth-1-yl)-2,8-bis(bis-3-methylphenyl)amino-6H,12H-dibenzo[def,mno]chrysene

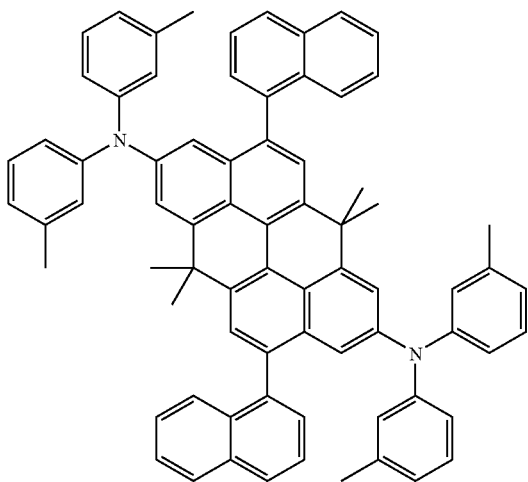

Procedure analogous to Example 15. The 22.0 g (50 mmol) of 5,5'-dibromo-peri-xanthenoxanthene are replaced by 14.9 g (20 mmol) of 6,6,12,12-tetramethyl-4,10-bis(naphth-1-yl)-2,8-dibromo-6H,12H-dibenzo-[def,mno]-chrysene. The remaining reagents are adjusted proportionally. Recrystallisation of the crude product three times from chlorobenzene and subsequent sublimation at T=355° C. and p=1×10$^{-5}$ mbar gives 10.1 g, corresponding to 51.7% of theory, with a purity of 99.9% according to HPLC.

Production of OLEDs

OLEDs are produced by a general process as described in WO 04/058911, which is adapted in individual cases to the particular circumstances (for example layer-thickness variation in order to achieve optimum efficiency or colour).

In Examples 17 to 28 below, the results for various OLEDs are presented. Glass plates coated with structured ITO (indium tin oxide) form the substrates of the OLEDs. For improved processing, 20 nm of PEDOT (spin-coated from water; purchased from H. C. Starck, Goslar, Germany; poly (3,4-ethylenedioxy-2,5-thiophene)) is applied to the substrate. The OLEDs consist of the following layer sequence: substrate/PEDOT/hole-injection layer (HIL1) 20 nm/hole-transport layer (HTM1) 60 nm/emission layer (EML) 30 nm/electron-transport layer (ETM1) 20 nm and finally a cathode. The materials apart from PEDOT are vapour-deposited thermally in a vacuum chamber. The emission layer here always consists of a matrix material (host) and a dopant, which is admixed with the host by co-evaporation. The cathode is formed by a 1 nm thin LiF layer and a 150 nm Al layer deposited on top. Table 3 shows the structures of the materials used to build up the OLEDs.

These OLEDs are characterised by standard methods; for this purpose, the electroluminescence spectra, the efficiency (measured in cd/A), the power efficiency (measured in lm/W) as a function of the luminance, calculated from current/voltage/luminance characteristics (IUL characteristics), and the lifetime are determined. The lifetime is defined as the time after which the initial luminance of 4000 cd/m² has dropped to half.

Table 4 shows the results for some OLEDs (Examples 17 to 28). As comparative example, dopant D1 and host H1 in accordance with the prior art are used.

TABLE 3

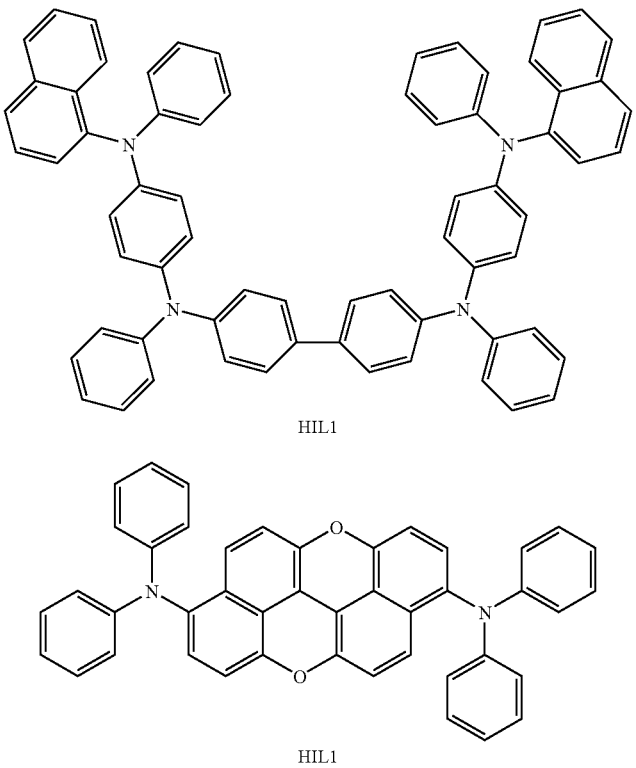

HIL1

HIL1

TABLE 3-continued
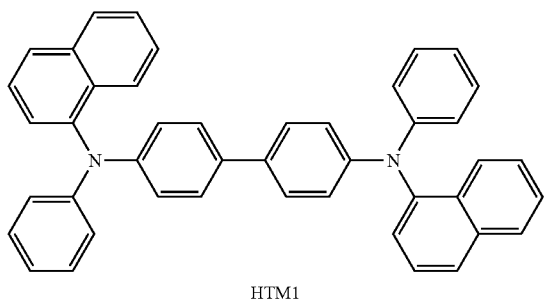
HTM1
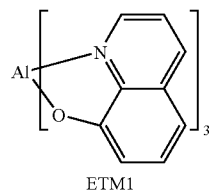
ETM1
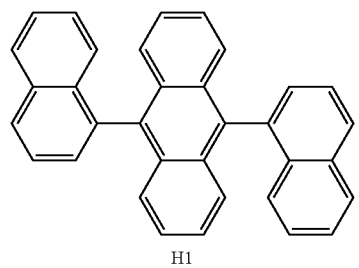
H1
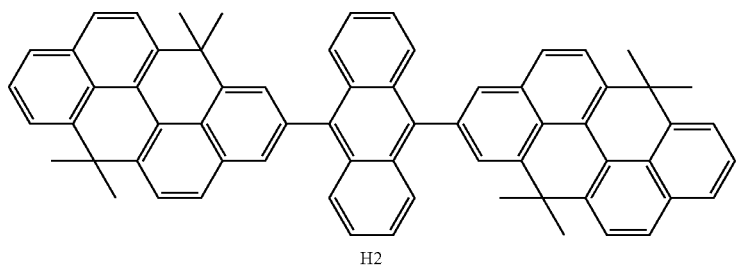
H2
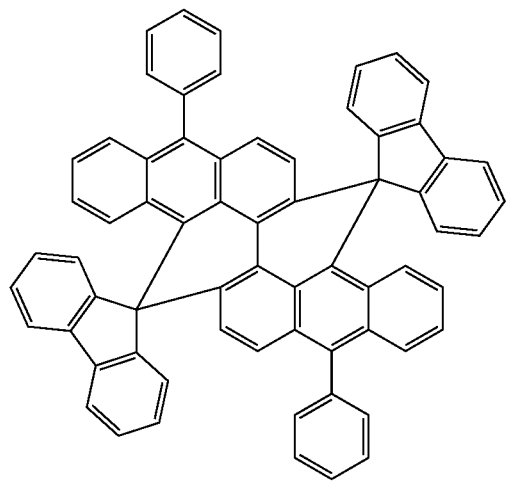
H3

TABLE 3-continued
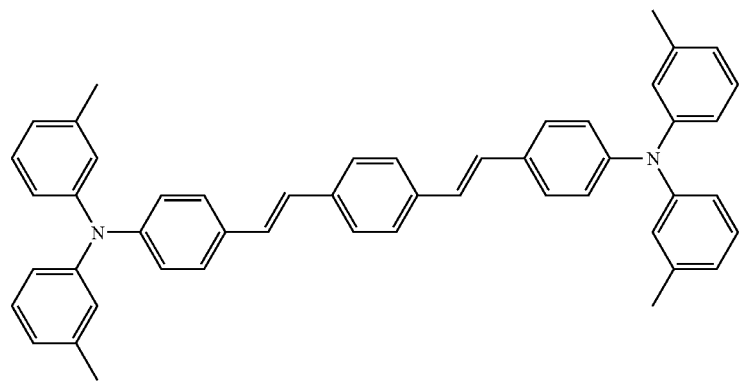
D1
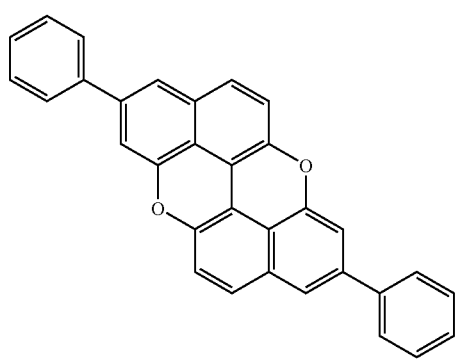
D2, HIL3
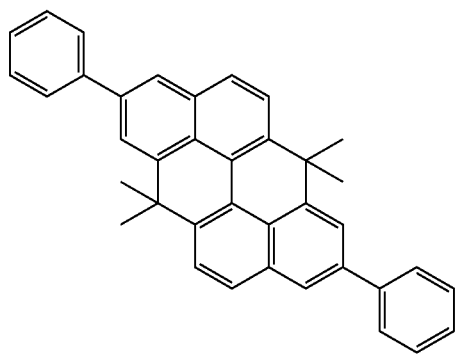
D3
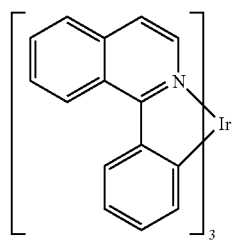
D4

TABLE 3-continued
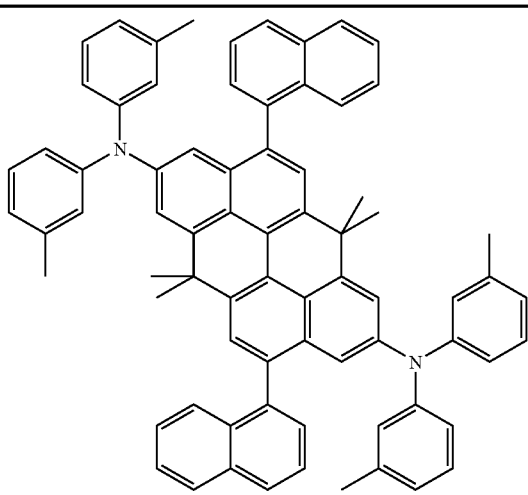
D5
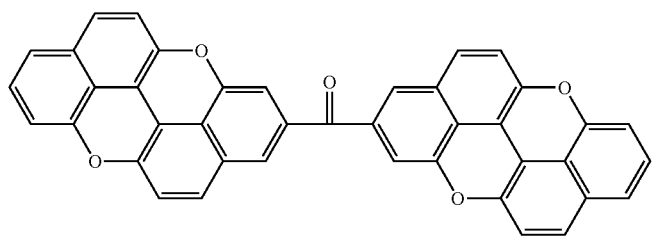
TMM1
TABLE 4
| Example | EML | HIL | Max. efficiency (cd/A) | Voltage (V) at 1000 cd/m$^2$ | CIE | Lifetime (h) at 4000 cd/m$^2$ |
| --- | --- | --- | --- | --- | --- | --- |
| 17 (comparison) | H1 + 5% of D1 | HIL1 | 9.8 | 5.8 | x = 0.17/y = 0.33 | 350 |
| 18 | H1 + 5% of D1 | HIL3 | 10.1 | 5.9 | x = 0.17/y = 0.33 | 500 |
| 19 | H1 + 5% of D2 | HIL3 | 9.5 | 5.7 | x = 0.16/y = 0.28 | 550 |
| 20 | H1 + 5% of D3 | HIL1 | 4.3 | 5.9 | x = 0.16/y = 0.09 | 380 |
| 21 | H2 + 5% of D1 | HIL1 | 10.3 | 5.7 | x = 0.17/y = 0.33 | 620 |
| 22 | H2 + 3% of D1 | HIL1 | 9.6 | 5.7 | x = 0.17/y = 0.30 | 590 |
| 23 | H1 + 5% of D1 | HIL2 | 11.8 | 5.9 | x = 0.17/y = 0.32 | 650 |
| 24 | H3 + 5% of D1 | HIL1 | 9.5 | 5.8 | x = 0.16/y = 0.28 | 480 |
| 25 | H3 + 7% of D1 | HIL1 | 9.7 | 5.7 | x = 0.16/y = 0.29 | 510 |
| 26 | TMM1 + 15% of D4 | HIL1 | 12 | 5.3 | x = 0.68/y = 0.32 | 950 |
| 27 | TMM1 + 10% of D4 | HIL1 | 13 | 5.2 | x = 0.68/y = 0.32 | 1100 |
| 28 | H1 + 5% of D5 | HIL1 | 5.5 | 5.6 | x = 0.15/y = 0.16 | 370 |

The invention claimed is:
1. A compound of the formulae (1) to (8):
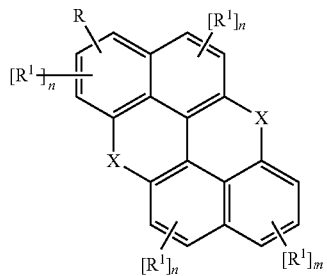
formula (1a)
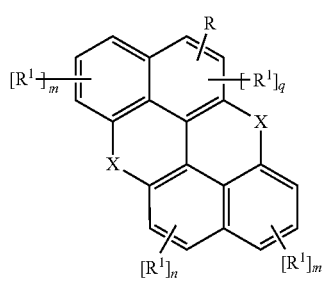
formula (1b)
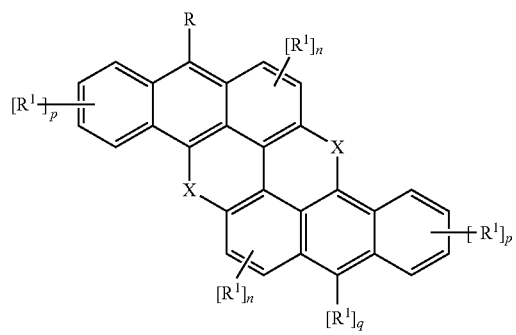
formula (2)
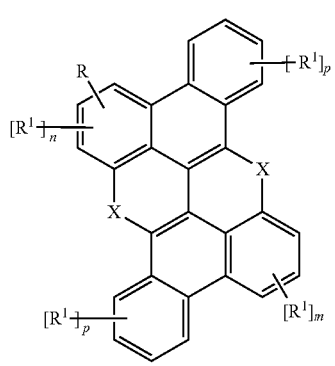
formula (3)
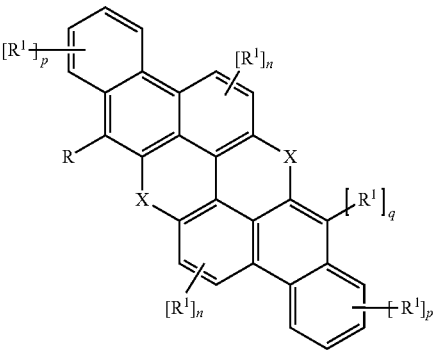
formula (4)
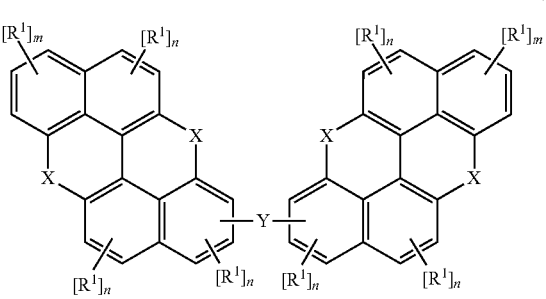
formula (5)
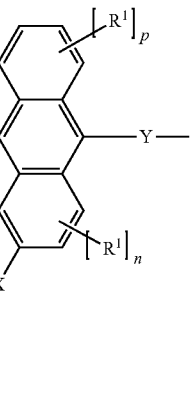
formula (6)
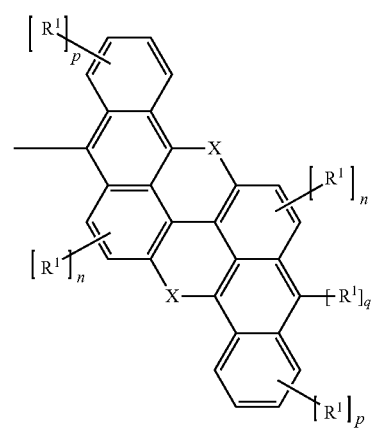

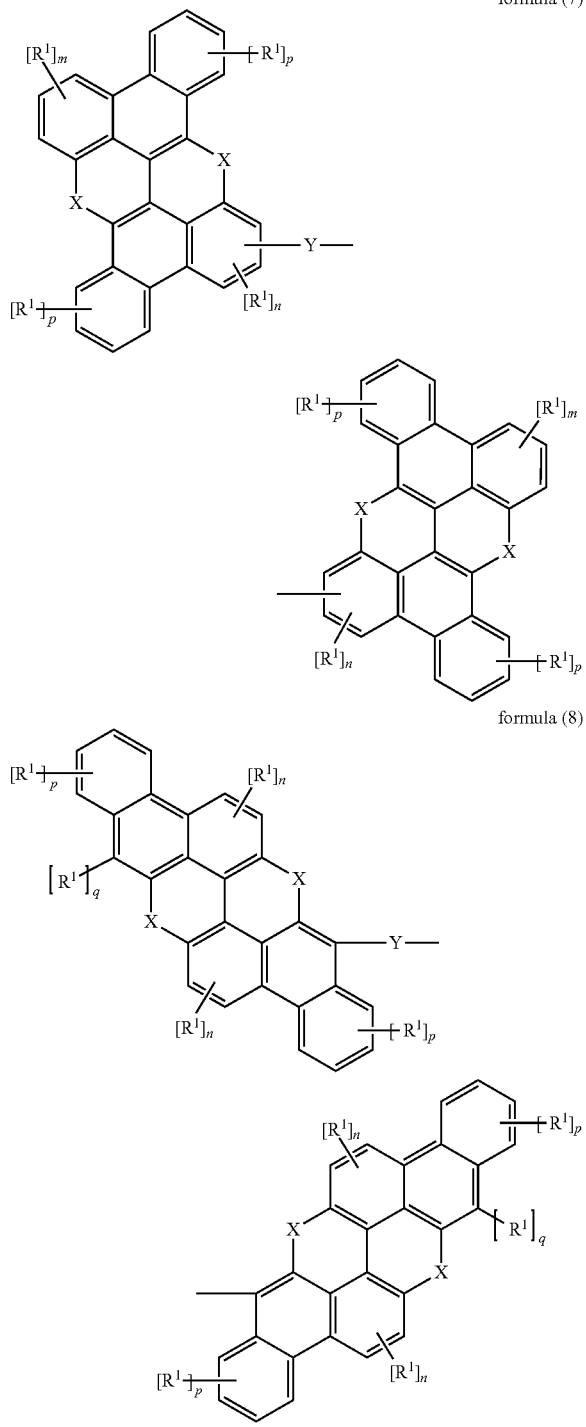

formula (7)

formula (8)

where the following applies to the symbols and indices:

X is on each occurrence, identically or differently, O, S, NR¹, C(R¹)₂, BR¹, PR¹, POR¹, SO or SO₂;

Y is a single bond, a C(=O), P(=O)Ar, N(Ar), S(=O), S(=O)₂, O, S group, an alkylene or alkylidene group having 1 to 20 C atoms or a divalent aromatic ring system having 5 to 40 aromatic ring atoms, which is optionally substituted by one or more non-aromatic radicals R¹;

R is on each occurrence, identically or differently, an N(Ar)₂, P(=O)Ar₂; S(=O)Ar, S(=O)₂Ar, CR²=CR²Ar, OAr, SAr, Si(R¹)₃ group, a straight-chain alkyl group having 1 to 40 C atoms, a branched or cyclic alkyl group having 3 to 40 C atoms, each of which is optionally substituted by one or more radicals R² and in which one or more H atoms is optionally replaced by F, Cl, Br, I, CN or NO₂, a straight-chain alkoxy group having 2 to 40 C atoms or a branched or cyclic alkoxy group having 3 to 40 C atoms, where the alkoxy group is optionally in each case substituted by one or more radicals R², where one or more non-adjacent CH₂ groups in the alkoxy groups is optionally replaced by R²C=CR², C≡C, Si(R²)₂, Ge(R²)₂, Sn(R²)₂, C=O, C=S, C=Se, C=NR², P(=O)(R²), SO, SO₂, NR², O, S or CONR² and where one or more H atoms is optionally replaced by F, Cl, Br, I, CN or NO₂, or an aromatic or heteroaromatic ring system having 5 to 60 aromatic ring atoms, each of which is optionally substituted by one or more non-aromatic radicals R¹; R here optionally forms a mono- or polycyclic ring system with adjacent substituents R¹;

R¹ is on each occurrence, identically or differently, H, F, Cl, Br, I, CHO, N(Ar)₂, C(=O)Ar, P(=O)Ar₂, S(=O)Ar, S(=O)₂Ar, CR²=CR²Ar, OAr, SAr, CN, NO₂, Si(R²)₃, B(OR²)₂, OSO₂R², a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals R², where one or more non-adjacent CH₂ groups is optionally replaced by R²C=CR², C≡C, Si(R²)₂, Ge(R²)₂, Sn(R²)₂, C=O, C=S, C=Se, C=NR², P(=O)(R²), SO, SO₂, NR², O, S or CONR² and where one or more H atoms is optionally replaced by F, Cl, Br, I, CN or NO₂, or an aromatic or heteroaromatic ring system having 5 to 60 aromatic ring atoms, each of which is optionally substituted by one or more non-aromatic radicals R¹, or a combination of these systems; two or more adjacent substituents R¹ here optionally form a mono- or polycyclic ring system with one another or R¹ with R;

Ar is on each occurrence, identically or differently, an aromatic or heteroaromatic ring system having 5 to 40 aromatic ring atoms, which is optionally substituted by one or more non-aromatic radicals R¹; two radicals Ar which are bonded to the same nitrogen or phosphorus atom are optionally linked to one another here by a single bond or a bridge wherein the bridge is B(R²), C(R²)₂, Si(R²)₂, C=O, C=NR², C=C(R²)₂, O, S, S=O, SO₂, N(R²), P(R²) or P(=O)R²;

R² is on each occurrence, identically or differently, H or an aliphatic, aromatic and/or heteroaromatic hydrocarbon radical having 1 to 20 C atoms, in which, in addition, H atoms is optionally replaced by F; two or more adjacent substituents R² here optionally form a mono- or polycyclic aliphatic or aromatic ring system with one another;

n is on each occurrence, identically or differently, 0, 1 or 2;

m is on each occurrence, identically or differently, 0, 1, 2 or 3;

p is on each occurrence, identically or differently, 0, 1, 2, 3 or 4;

q is on each occurrence, identically or differently, 0 or 1;

with the proviso that the following compounds are excluded:

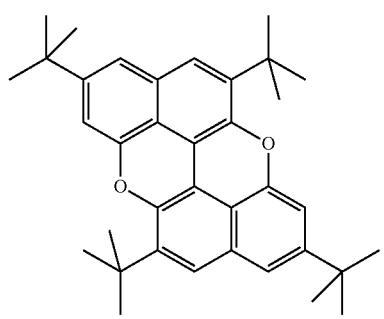
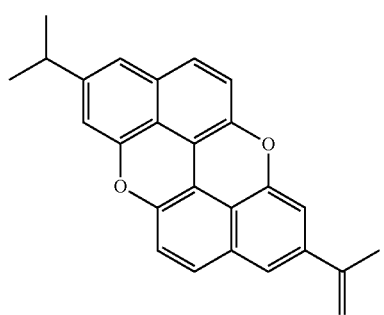
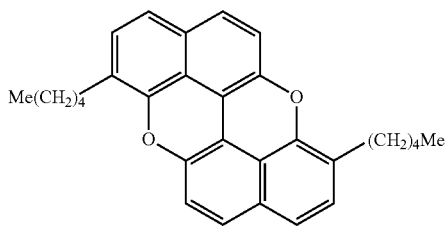
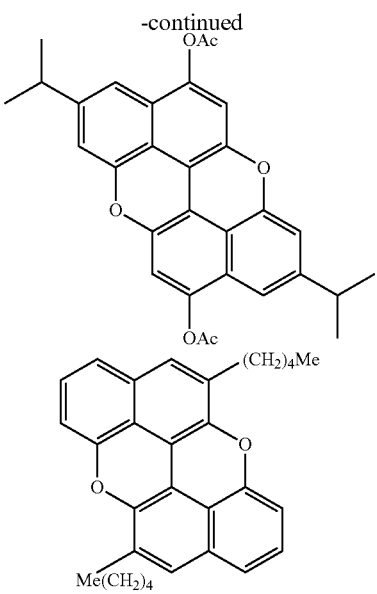
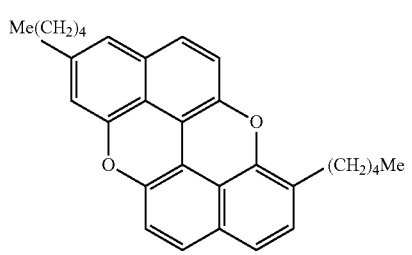
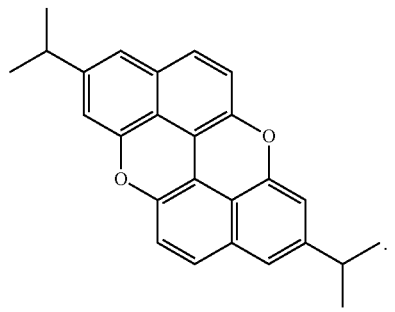
2. The compound as claimed in claim 1, wherein the compound is of the formulae (9) to (24):
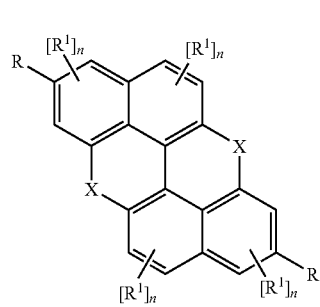
formula (9)
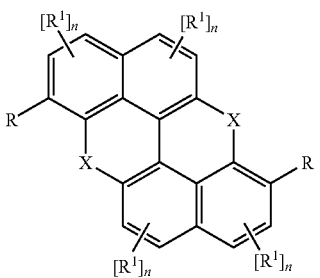
formula (10)

-continued
formula (11)
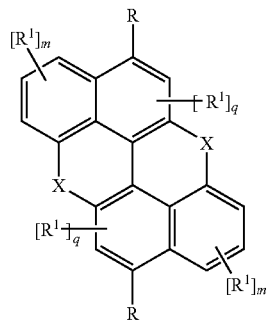
formula (12)
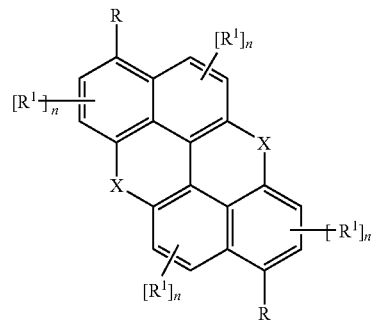
formula (13)
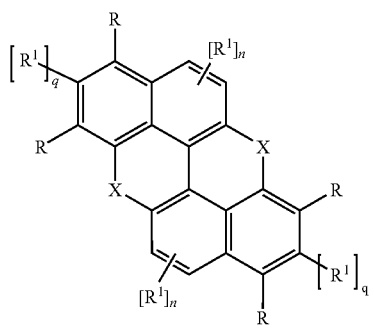
formula (14)
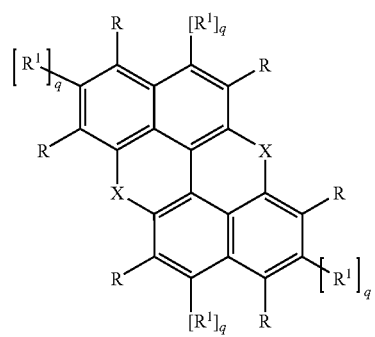
formula (15)
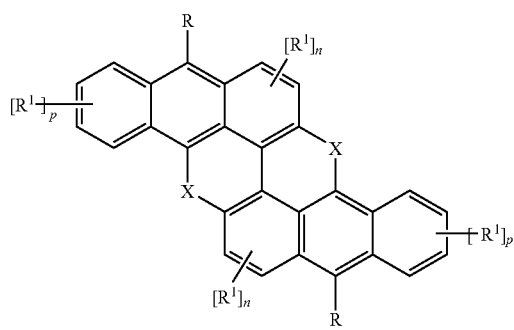
formula (16)
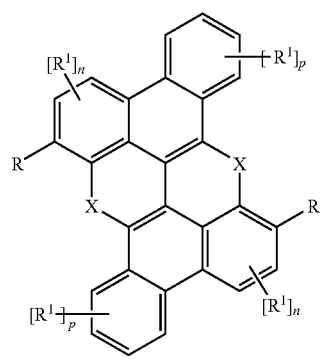
formula (17)
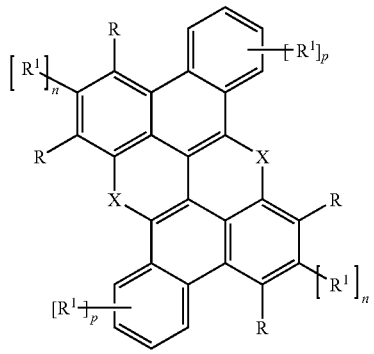
formula (18)
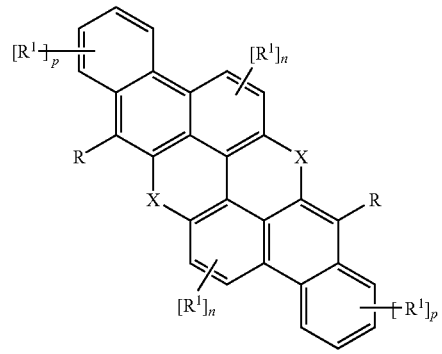

-continued
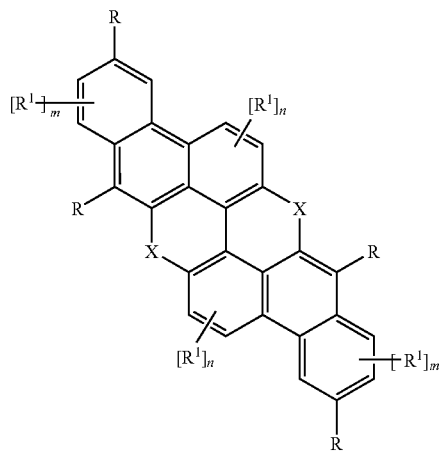
formula (19)
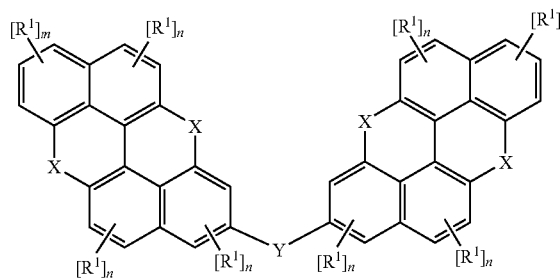
formula (20)
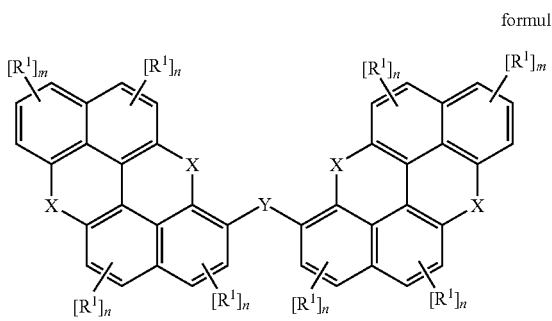
formula (21)
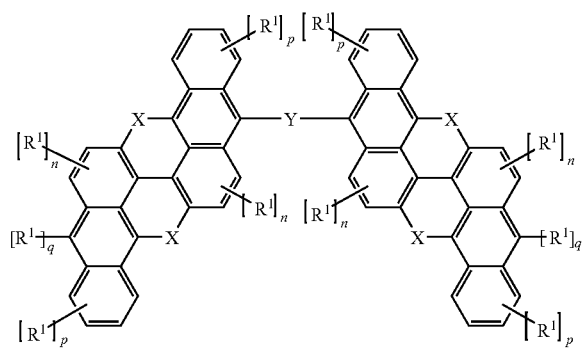
formula (22)
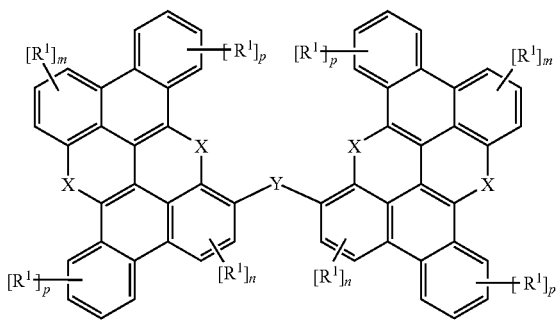
formula (23)
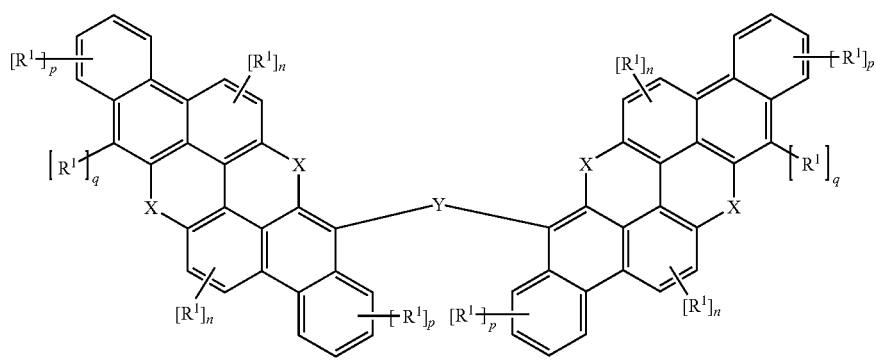
formula (24)
where R, $R^1$, $R^2$, Ar, X, Y, m, n, p and q have the same meaning as defined in claim 1.

3. The compound as claimed in claim 1, wherein the compound is of the formulae (9a) to (24a):
formula (9a)
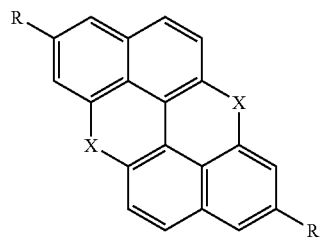
formula (10a)
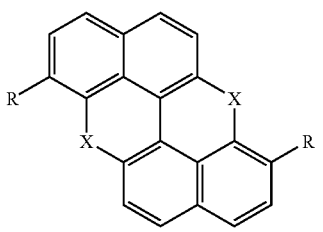
formula (11a)
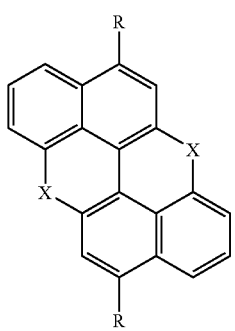
formula (12a)
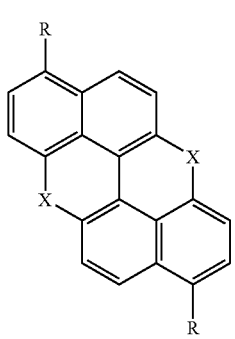
formula (13a)
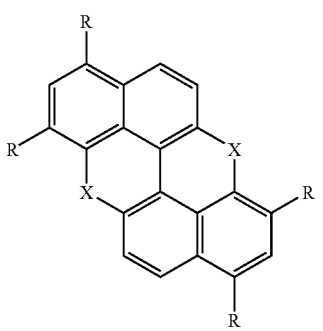
-continued
formula (14a)
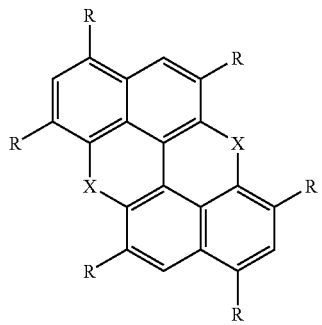
formula (15a)
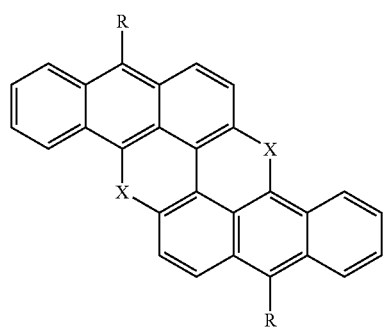
formula (16a)
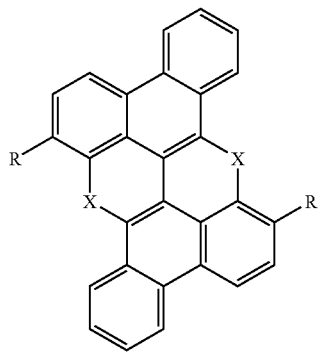
formula (17a)
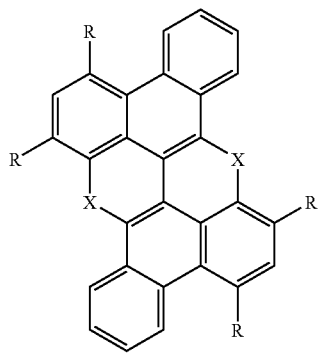

formula (18a)
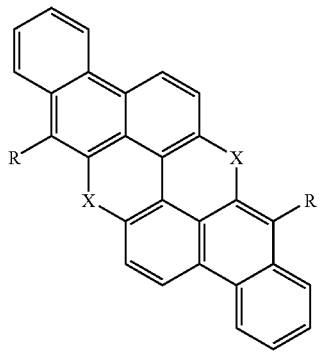

formula (22a)
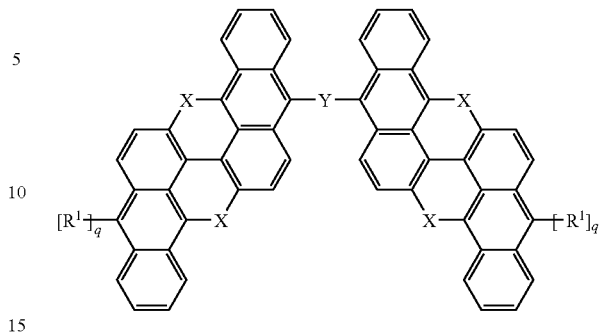

formula (19a)
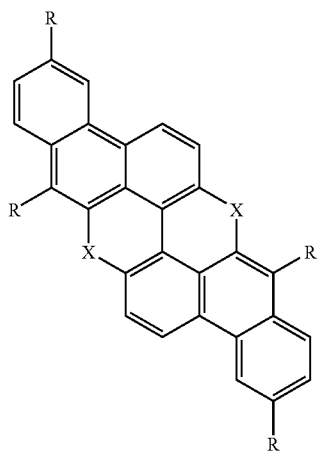

formula (23a)
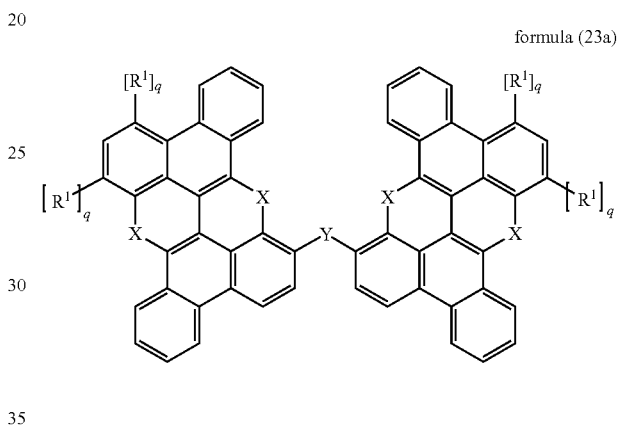

formula (24a)
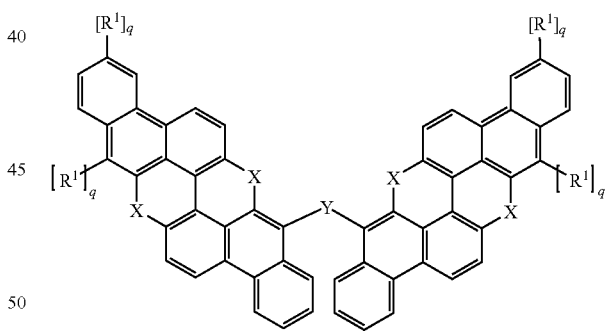

formula (20a)
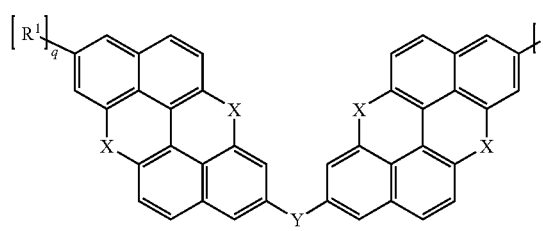

formula (21a)
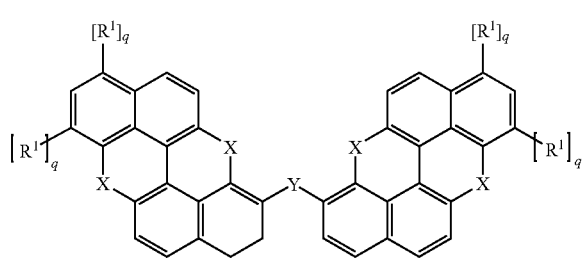

where R, $R^1$, $R^2$, Ar, X, Y and q have the same meaning as defined in claim 1.

4. The compound as claimed in claim 1, wherein R is identically or differently on each occurrence, and is an N(Ar)$_2$, P(=O)Ar$_2$ group, a straight-chain alkyl group having 1 to 4 C atoms or a branched alkyl group having 3 to 5 C atoms or an aromatic or heteroaromatic ring system having 5 to 25 aromatic ring atoms, which is optionally substituted by one or more non-aromatic radicals $R^1$, and Y is a C(=O) or N(Ar) group or a divalent aryl group having 6 to 16 C atoms, which is optionally substituted by one or more non-aromatic radicals $R^1$.

5. The compound as claimed in claim 1, wherein the compound has a symmetrical structure with respect to the substituents present.

6. A polymer, oligomer or dendrimer which comprises one or more compounds of the formulae (1) to (8):
formula (1a)
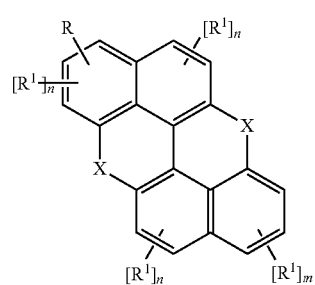
formula (1b)
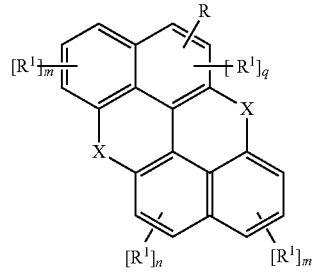
formula (2)
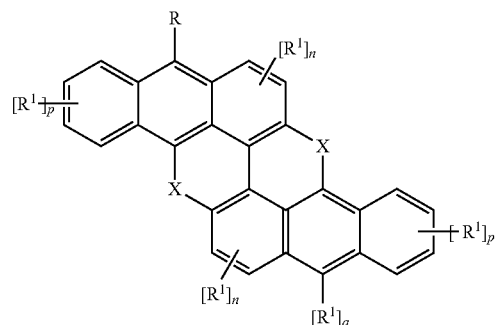
formula (3)
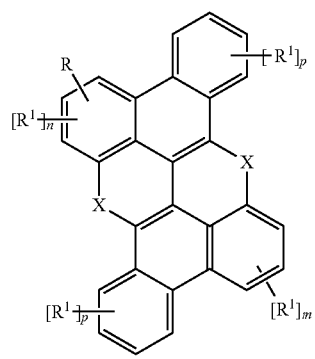
formula (4)
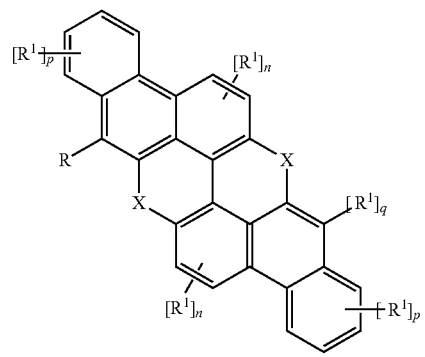
formula (5)
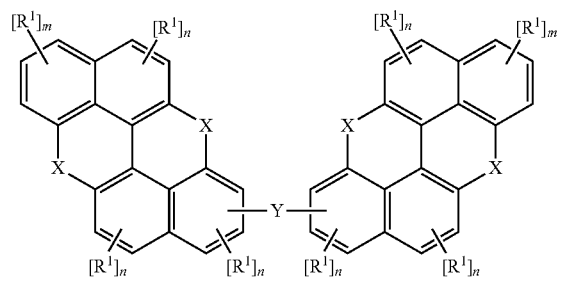
formula (6)
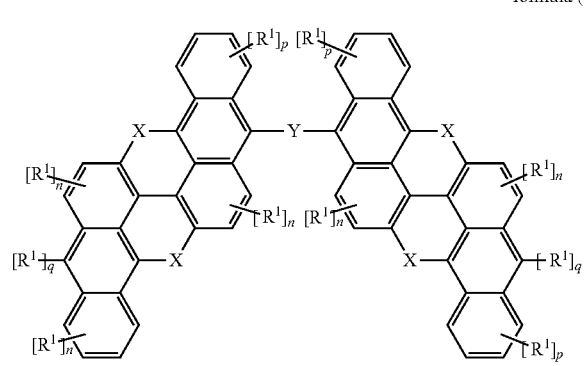
formula (7)
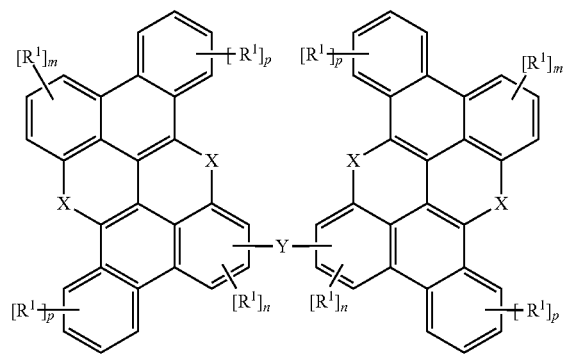

formula (8)

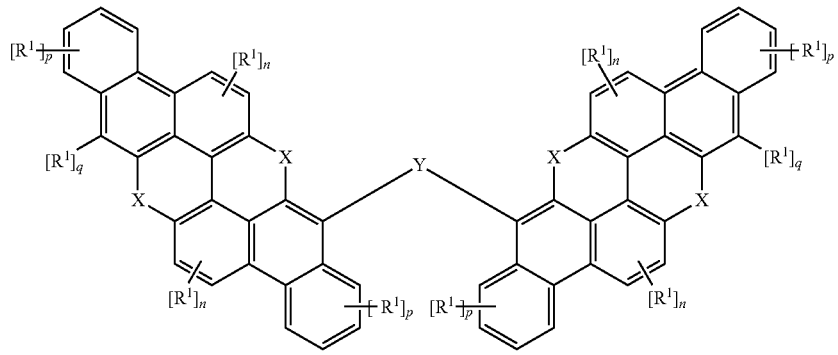

where the following applies to the symbols and indices:

X is on each occurrence, identically or differently, O, S, $NR^1$, $C(R^1)_2$, $BR^1$, $PR^1$, $POR^1$, SO or $SO_2$;

Y is a single bond, a C(=O), P(=O)Ar, N(Ar), S(=O), $S(=O)_2$, O, S group, an alkylene or alkylidene group having 1 to 20 C atoms or a divalent aromatic ring system having 5 to 40 aromatic ring atoms, which is optionally substituted by one or more non-aromatic radicals $R^1$;

R is on each occurrence, identically or differently, an $N(Ar)_2$, C(=O)Ar, P(=O)$Ar_2$, S(=O)Ar, $S(=O)_2Ar$, $CR^2=CR^2Ar$, OAr, SAr, $Si(R^1)_3$ group, a straight-chain alkyl group having 1 to 40 C atoms, a branched or cyclic alkyl group having 3 to 40 C atoms, each of which is optionally substituted by one or more radicals $R^2$ and in which one or more H atoms is optionally replaced by F, Cl, Br, I, CN or $NO_2$, a straight-chain alkoxy group having 2 to 40 C atoms or a branched or cyclic alkoxy group having 3 to 40 C atoms, where the alkoxy group is optionally in each case substituted by one or more radicals $R^2$, where one or more non-adjacent $CH_2$ groups in the alkoxy groups is optionally replaced by $R^2C=CR^2$, C≡C, $Si(R)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms is optionally replaced by F, Cl, Br, I, CN or $NO_2$, or an aromatic or heteroaromatic ring system having 5 to 60 aromatic ring atoms, each of which is optionally substituted by one or more non-aromatic radicals $R^1$; R here optionally forms a mono- or polycyclic ring system with adjacent substituents $R^1$;

$R^1$ is on each occurrence, identically or differently, H, F, Cl, Br, I, CHO, $N(Ar)_2$, C(=O)Ar, P(=O)$Ar_2$, S(=O)Ar, $S(=O)_2Ar$, $CR^2=CR^2Ar$, OAr, SAr, CN, $NO_2$, $Si(R^2)_3$, $B(OR^2)_2$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals $R^2$, where one or more non-adjacent $CH_2$ groups is optionally replaced by $R^2C=CR^2$, C≡C, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms is optionally replaced by F, Cl, Br, I, CN or $NO_2$, or an aromatic or heteroaromatic ring system having 5 to 60 aromatic ring atoms, each of which is optionally substituted by one or more non-aromatic radicals $R^1$, or a combination of these systems; two or more adjacent substituents $R^1$ here optionally form a mono- or polycyclic ring system with one another or $R^1$ with R;

Ar is on each occurrence, identically or differently, an aromatic or heteroaromatic ring system having 5 to 40 aromatic ring atoms, which is optionally substituted by one or more non-aromatic radicals $R^1$; two radicals Ar which are bonded to the same nitrogen or phosphorus atom are optionally linked to one another here by a single bond or a bridge wherein the bridge is $B(R^2)$, $C(R^2)_2$, $Si(R^2)_2$, C=O, $C=NR^2$, $C=C(R^2)_2$, O, S, S=O, $SO_2$, $N(R^2)$, $P(R^2)$ or $P(=O)R^2$;

$R^2$ is on each occurrence, identically or differently, H or an aliphatic, aromatic and/or heteroaromatic hydrocarbon radical having 1 to 20 C atoms, in which, in addition, H atoms is optionally replaced by F; two or more adjacent substituents $R^2$ here optionally form a mono- or polycyclic aliphatic or aromatic ring system with one another;

n is on each occurrence, identically or differently, 0, 1 or 2;

m is on each occurrence, identically or differently, 0, 1, 2 or 3;

p is on each occurrence, identically or differently, 0, 1, 2, 3 or 4;

q is on each occurrence, identically or differently, 0 or 1;

with the proviso that the following compounds are excluded:

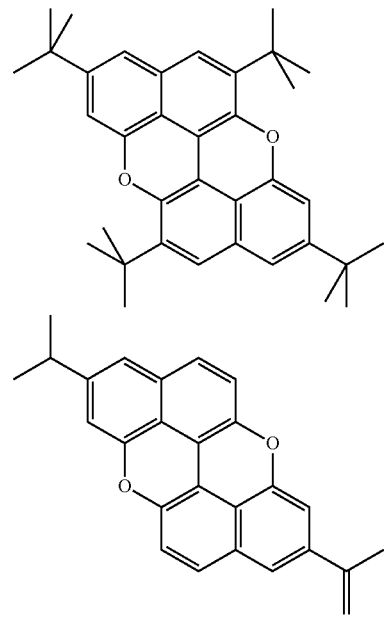

-continued

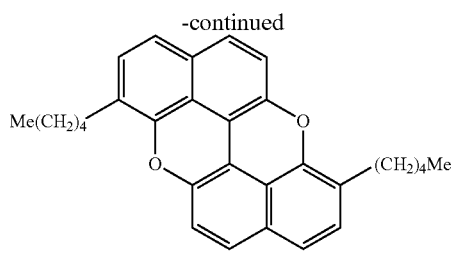

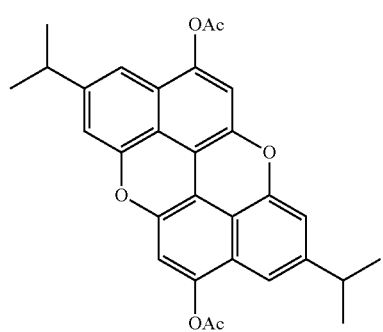

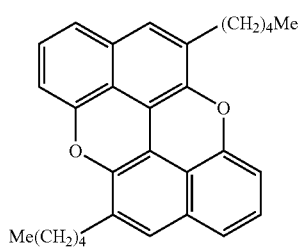

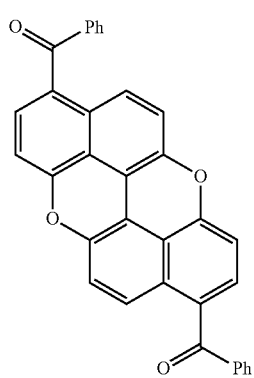

-continued

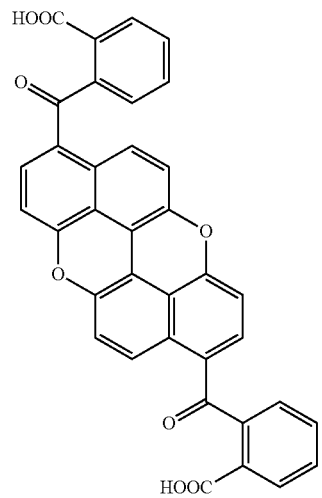

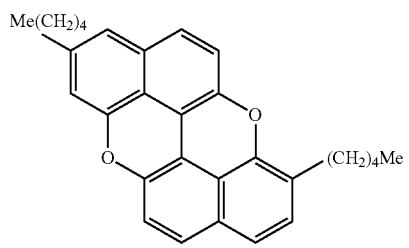

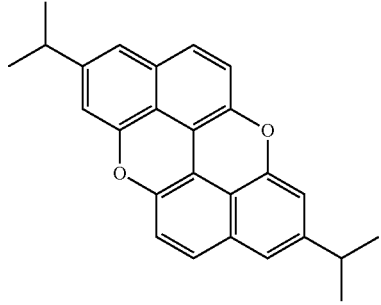

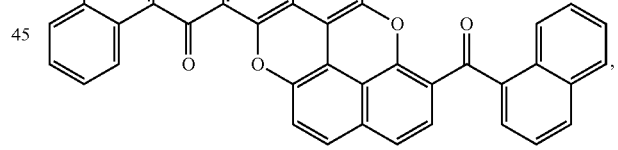

where one or more radicals R, $R^1$ and/or $R^2$ represent bonds to the polymer, oligomer or dendrimer.

7. A process for the preparation of the compounds according to claim 1 in which X=O, which comprises oxidative cyclisating the binaphthol or bianthrol or biphenanthrol derivative which has already been correspondingly functionalised.

8. A process for the preparation of the compound according to claim 1 in which X=C($R^1$)$_2$, which comprises acid-catalysed dehydrating cyclisation of the binaphthyl or bianthryl or biphenanthryl derivative which has optionally already been correspondingly functionalised and which is in each case substituted by two groups of the formula —C($R^1$)$_2$(OH) in the ortho-positions to the link of the binaphthyl or bianthryl or biphenanthryl.

9. An electronic device comprising at least one compound of the formulae (1) to (8):
formula (1a)
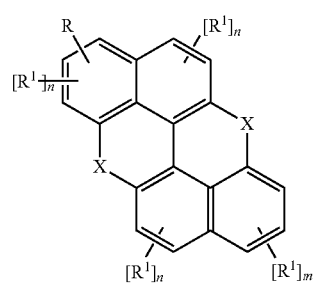
formula (1b)
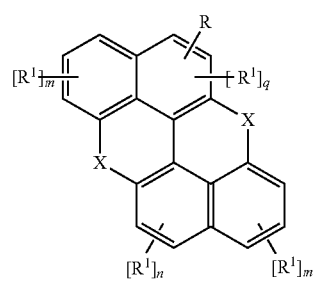
formula (2)
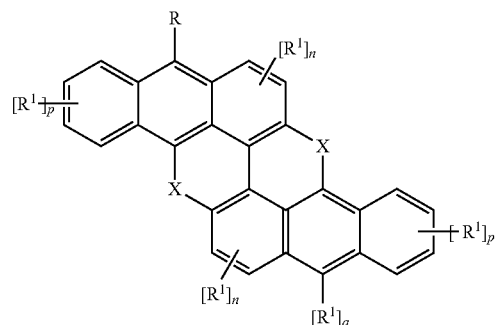
formula (3)
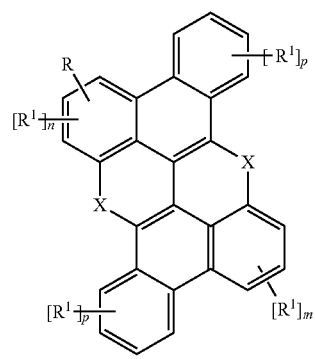
formula (4)
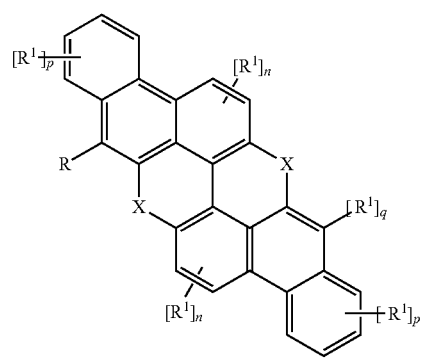
formula (5)
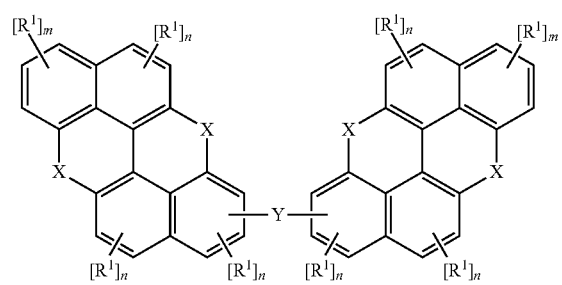
formula (6)
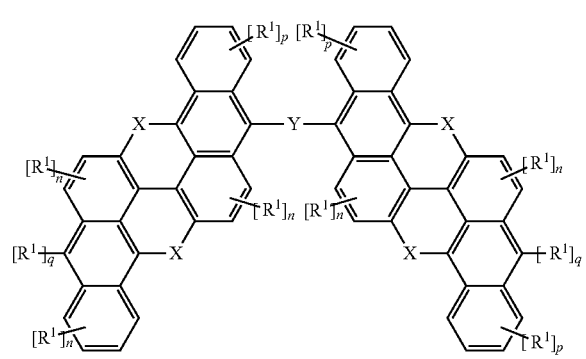
formula (7)
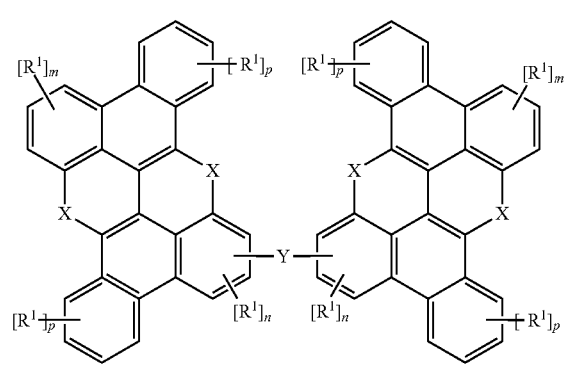

-continued

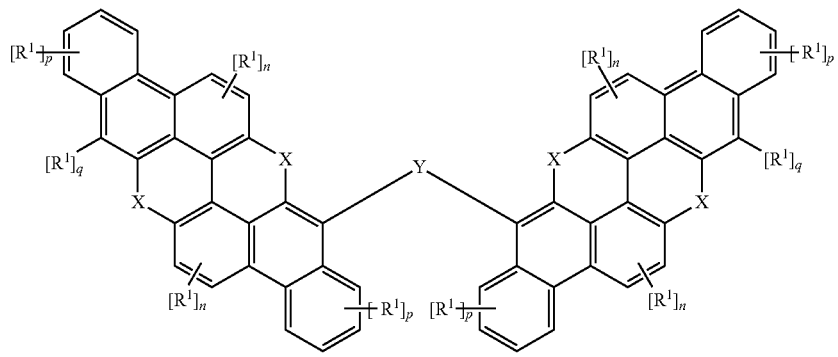

formula (8)

where the following applies to the symbols and indices:

X is on each occurrence, identically or differently, O, S, NR$^1$, C(R$^1$)$_2$, BR$^1$, PR$^1$, POR$^1$, SO or SO$_2$;

Y is a single bond, a C(=O), P(=O)Ar, N(A), S(=O), S(=O)$_2$, O, S group, an alkylene or alkylidene group having 1 to 20 C atoms or a divalent aromatic ring system having 5 to 40 aromatic ring atoms, which is optionally substituted by one or more non-aromatic radicals R$^1$;

R is on each occurrence, identically or differently, an N(Ar)$_2$, C(=O)Ar, P(=O)Ar$_2$, S(=O)Ar, S(=O)$_2$Ar, CR$^2$=CR$^2$Ar, OAr, SAr, Si(R$^1$)$_3$ group, a straight-chain alkyl group having 1 to 40 C atoms, a branched or cyclic alkyl group having 3 to 40 C atoms, each of which is optionally substituted by one or more radicals R$^2$ and in which one or more H atoms is optionally replaced by F, Cl, Br, I, CN or NO$_2$, a straight-chain alkoxy group having 2 to 40 C atoms or a branched or cyclic alkoxy group having 3 to 40 C atoms, where the alkoxy group is optionally in each case substituted by one or more radicals R$^2$, where one or more non-adjacent CH$_2$ groups in the alkoxy groups is optionally replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms is optionally replaced by F, Cl, Br, I, CN or NO$_2$, or an aromatic or heteroaromatic ring system having 5 to 60 aromatic ring atoms, each of which is optionally substituted by one or more non-aromatic radicals R$^1$; R here optionally forms a mono- or polycyclic ring system with adjacent substituents R$^1$;

R$^1$ is on each occurrence, identically or differently, H, F, Cl, Br, I, CHO, N(Ar)$_2$, C(=O)Ar, P(=O)Ar$_2$, S(=O)Ar, S(=O)$_2$Ar, CR$^2$=CR$^2$Ar, OAr, SAr, CN, NO$_2$, Si(R$^2$)$_3$, B(OR$^2$)$_2$, OSO$_2$R$^2$, a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals R$^2$, where one or more non-adjacent CH$_2$ groups is optionally replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms is optionally replaced by F, Cl, Br, I, CN or NO$_2$, or an aromatic or heteroaromatic ring system having 5 to 60 aromatic ring atoms, each of which is optionally substituted by one or more non-aromatic radicals R$_1$, or a combination of these systems; two or more adjacent substituents R$^1$ here optionally form a mono- or polycyclic ring system with one another or R$^1$ with R;

Ar is on each occurrence, identically or differently, an aromatic or heteroaromatic ring system having 5 to 40 aromatic ring atoms, which is optionally substituted by one or more non-aromatic radicals R$^1$; two radicals Ar which are bonded to the same nitrogen or phosphorus atom are optionally linked to one another here by a single bond or a bridge wherein the bridge is B(R$^2$), C(R$^2$)$_2$, Si(R$^2$)$_2$, C=O, C=NR$^2$, C=C(R$^2$)$_2$, O, S, S=O, SO$_2$, N(R$^2$), P(R$^2$) or P(=O)R$^2$;

R$^2$ is on each occurrence, identically or differently, H or an aliphatic, aromatic and/or heteroaromatic hydrocarbon radical having 1 to 20 C atoms, in which, in addition, H atoms is optionally replaced by F; two or more adjacent substituents R$^2$ here optionally form a mono- or polycyclic aliphatic or aromatic ring system with one another;

n is on each occurrence, identically or differently, 0, 1 or 2;

m is on each occurrence, identically or differently, 0, 1, 2 or 3;

p is on each occurrence, identically or differently, 0, 1, 2, 3 or 4;

q is on each occurrence, identically or differently, 0 or 1;

with the proviso that the following compounds are excluded:

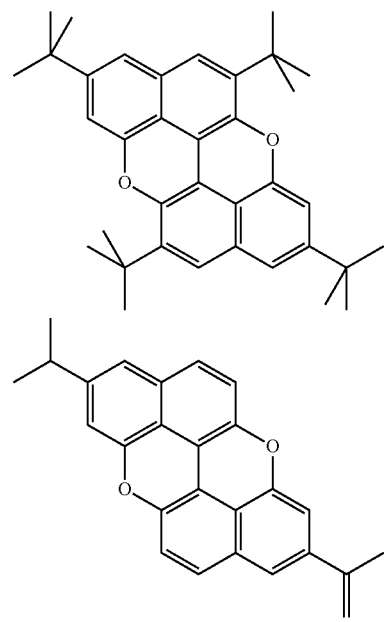

-continued

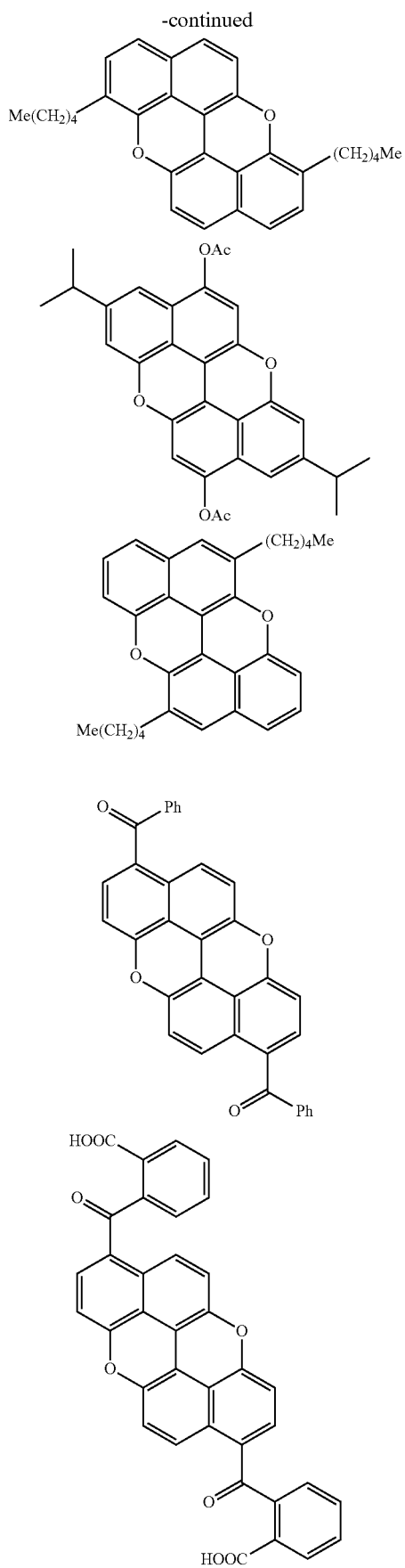

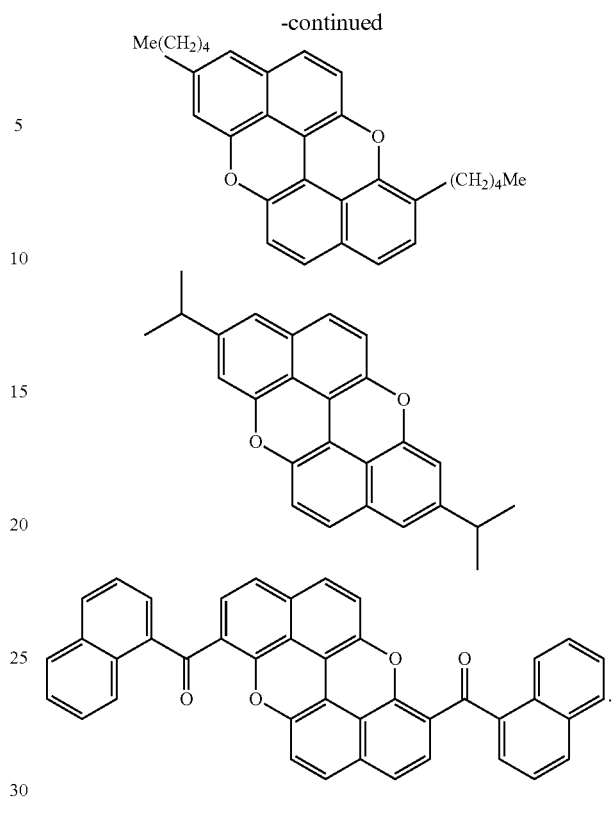

10. The organic electroluminescent device as claimed in claim 9, comprising anode, cathode, at least one emitting layer and optionally further layers selected from hole-injection layer, hole-transport layer, electron-transport layer, electron-injection layer and/or charge-generation layer, wherein at least one organic layer comprises at least one compound of the formulae (1) to (8).

11. The organic electroluminescent device according to claim 10, wherein X is O, S or $N(R^1)$ and the compound is employed as emitting compound, optionally mixed with a host material.

12. The organic electroluminescent device according to claim 10, wherein X is $C(R^1)_2$ and the compound is employed as host material for fluorescent or phosphorescent dopants.

13. The organic electroluminescent device according to claim 10, wherein X is O, S or $N(R^1)$ and/or in that at least one group R and/or $R^1$ stands for an $N(Ar)_2$ group and/or in that the group Y is an N(Ar) group, in the compound may optionally be doped and in that the compound is employed as hole-transport material or as hole-injection material.

14. The organic electroluminescent device according to claim 10, wherein X is O, S or $N(R^1)$ and/or in that at least one group R and/or $R^1$ stands for an $N(Ar)_2$ group and/or in that the group Y is an N(Ar) group, in the compound may optionally be doped and in that the compound is employed as a hole-transport or hole-injection layer respectively.

15. The organic electroluminescent device according to claim 10, wherein X is $C(R^1)_2$, $BR^1$, $POR^1$, SO or $SO_2$ and in that one or more of the substituents R and/or $R^1$ optionally stand for a C(=O)Ar or P(=O)$Ar_2$ group or for an electron-deficient heterocycle and/or the group Y stands for a C(=O) or P(=O)Ar group, in that the compound may optionally be doped and in that the compound is employed in an electron-transport layer and/or a hole-blocking layer.

16. The organic electroluminescent device according to claim 10, wherein the device is a blue-emitting device.

* * * * *